(12) United States Patent
Parke et al.

(10) Patent No.: US 12,138,519 B2
(45) Date of Patent: Nov. 12, 2024

(54) APPARATUS AND METHOD FOR GOLF ALIGNMENT TRAINING

(71) Applicant: SkyHawke Technologies, LLC, Ridgeland, MS (US)

(72) Inventors: Gord Parke, Winnipeg (CA); Jeremy Rittenhouse, Lancaster, PA (US); Richard C. Edmonson, Ridgeland, MS (US)

(73) Assignee: SkyHawke Technologies, LLC, Ridgeland, MS (US)

( * ) Notice: Subject to any disclaimer, the term of this patent is extended or adjusted under 35 U.S.C. 154(b) by 0 days.

(21) Appl. No.: 18/390,900

(22) Filed: Dec. 20, 2023

(65) Prior Publication Data
US 2024/0189693 A1 Jun. 13, 2024

Related U.S. Application Data

(63) Continuation-in-part of application No. 18/538,679, filed on Dec. 13, 2023, which is a continuation-in-part of application No. 17/987,442, filed on Nov. 15, 2022.

(60) Provisional application No. 63/279,576, filed on Nov. 15, 2021.

(51) Int. Cl.
A63B 69/36 (2006.01)

(52) U.S. Cl.
CPC ...... A63B 69/3632 (2013.01); A63B 2220/12 (2013.01); A63B 2220/30 (2013.01)

(58) Field of Classification Search
CPC ............ A63B 69/3632; A63B 2220/12; A63B 2220/30
See application file for complete search history.

(56) References Cited

U.S. PATENT DOCUMENTS

| 8,840,483 | B1 | 9/2014 | Steusloff et al. |
| 8,905,856 | B2 | 12/2014 | Parke et al. |
| 8,998,717 | B2 | 4/2015 | Parke et al. |
| 9,211,439 | B1* | 12/2015 | Pedenko ............... A63B 69/36 |
| 9,395,385 | B2 | 7/2016 | Parke et al. |
| 9,737,817 | B1 | 8/2017 | Ricky |
| 9,999,821 | B2 | 6/2018 | Yarmis et al. |
| 10,589,161 | B2 | 3/2020 | Blanc |
| 11,045,688 | B2 | 6/2021 | Meadows et al. |
| 11,148,026 | B2 | 10/2021 | Syed et al. |
| 11,219,814 | B2 | 1/2022 | Syed et al. |
| 2017/0234706 | A1* | 8/2017 | Martin .................... G01S 19/19 29/407.05 |
| 2017/0312572 | A1 | 11/2017 | Thornton et al. |
| 2018/0001184 | A1 | 1/2018 | Tran et al. |

(Continued)

FOREIGN PATENT DOCUMENTS

| EP | 3978949 A2 | 4/2022 | |
| WO | WO-2018204538 A1 * | 11/2018 | ........... A61B 5/1122 |

Primary Examiner — Raleigh W Chiu
(74) Attorney, Agent, or Firm — NEO IP

(57) ABSTRACT

Apparatuses and methods for golf alignment training include a device, attachable to a golf club, for measuring a golfer's alignment by a plurality of sensors, including a magnetometer. A location-aware device is used to select an intended target line. The plurality of sensors measure the golfer's actual alignment, including the face angle of the golf club at address of the ball, and the actual alignment is compared to the intended target line to provide feedback and suggested improvements.

20 Claims, 31 Drawing Sheets

(56) References Cited

U.S. PATENT DOCUMENTS

| | | |
|---|---|---|
| 2018/0050254 A1* | 2/2018 | Maani .................... G06V 40/23 |
| 2020/0276488 A1 | 9/2020 | Cottam et al. |
| 2020/0398138 A1 | 12/2020 | Hendrix et al. |
| 2021/0069568 A1* | 3/2021 | Meadows .............. G06N 20/00 |
| 2021/0343390 A1 | 11/2021 | Cohen et al. |
| 2022/0161121 A1 | 5/2022 | Syed et al. |
| 2023/0149789 A1 | 5/2023 | Root et al. |

* cited by examiner

| BLE ADVERTISEMENT RATE ||
|---|---|
| Power State or Tag Device Condition | Advertisement Interval Rate (milliseconds) |
| Data Collection State | 100 ms |
| Active State | 750 ms |
| Inactive | 750 ms for 30 seconds, then stop |
| Dark | None |
| On Power State Change | 100 ms for 3 seconds |
| On Advertisement Data Change | 100 ms for 3 seconds |

FIG. 8C

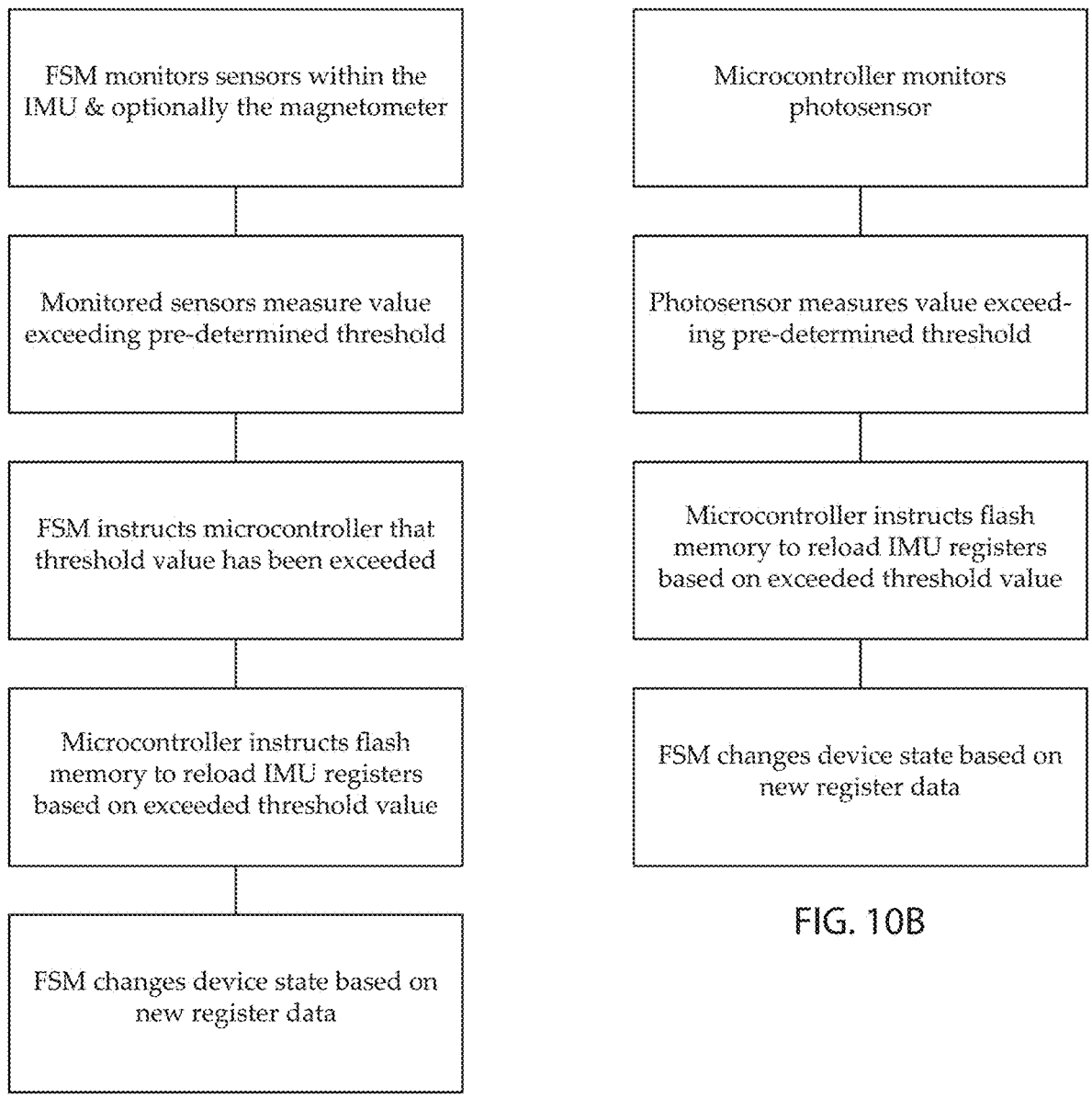

APPARATUS AND METHOD FOR GOLF ALIGNMENT TRAINING

CROSS REFERENCES TO RELATED APPLICATIONS

This application is related to and claims priority from one or more prior filed US patent applications. This application is a continuation-in-part of U.S. patent application Ser. No. 18/538,679, filed Dec. 13, 2023, which is a continuation-in-part of U.S. patent application Ser. No. 17/987,442, filed Nov. 15, 2022, which claims priority to and the benefit of U.S. Provisional Application No. 63/279,576, filed Nov. 15, 2021, each of which is incorporated herein by reference in its entirety.

BACKGROUND OF THE INVENTION

1. Field of the Invention

The present invention relates to apparatuses and methods for golf training, and more particularly golf alignment training.

2. Description of the Prior Art

It is generally known in the art to provide a device to monitor and track a golfer's shots during a round of golf using sensors associated with the golfer or the golf club, including automatic detection that a golf shot has occurred. It is also generally known in the art to provide a device to analyze a golfer's swing during practice using sensors attached to the golf club to generate a 2-D or 3-D image of the swing, such as the SKYPRO swing analyzer training aid produced by SKYGOLF.

Prior art patent documents include the following:

US Patent Pub. No. 2022/0161121 for Autonomous Tracking and Personalized Golf Recommendation and Analysis Environment by inventors Syed et al. filed Jan. 10, 2022 and published May 26, 2022, discloses systems, methods, and computer-readable media configured to autonomously track a round of golf and/or autonomously generate personalized recommendations for a user before, during, or after a round of golf. The systems and methods can utilize course data, environmental data, user data, and/or equipment data in conjunctions with one or more machine learning algorithms to autonomously generate the personalized recommendations.

U.S. Pat. No. 11,219,814 for Autonomous personalized golf recommendation and analysis environment by inventors Syed et al. filed Jun. 10, 2020 and issued Jan. 11, 2022, discloses systems, methods, and computer-readable media configured to autonomously generate personalized recommendations for a user before, during, or after a round of golf. The systems and methods can utilize course data, environmental data, user data, and/or equipment data in conjunctions with one or more machine learning algorithms to autonomously generate the personalized recommendations.

U.S. Pat. No. 10,589,161 for System and method for monitoring performance characteristics associated with user activities involving swinging instruments by inventor Blanc, filed Sep. 25, 2017 and issued Mar. 17, 2020, discloses various components of a system for monitoring and/or tracking a user's performance during an activity involving an instrument that is swung. Exemplary embodiments can include a sensor module configured to be secured to and/or embedded within the instrument. The sensor module can detect a swing event and/or an impact between the instrument and an object and can generate pressures waves that propagate through air. The pressure waves can include information or represent information about a use of the instrument and can be detected by an electronic device associated with the user, which can display the information, process the information, and/or transmit the information to a remote system. The pressure waves can be modulated to encode information within the pressure waves.

U.S. Pat. No. 9,999,821 for Method for monitoring performance characteristics associated with user activities involving swinging instruments by inventors Yarmis et al. filed Jul. 13, 2016 and issued Jun. 19, 2018, discloses methods for attachment of devices to a swinging instrument, the devices generally including a cover, a base, a chassis, and positive and negative electrical contacts. The base includes a fastening portion and a support portion. The chassis supports a printed circuit board. The devices include a cap configured and dimensioned to mate relative to the support portion of the base. The support portion can support the chassis, the printed circuit board, the positive and negative electrical contacts, and the cap. The cover can be configured and dimensioned to detachably interlock relative to the base. In the mated configuration, the cap and the base can form a battery opening configured and dimensioned to receive therethrough a battery.

U.S. Pat. No. 11,148,026 for System and method for monitoring performance characteristics associated with user activities involving swinging instruments by inventors Syed et al., filed Sep. 30, 2019 and issued Oct. 19, 2021, discloses various components of a system for monitoring and/or tracking a user's performance during an activity involving an instrument that is swung. Exemplary embodiments can include a sensor module configured to be secured to the instrument. The sensor module can detect a swing event and/or an impact between the instrument and an object and can implement power management features to limit or manage a power consumption of the sensor module. The sensor module can transmit swing information to an electronic device associated with the user, which can display the swing information, process the swing information, and/or transmit the swing information to a remote system.

U.S. Pat. No. 9,395,385 for Method and apparatus for determining a relative orientation of points on a rigid body by inventor Parke et al., filed Dec. 4, 2014 and issued Jul. 19, 2016, discloses an inertial measurement unit that is affixed to a rigid body. The inertial measurement includes a gyroscope that measures a first angular velocity and an angular acceleration; a first accelerometer that measures a first acceleration; a communications unit that receives a measurement signal, the measurement signal including a second acceleration transmitted from a second accelerometer, the second accelerometer being affixed to the rigid body; and a controller that calculates a relative orientation of the inertial measurement unit and the second accelerometer, and a distance separating the inertial measurement unit and the second accelerometer.

U.S. Pat. No. 8,905,856 for Method and Apparatus for determining a relative orientation of points on a rigid body by inventors Parke et al., filed Jan. 17, 2013 and issued Dec. 9, 2014, discloses an inertial measurement unit that is affixed to a rigid body. The inertial measurement includes a gyroscope that measures a first angular velocity and an angular acceleration; a first accelerometer that measures a first acceleration; a communications unit that receives a measurement signal, the measurement signal including a second acceleration transmitted from a second accelerometer, the second accelerometer being affixed to the rigid body; and a controller that calculates a relative orientation of the inertial measurement unit and the second accelerometer, and a distance separating the inertial measurement unit and the second accelerometer.

U.S. Pat. No. 8,998,717 for Device and method for reconstructing and analyzing motion of a rigid body by inventors Parke et al., filed Jan. 17, 2013 and issued Apr. 7, 2015, discloses an information processing apparatus including circuitry configured to acquire information corresponding to a reference orientation that indicates a spatial position of a sensor unit attached to a golf club. The reference orientation is determined based on a vector projecting in a normal direction from a planar surface of the golf club. The circuitry acquires a measurement signal generated by the sensor unit in response to a movement of the golf club, the measurement signal including measurements of one or more of an angular acceleration, a linear acceleration, and an angular velocity. The circuitry generates data corresponding to a motion path of the golf club based on the measurement signal and the reference orientation. The circuitry controls an interface to output the generated data corresponding to the motion path.

U.S. Pat. No. 11,045,688 for Golf shot tracking system by inventors Meadows, et al., filed Sep. 26, 2018 and issued Jun. 29, 2021, discloses a golf tracking system including a tag coupled to a golf club. The tag includes a plurality of sensors, including an accelerometer, each of which output a signal based on detected movement of the golf club, a microcontroller compares each of the plurality of sensor outputs to stored referenced sensor output values, and a transceiver that transmits data corresponding to the sensor outputs to a device remote from the tag based on the comparison performed by the microcontroller. The location-aware device then processes the information received from the tag to determine whether a shot should be registered.

U.S. Pat. No. 8,840,483 for Device, system, and method for evaluation of a swing of a piece of athletic equipment by inventors Steusloff, et al., filed Sep. 23, 2011 and issued Sep. 23, 2014, discloses an evaluation device and methods for evaluating the swing of a piece of athletic equipment. The evaluation device may include a microphone, an accelerometer, and a microcontroller configured to detect a stroke and ball strike and track the position of the athletic equipment in three-dimensional space. The evaluation device may also include a radio for wireless transmissions, a battery, and a sound tube connected to the microphone. The evaluation device can be used in conjunction with a host computer to store, and display data gathered by the evaluation device. In some methods, a stroke that is detected from a swing and a ball strike can be determined by comparing signals received from the accelerometer and the microphone to predetermined criteria.

SUMMARY OF THE INVENTION

The present invention relates to apparatuses and methods for golf training, and more particularly golf alignment training. The present invention includes a device, attachable to a golf club, for measuring a golfer's alignment by a plurality of sensors, including a magnetometer, during play on a golf course. Additionally, the present invention includes a connected, location-aware device for selecting an intended target line that compares the actual alignment measured by the device with an intended target line. The present invention employs sensors, to measure the golfer's actual alignment (i.e., the face angle of the golf club at address of the ball prior to a swing of the club and strike of the ball), and a location aware device capable of receiving a selection of an intended target line in order to compare the actual alignment with the intended target line.

It is an object of this invention to provide an apparatus and method for golf alignment training.

In one embodiment, the present invention includes a tag device attachable to a golf club for measuring characteristics of a golf swing, including an inertial measurement unit comprising a plurality of sensors, including at least a magnetometer, wherein the plurality of sensors are each configured to output a signal based on a detected condition, movement or orientation of the tag device, a microcontroller including a microprocessor, a memory in communication with the microcontroller and the inertial measurement unit, a transceiver configured to transmit data corresponding to sensor outputs from the plurality of sensors to a remote computing device, and a battery; a connected location aware device comprising a location aware unit, such as, for example, a GPS unit, a microcontroller including a microprocessor, a memory in communication with the microcontroller, a communications unit to send and receive signals from the tag device, a display, an input device to input a selected or intended target, and a battery, wherein the location aware device is configured to receive the actual club alignment from the tag device and make a comparison of the actual alignment to the intended target line.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 8C illustrates a BLE protocol of a preferred embodiment of the present invention.

FIG. 10A illustrates a power state protocol for sensors monitored by an IMU in a preferred embodiment of the present invention.

FIG. 10B illustrates a power state protocol for sensors monitored by a microcontroller in a preferred embodiment of the present invention.

DETAILED DESCRIPTION

Figure 1A:
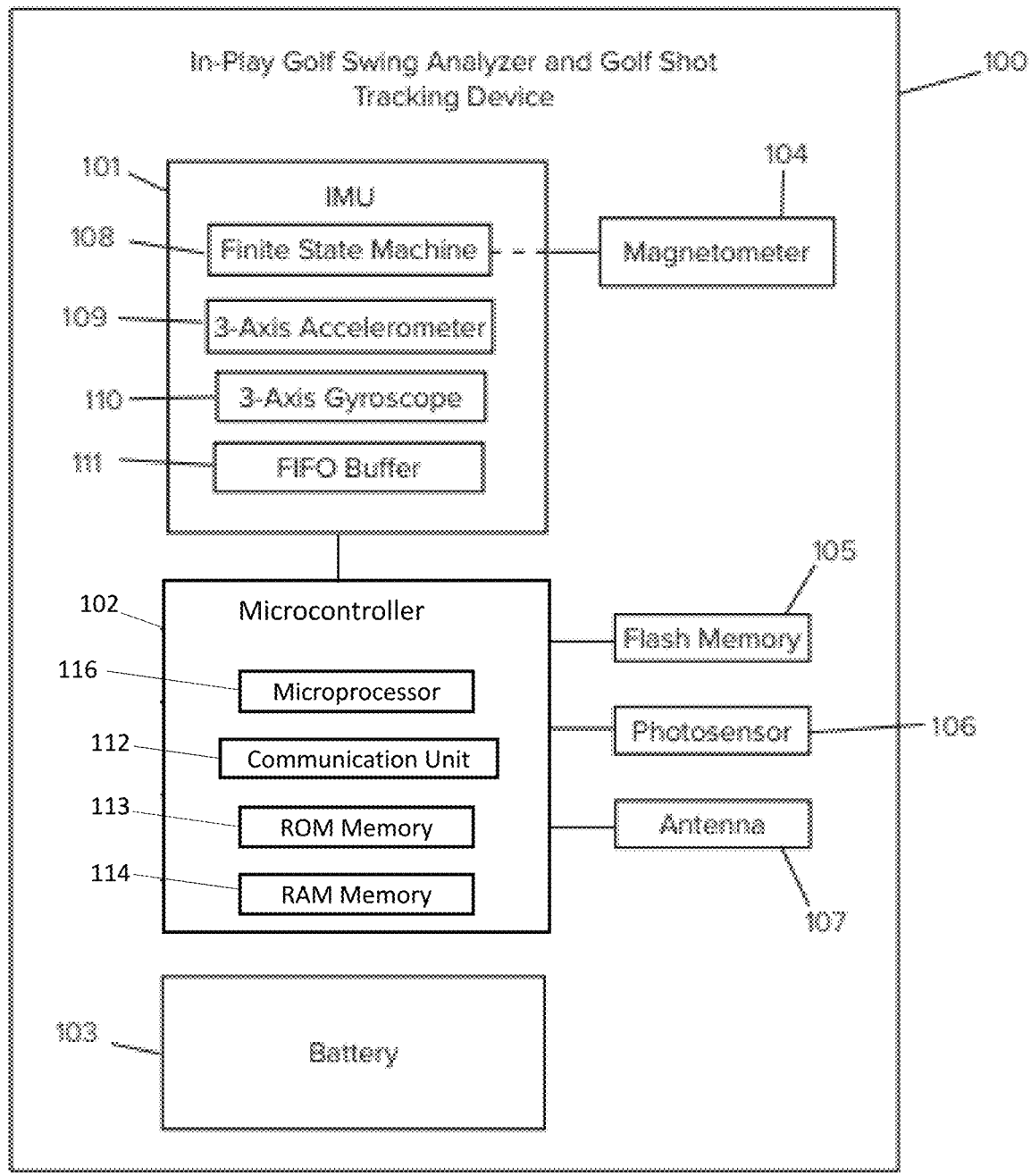
FIG. 1A illustrates a block diagram of the electronic architecture of the tag device according to one embodiment of the present invention.

The present invention is generally directed to apparatuses and methods for analyzing golf swings—particularly the golfer's alignment—through a device with a plurality of sensors, at least one of which is a magnetometer, that measures a golfer's actual alignment and compares the actual alignment to a selected intended target line.

In one embodiment, the present invention includes a tag device attachable to a golf club for measuring characteristics of a golf swing, including an inertial measurement unit comprising a plurality of sensors, including at least a magnetometer, wherein the plurality of sensors are each configured to output a signal based on a detected condition, movement or orientation of the tag device, a microcontroller including a microprocessor, a memory in communication with the microcontroller and the inertial measurement unit, a transceiver configured to transmit data corresponding to sensor outputs from the plurality of sensors to a remote computing device, and a battery; a connected location aware device comprising a location aware unit, such as, for example, a GPS unit, a microcontroller including a microprocessor, a memory in communication with the microcontroller, a communications unit to send and receive signals from the tag device, a display, an input device to input a selected or intended target, and a battery, wherein the location aware device is configured to receive the actual club alignment from the tag device and make a comparison of the actual alignment to the intended target line.

As used throughout, reference to a "finite state machine" is not limited to a stand-alone component but also permits an inertial measurement unit or other sensor or component that includes on-board finite state machine logic.

Golf is a club-and-ball sport in which players use a variety of golf clubs to strike golf balls across a golf course in an attempt to reach a series of holes on the course in as few strokes as possible. Golf is an incredibly popular game that has developed an increasingly competitive community. Golf communities and golf players pride themselves on reducing their strokes per hole, which is the center focus of the game.

Therefore, there is a wide market for devices, techniques, systems, and classes to increase one's golfing skills and reduce their strokes per game. In order to become a more proficient golfer, golfers must understand the intricacies of their golf stroke. In order to better understand one's golf stroke, computer devices have been implemented to measure the parameters associated with one's golf swing. Devices that measure the angle, speed, acceleration, contact point, and orientation of one's golf swing are often used to analyze a golfer's performance, which is used to better one's golf play.

In golf, it is beneficial to track a golfer's shots made on the golf course during a round of play. Much more than just for purposes of scoring, knowing how far and where a golfer hits each shot, along with the club used to make each shot, helps the golfer improve his play and provides an entertaining look back at his round. In order to accomplish this, tag devices are attached to golf clubs that work in conjunction with GPS-enabled mobile devices to monitor and track a golfer's performance and shot location. This is accomplished by taking the geo-location data of each golf shot and calculating the distance between them, which can be overlayed onto a graphical representation of the golf course being played. This process is repeated until the hole is played out.

Conventional tag devices have several shortcomings, including: requiring intervention by the golfer during play; producing sensor data that was based on an invalid swing (i.e., a practice swing or a miss); providing no or limited information about the characteristics of the golf swing; only providing information of the geo-location of each golf shot; insufficient battery life due to high power demands of the tag device; and a short life of the tag devices due to batteries not being replaceable or rechargeable.

Conventional devices also include single-club training devices that employ sensors attached to a golf club to provide a re-creation and analysis of a golfer's swing. Illustrative of such devices are the SKYPRO® swing analyzer by SkyHawke Technologies, LLC. While these devices provide a 3-D depiction of a golfer's swing, they use conventional systems that are too expensive and impractical to attach to each golf club. Furthermore, these devices employ systems that are large, require rechargeable batteries, and have high-power demands. These factors make it impractical or impossible for use on a golf course and further impractical when prior art devices are attempted to be used in connection with the plurality of golf clubs conventionally utilized during a golf game. While a golfer could move the device from one club to another during play, this would require a significant amount of intervention and would slow play, which is an important consideration in a game that takes an average of four hours to complete. More importantly, these limitations impose significant alignment issues because the device must be precisely aligned on the club and re-calibrated each time the device is moved. Due to each of these limitations, these devices are sold as a single unit (i.e., only one for a whole set of golf clubs) where a golfer hits multiple shots with one club before moving the device to another club and re-calibrating it.

What is needed is a sensor-based device that can practically be placed on each of a golfer's clubs to detect and record shots without needing to be removed from a club and placed on another club when a golfer switches clubs. Additionally, it would be useful for a tag device to be of a weight and form that does not interfere with the golfer's swing, provides data associated with the characteristics of the golf swing itself, and is placed at the butt end of the golf club to minimize dislodging or misaligning the tag device when the golf club is placed in a golf bag containing other golf clubs.

However, one problem is that such a device needs to be located on or affixed to the actual golf club in order to capture the swing data accurately, which often interferes with the golfer's swing. Another problem occurs in that tag devices consume a significant amount of power and either require larger batteries to function or do not have the battery life needed to complete a full round of golf. This is counter to the purpose of such data capture devices. Therefore, manufacturers of golf swing data capture devices must balance the needs of creating a sophisticated device with a plurality of sensors that also maintain a small and lightweight form and figure. This problem grows in complexity as golfers require more data about their golf swings while requiring less interference with their golf swings. Otherwise, the device intended to analyze one's golf swing in order to perfect it would actually interfere with one's golf swing.

There are many factors that contribute to the weight and size of a golf swing data capture device (called tag devices). Much of the size and form factor is related to the weight and size of the individual components of the device. One of the largest components required by these devices is the battery. Most golf courses consist of eighteen holes, of which at least nine are usually played at once. Accordingly, a round of golf often lasts at least several hours and therefore requires a tag device with significant charge. If a tag device runs out of battery during play, valuable data about a golfer's performance is not captured and a golfer cannot learn from their mistakes or successes on the course. This is a particularly disappointing situation if the round was notably successful (e.g., it resulted in a hole-in-one). Therefore, a long battery life is greatly desired. However, increasing the size of the battery typically comes at the cost of increasing the weight of the device, thereby affecting the golf swing more, especially if a golfer switches between a club which has a tag device adding noticeable extra weight to the device and another club. As an alternative, it is desirable to optimize the battery life of the device such that it is able to function throughout the entire eighteen-hole endeavor.

Furthermore, it is increasingly beneficial to have a tag device attached to the butt end of a golf club and to be as small and lightweight as possible. The addition of just a few grams in weight to the end of a golf club increases the swing weight by an additional 1 to 2 points, which affects the feel and performance of the golf club. This negatively affects the golfer's performance. Swing weight, shaft stiffness, and golf club profile determine how and where the golf club transitions from the backswing to the downswing, how the shaft loads, and where the golf club will bottom out during the swing. These are all factors that affect a golfer's performance, and lead to the importance of crafting a device that interferes the least with the aforementioned factors. Additionally, placing the tag device at the butt end of the golf club, rather than along the shaft of the club, such as in prior art devices like the SKYPRO, minimizes the possibility that the tag device will be displaced or become misaligned as the club is put into a golf bag containing other clubs or as other clubs are put in a golf bag containing clubs with a tag device.

Another problem with conventional devices is that while they are able to measure a golfer's actual alignment, which is the face angle of the golf club when the golfer addresses the ball ready to strike the ball, they cannot compare the golfer's actual alignment to their intended alignment, sometimes referred to as the intended target line. One of the most common errors golfers make is that their actual alignment does not match their intended alignment. One reason golfers make this common mistake is that when the golfer addresses the ball, they are standing to the side of the ball facing perpendicular to the intended target line and not directly in the intended target line. Thus, the golfer does not have a clear view of their actual alignment relative to their intended target line. This unrealized misalignment has two effects. One, the golfer's shot after hitting the ball is off the intended target. Second, because the golfer is unaware that their actual alignment does not match their intended alignment, the golfer is given the impression that their shot is off target due to some other swing flaw and not the flaw in their alignment. This makes it difficult to correct their swing.

What is needed is an apparatus and method that permits the golfer to input and save their intended target line, measure the golfer's actual alignment, and then compare the intended target line with the actual alignment.

The present invention solves the alignment problem through use of a golf tag employing sensors, at least one of which is a magnetometer, to measure a golfer's actual alignment relative to magnetic north and then comparing the golfer's actual alignment with an intended target line relative to true north that is corrected to magnetic north which has been selected on a connected location aware device.

The present invention is directed to systems and methods for a device operable to analyze characteristics associated with a golf swing during golf play on a golf course. The present invention is directed to a multifunctional golf swing capture and analysis device, "Supertag," or "tag device."

The present invention is further directed to a device that implements a power saving mechanism that functions to reduce the processing power needs of the device, resulting in an extended battery life. While the prior art devices include devices employing sensors to control power management circuitry to reduce or eliminate power supplied from the battery to the various components of the tag, or to place the device into low or high power modes, when the tag is not in use or play or is in a certain condition, position or orientation, these prior art devices deploy high-power consuming microcontrollers with microprocessors to monitor the sensors and/or for motion tracking or shot detection, thus consuming excessive energy. The power saving mechanisms of the present invention are operable to eliminate, reduce, or normalize processing power to a plurality of sensors and components at specific times in order to achieve the desired result of data capture while optimizing battery life. This is accomplished by moving initial management of sensors from the microcontroller to a finite state machine within an inertial measurement unit and using finite state machine logic to limit sensor use until very near the moment the sensor is needed for data capture. The finite state machine logic allows classification of motion data based on known patterns, such as pre-determined thresholds or reference values, and relieves the high-power consuming microprocessor from the task of initial motion tracking or shot detection, thus saving energy. This is further accomplished by implementing BLE protocols that reduce the processing power needed to transmit sensor data without using "pairing" methods traditionally employed by BLUETOOTH-enabled devices.

In the preferred embodiment of the present invention, the tag device is comprised of a printed circuit board (PCB) mounted in a case attached to the end of a golf club grip, mounted within a golf club grip, or attached to the end of and mounted partially within a golf club grip. In one embodiment, the printed circuit board includes, but is not limited to, one, multiple, all, or a specific combination of the following sensors and components: photosensor, accelerometer, gyroscope, and a magnetometer. In one embodiment, the printed circuit board further includes or is connected with at least one shock sensor, operable to detect a shock to (or quick impact with) the tag device. In one embodiment, the printed circuit includes, or is connected with, at least one position sensor, configured to detect a position of the device.

In one embodiment, the tag device includes an accelerometer, operable to determine acceleration along a vector in x, y, and z directions. In one embodiment, the accelerometer is a 3-axis accelerometer. In one embodiment, one, various, or all axes are utilized. In one embodiment, the accelerometer is operable at approximately 1.6 Hz. In one embodiment, the accelerometer is a 3D configurable state accelerometer operable to measure linear acceleration and/or tilt. In the preferred embodiment, the accelerometer is operable to measure the speed, acceleration, and/or tilt of the device in three axes. In one embodiment, the accelerometer is operable for activity and motion detection. In one embodiment, the accelerometer is operable for wake up, tap, and double tap logic.

In one embodiment, the accelerometer is operable to determine the device's (and in turn the golf club's) orientation for data collection. In one embodiment, an algorithm uses accelerometer data to determine the orientation of the golf club and/or, by extrapolation, the golfer's hands. In one embodiment, the algorithm is executed on the accelerometer and/or the IMU. In one embodiment, a neural network analyzes sensor data to determine the golf club and/or, by extrapolation, the golfer's hand orientation. In one embodiment, the algorithm analysis is performed on an onboard CPU core located on the motion sensor itself.

In one embodiment, the IMU is operable to determine when a golf swing is going to occur, has occurred, and/or is occurring and thus save power by only sending sensor data to the microcontroller when a valid golf swing has been determined (i.e., not a practice swing or other golf club movement). In one embodiment, the IMU is operable to detect a golf swing using sensor data stored on the sensor itself, processing the sensor data on the sensor itself, and have the microcontroller exclusively process sensor data after a valid golf swing has been determined. In one embodiment, the microcontroller is in a low power mode prior to detecting a valid golf swing.

In one embodiment, the tag device includes a gyroscope, operable to determine or maintain rotational motion. In one embodiment, the gyroscope is operable to determine the degrees per second of rotation about an axis in the x, y, and/or z orientations. In one embodiment, one, various, or all axes are utilized. In one embodiment, the gyroscope is a 3-axis gyroscope. In the preferred embodiment, the gyroscope is operable to provide data regarding the location and orientation of the inertial measurement unit (IMU) of the tag device.

In one embodiment, the tag device includes a magnetometer and/or a digital compass, operable to determine device orientation to the earth's magnetic field. In one embodiment, the magnetometer is a monolithic integrated 3-axis magnetic sensor. In one embodiment, the magnetometer is operable to measure the strength and/or direction of magnetic fields. In the preferred embodiment, the magnetometer is operable to sense the position and/or orientation of the device in relation to the earth's magnetic field. In one embodiment, the magnetometer is operable to determine the intended bearing to target and/or the actual bearing to target of a golfer's swing.

In one embodiment, the tag device includes a light sensor, operable to detect light levels in an environment. In one embodiment, the light sensor is operable to determine wake up states for the device. In one embodiment, the light sensor is operable at a lower current draw of approximately 1 µA. In one embodiment, the light sensor is a photosensor, operable to detect a light, dark, or dim environment of the device.

In one embodiment, the tag device includes a microcontroller, operable to integrate data from the aforementioned components for onboard processing and/or transmission. In one embodiment, the microcontroller is operable to transmit data via BLE protocols. In one embodiment, the microcontroller is an ultra-low power system on a chip (SoC).

In one embodiment, the tag device includes a microprocessor, operable to receive communications from the plurality of sensors and instruct or initiate the device to transition power states. In one embodiment, the microprocessor is included in the microcontroller. In one embodiment, the microprocessor is operable to receive sensor data from the plurality of sensors and further process that data. In one embodiment, the microprocessor is operable to process the plurality of sensor data to determine the light environment, movement, acceleration, and/or orientation of the device. In one embodiment, the microprocessor is operable to determine when a predetermined threshold of light, movement, acceleration, and/or orientation is sensed by the plurality of sensors to warrant a transition from one power state to another. In one embodiment, the microprocessor is operable to instruct the IMU to transition from one power state to another. In one embodiment, the microprocessor is operable to retrieve power state instructions from the flash memory unit. In the preferred embodiment, the microprocessor is operable to receive notification from the finite state machine and/or the IMU that stored reference values measured by the plurality of sensors have been exceeded and to instruct the flash memory unit to reload the IMU registers to transition the device from one power state to another. In one embodiment, the microprocessor is operable to send power state instructions to the IMU. In one embodiment, the microprocessor is operable to send power state instructions to the finite state machine. In one embodiment, the microprocessor is operable to transition the device from one power state to another. In one embodiment, the microprocessor is operable to instruct the plurality of sensors to operate at a lower, higher, and/or same power level. In one embodiment, the microprocessor is operable to communicate with the battery and instruct the battery to provide a lower, higher, and/or constant power level to the plurality of sensors. In one embodiment, the microprocessor is operable to conduct the functionality of the flash memory unit.

In one embodiment, the tag device includes a memory unit, operable to store the microcontroller's firmware, sensor data, and identification data. In one embodiment, the memory unit includes a read-only memory (ROM) memory unit, a random-access memory (RAM) memory unit, and/or a flash memory unit.

In one embodiment, the tag device includes a BLE radio, operable to transmit sensor data, receive data from a paired device, and/or transfer data to an interfacing device. It should be understood that while BLE is used in the preferred embodiment of the invention, other suitable RF or other communication technologies and/or protocols known in the art are also able to be utilized. In one embodiment, the BLE is operable to identify, calibrate, fingerprint, hash, and/or update tag devices, tags, and/or sensors. In one embodiment the BLE is operable to advertise at a minimum rate, an active rate, and/or an aggressive rate depending on the device's power state or changes the device's power state.

In one embodiment, the tag device includes a piezo sensor, operable to measure changes in pressure, acceleration, temperatures, strain, and/or force. In one embodiment, the piezo sensor is operable to convert changes in pressure, acceleration, temperature, strain, and/or force into an electrical charge. In one embodiment, the piezo sensor acts as a shock sensor. A tilt sensor, operable to detect orientation and/or inclination of the device in three axes.

In one embodiment, the tag device includes a battery, operable to power the sensors, components, and/or the device. In one embodiment, the battery is a lithium-ion, and/or any other suitable battery known in the art. In one embodiment, the battery is a rechargeable battery. In one embodiment, the battery is an energy harvesting circuit comprising a super capacitor, piezo, Peltier, solar cell, and/or other similar energy harvesting device known in the art. In one embodiment, the battery is a CR2032 battery. In one embodiment, the battery is a compact, high energy, lightweight battery. In one embodiment, the battery is operable at different power states.

Furthermore, each tag device is assigned a unique electronic serial number (ESN) or identification (ID) number, which is referred to as a fingerprint, hash, or unique identifier. In one embodiment, each individual component and/or sensor contains an ESN or ID. In one embodiment, each individual golf club contains a unique ESN or ID. In the preferred embodiment, the ESN or ID is transmitted along with the respective sensor and/or component data. In one embodiment, the ESN or ID is associated with a golf club description (e.g., driver, 9-iron, etc.). In one embodiment, the ESN or ID is on a connected device and/or written into the sensor and/or components onboard memory.

In one embodiment, the PCB, its components, and the battery are contained in a ruggedized plastic and/or composite case. In one embodiment, the ruggedized plastic and/or composite case is securely mounted to the end of a golf club grip, mounted within a golf club grip, or attached to the end of and mounted partially within a golf club grip or shaft. In one embodiment, the ruggedized plastics and/or composite case is securely mounted to the shaft of the club.

In one embodiment, the system is operable to measure and calculate various characteristics of a golfers' swing, map the location of the golf swings, visualize data associated with the golf swing, transmit and/or communicate sensor data with display, mobile, and/or interface devices, function in a plurality of power saving states, and/or utilize a plurality of communication protocols. In one embodiment, the system is operable to determine the relative position of the golf club through GPS and/or geolocation data.

In one embodiment, the tag device is operable to determine if the golf club is positioned inside or outside of a golf bag. If the golf club is determined to be outside the golf bag, the tag device is operable to enter a state of waiting. The state of waiting is operable to anticipate and measure data associated with a golf swing, associate the golf swing data with a golf club ESN or ID, and conserve battery power.

More specifically, once a threshold amount of motion associated with the golf club is measured by the sensors and/or components (e.g., accelerometer, gyroscope, and/or magnetometer), the golf club is determined to be engaged in a golf swing, and the device captures various characteristics of the golf swing. In one embodiment, the device is operable to capture a plurality of characteristics of a golf swing selected from among a swing plane, swing tempo, swing velocity, swing force, impact force, club face angle, club face orientation, club head speed, point of ball impact, club face orientation, club head speed, clubhead loft, club lean, hand speed, velocity of a golf club, a trajectory of the golf, ball, angle of impact between the golf club and the golf ball, a face angle of the golf club at impact with the golf ball, a club path during a golf swing, and/or other characteristics. In one embodiment, the swing data is stored in onboard memory and/or relayed via BLE to other devices via communication protocols for storage, application processing, and/or relayed to web-based systems.

In one embodiment, the tag device is associated with or in communication with a device (sometimes referred to herein as a remote or connected computing device, a connected device, or a display device, whether or not the device contains a display) that contains a GPS unit (e.g., a SKY-CADDIE GPS rangefinder, a smartphone running golf rangefinder, or other golf-related GPS programs, or other GPS-enabled devices). In this embodiment, the connected device contains a display and is operable to display the golf related data captured by the tag device and further processed by the connected device. In this embodiment, the golf swing data is associated with geophysical information (e.g., time stamp, latitude, longitude). In this embodiment, the golf swing data and geophysical information is overlayed on to a golf course imagery to show the golfer in real time and/or as a post round analysis. In this embodiment, the golf swing data and geophysical information displays the location and dynamics of the golf shot at the particular time and the particular location on a golf course. In one embodiment, the connected device does not contain a display but captures the tag device data for later transfer to, and post-round display and/or processing on, a device such as a computer or tablet or mobile device with a display.

In one embodiment, the tag device's microcontroller firmware is comprised of code that runs on the microcontroller to handle the microcontroller's startup, wake up, power management, sensor control, sensor data, and BLE (or similar communication protocol). In one embodiment, the sensor data captured by the tag device is transmitted to the display device for logging, processing, and displaying golf shot data and/or the golf swing profile. In this embodiment, a plurality of the ball strike locations, ball landing locations, graphical vector data, intended bearing to target, and actual bearing to target are displayed on the display device and overlayed onto imagery of the golf course being played to visualize the characteristics of the golf swing on the display device. Furthermore, in this embodiment the software of the display device contains a physics engine, as described in more detail below, that analyzes the sensor data received from the tag device to create an animated 3D profile to visualize the golf swing, ball strike, and/or golf swing follow through.

In one embodiment, the tag device is operable to time stamp golf swings. In this embodiment, the tag device contains a clock unit to timestamp each swing that represents a golf shot. In one embodiment, the tag device initially and periodically synchs the time of the tag device with the time of the display device. When a swing is detected by the tag device, the swing is timestamped so the display device containing GPS capability associates the timestamped swing, and hence the shot, with the location of the display device at that time, which is a proxy for the shot location. In another embodiment, the tag device, to save battery life and space, does not contain a clock unit. Instead, when the tag device transmits golf swing data to the display device, the display device automatically generates metadata including a timestamp indicating the time at which the golf swing data was received, and the display device containing GPS capability associates the swing, and hence the shot, with the location of the display device at that time, which is a proxy for the shot location.

As noted, the tag device measures the motion path of a golf club, particularly the club face alignment from at least the address of the ball. Examples of tag devices included herein as exemplary embodiments are nonlimiting. The present invention may be used in combination with any tag device capable of measuring sufficient swing parameters of a golf club to generate the club face alignment from at least address of the ball, which are well known to those skilled in the art. Examples of a tag device with which the present invention may be combined include, but are not limited to, the tag devices which are described in U.S. patent application Ser. No. 13/744,294 and U.S. Pat. Nos. 8,998,717 and 8,905,856, each of which is incorporated herein by reference in its entirety. Those skilled in the art will recognize that these are only examples of the several tag devices currently available. The present invention is not intended to be restricted to any particular type of tag device which captures the motion path of a golf club, including the club face alignment, and the present invention is capable of being used in combination with any tag devices having those desired characteristics.

In one embodiment, the tag device can be in a dark power state, an inactive power state, an active power state, a data collection power state, and/or a streaming power state, in which selection of the sensors receiving power is dependent on the then current state of the tag device. In one embodiment, the dark power state describes a power state where little to no battery power is provided to the plurality of sensors. In one embodiment, the dark power state provides battery power only to the photosensor. In one embodiment, the inactive power state describes a power state where power is provided to the plurality of sensors. In one embodiment, the inactive power state only provides power to the plurality of sensors for a limited, pre-determined time based on the activity sensed by the plurality of sensors. In the preferred embodiment, in the inactive power state, power is only provided to the light sensor, low power to the accelerometer, which cycles at a reduced cycle rate, and to the BLE in accordance with a predetermined BLE protocol. In one embodiment, the inactive power state describes an intermediate power state that is activated when the tag device has exited the dark power state but does not have sufficient sensor parameters to enter an active power state. In one embodiment, the active power state describes a state where power is provided to the plurality of sensors and the plurality of sensors are configured to collect and measure swing data. In the preferred embodiment, in the active power state, power is provided to the photosensor, increased power the accelerometer which cycles at a higher cycle rate than in the inactive state, and to the BLE in accordance with a predetermined BLE protocol. In one embodiment, the active power state is activated where the tag device is determined to be in motion and under parameters where the golf club is not positioned for a swing. In one embodiment, the data collection power state describes a state where power is provided to the plurality of sensors and the plurality of sensors are actively collecting and measuring swing data. In the preferred embodiment, in the data collection state, power is provided to the photosensor, the accelerometer operating at the higher cycle rate, the gyroscope, the BLE in accordance with a predetermined BLE protocol, and the magnetometer. In one embodiment, the data collection power state is activated when a golf club is placed in a position for a swing to occur and a ball strike is anticipated to occur. In one embodiment, the streaming power state describes a state where power is provided to the plurality of sensors, including, at least, the BLE, and the data collected from the plurality of sensors is being streamed to an interfacing or display device. In one embodiment, the streaming power state is activated when swing data has been collected and is being streamed to a display device. In the preferred embodiment, the data streaming state is activated after data has been collected on a swing in the data collection state, the tag device is aggressively advertising through its Bluetooth BLE communications, and an associated display device has issued a call to the tag device for the collected data. In one embodiment, the BLE is aggressively advertising regardless of the current power state.

The plurality of power states described encompass a finite state machine logic utilized by the tag device in order to maximize battery life. The plurality of power states functions to extend the battery life of the tag device by utilizing the plurality of sensors only to the extent needed to capture swing data. Effectively, the plurality of power states are operable to activate a sensor just before and/or as they are needed to collect sensor data. By limiting processing power to the plurality of sensors as much as possible, without sacrificing data collection, the tag device uses less processing power to complete its function, which allows the tag device to avoid using a large battery, which allows the tag device to remain in a small and lightweight form as to not interfere with a golf swing. The plurality of power states solves the issue presented by devices that capture and measure data associated with a golfer's swing. The plurality of power states helps to balance the countervailing needs of a data capture device—functionality and accuracy of data collection versus a small, lightweight device that does not interfere with a golf swing. While various embodiments described herein are described as having power states selected from among a dark power state, an inactive power state, an active power state, a data collection power state, and/or a streaming power state, one of ordinary skill in the art will appreciate that the power states are able to have different nomenclatures, greater or fewer power states are contemplated, and the various states described herein are simply meant to describe power states using finite state machine logic ranging from a lowest power state to a highest power state.

In the preferred embodiment, the tag device includes a photosensor, an accelerometer, a gyroscope, a magnetometer, and BLE communication. The preferred embodiment is able to exist in a dark power state, an inactive power state, an active power state, a data collection power state, or a streaming power state. In the dark state, the photosensor is the only sensor that receives power. When the photosensor measures light exceeding the pre-determined light threshold, the device transitions to the inactive state. In the inactive state, the photosensor continues to receive power, the accelerometer receives power sufficient to power the accelerometer at a reduced cycle rate, and the BLE is powered in accordance with a predetermined BLE protocol. When the photosensor measures light exceeding the pre-determined light threshold and the accelerometer measures movement of the device exceeding the pre-determined movement threshold, the device transitions to the active state. In the active state, the photosensor continues to receive power, the accelerometer increases its cycle rate and receives power sufficient for the increased cycling rate, and the BLE is powered in accordance with a predetermined BLE protocol. When the photosensor measures light exceeding the light threshold and the accelerometer measures movement exceeding a pre-determined threshold that suggests the club has been orientated into an upright position indicative that the club is ready to be swung, the device transitions into the data collection state. In the data collection state, the photosensor continues to receive power, the accelerometer continues to receive power at the increased cycle rate, the gyroscope is powered, the magnetometer is powered, and the BLE is powered in accordance with a predetermined BLE protocol. Once a golf shot is detected in the data collection state, the shot is stored in the memory of the tag device, and the BLE begins to aggressively advertise to the connected display device that a shot has been stored. Once that BLE communication is received by the connected device, the connected device sends a call to the tag device to transmit the stored shot data to the connected device. Upon receiving the call from the connected device, the tag device enters the streaming state in which the data stored in the memory of the tag device is transmitted to the connected display device.

Referring now to the drawings in general, the illustrations are for the purpose of describing one or more preferred embodiments of the invention and are not intended to limit the invention thereto.

FIG. 1 illustrates a block diagram of the electronic architecture of the tag device 100 according to one embodiment of the present invention. In this embodiment, the tag device 100 includes an inertial measurement unit (IMU) 101, a microcontroller 102, a battery 103, a microprocessor 116, a magnetometer 104, a flash memory unit 105, a photosensor 106, and an antenna 107. The IMU 101 includes a finite state machine (FSM) 108, a 3-axis accelerometer 109, a 3-axis gyroscope 110, and a first in first out (FIFO) buffer unit 111. The microcontroller 102 includes a communication unit 112, RAM memory unit 113, a ROM memory unit 114, and a microprocessor 116.

The IMU 101 is a low power, high performance unit with an integrated 3D accelerometer 109, 3D gyroscope 110, finite state machine 108, and FIFO buffer 110. In the preferred embodiment, the IMU 101 is operable to measure the movement, speed, acceleration, and orientation of the device in three dimensions and as referenced to the earth's magnetic field. The IMU 101 is further operable for capturing, storing, and processing sensor data, then transferring the processed sensor data to a microcontroller 102 for transmission via BLE protocols.

In one embodiment, the microcontroller 102 is an ultra-low power system on a chip (SoC) microcontroller that includes communication unit 112, ROM memory 113, RAM memory 114, and the microprocessor 116. The microcontroller 102 is operable to store and execute operational instructions and processes, as well as, temporarily storing processed IMU data and transmitting the processed IMU data via BLE.

In one embodiment, the microprocessor 116 is operable to receive plurality of sensor data from a plurality of sensors. In one embodiment, the microprocessor 116 is operable to determine, based on the plurality of sensor data, when the device 100 is under conditions that warrant transitioning from one power state to another. In one embodiment, the microprocessor 116 is operable to communicate with the flash memory 105. In one embodiment, the microprocessor 116 is operable to receive power state instructions from the flash memory 105 and send the power state instructions to the IMU 101. In one embodiment, the microprocessor 116 is operable to instruct the plurality of sensors in the IMU 101 to operate at a lower, higher, consistent, and/or inactive power level. In one embodiment, the microprocessor 116 is operable to instruct the 3-axis accelerometer 109, 3-axis gyroscope 110, magnetometer 104, and/or photosensor 106 to operate at a lower, higher, consistent, and/or inactive power level. In one embodiment, the microprocessor 116 is operable to instruct the 3-axis accelerometer 109, 3-axis gyroscope 110, magnetometer 104, and/or photosensor 106 to operate in accordance with the power state instructions. In one embodiment, the microprocessor 116 is operable to instruct the 3-axis accelerometer 109, 3-axis gyroscope 110, magnetometer 104, and/or photosensor 106 to operate to transition from one power state functionality to another power state functionality. In one embodiment, the microprocessor 116 is operable to instruct the 3-axis accelerometer 109, 3-axis gyroscope 110, magnetometer 104, and/or photosensor 106 to operate according to a power state protocol. In one embodiment, the microprocessor 116 is operable to instruct the battery 103 to provide power to the 3-axis accelerometer 109, 3-axis gyroscope 110, magnetometer 104, and/or photosensor 106. In one embodiment, the microprocessor 116 is operable to instruct the IMU 101 to operate at a power state, a different power state, and/or the current power state. In one embodiment, the microprocessor 116 is operable to conduct the functionality of the flash memory 105. In one embodiment, the microprocessor 116 is operable to receive notifications from the IMU 101 that stored reference sensor values have been exceeded and to instruct the flash memory 105 to reload the registers of the IMU 101 to transition from one power state to another. In one embodiment, the power state is determined using a finite state machine employing finite state machine logic.

In one embodiment, the microprocessor 116 is operable to determine a pre-swing state, a swing state, and/or an after-swing state of the device 100. In one embodiment, the microprocessor 116 is operable to receive a plurality of sensor data from the 3-axis accelerometer 109 to determine a pre-swing state, a swing state, and/or an after-swing state of the device 100. In one embodiment, the microprocessor 116 is operable to determine an adjusted z-axis orientation of the device 100. In one embodiment, the microprocessor 116 is operable to determine a z-axis orientation of the device 100 that indicates the device 100 is in a pre-swing, swing, and/or after-swing state. In one embodiment, the microprocessor 116 is operable to determine an adjusted z-axis orientation of the device 100 that indicates the device 100 is in a pre-swing, swing, and/or after-swing state. In one embodiment, the microprocessor 116 is operable to calibrate the device 100 to adjust for the swing orientation of a golfer. In one embodiment, the microprocessor 116 is operable to communicate with a neural network to calibrate the device 100 to adjust for the swing orientation of a golfer. In one embodiment, the microprocessor 116 is operable to process a plurality of sensor data from the 3-axis accelerometer 109 to determine when the device 100 is in a pre-swing, swing, and/or after-swing state. In one embodiment, the microprocessor 116 is operable to process a plurality of sensor data from the 3-axis accelerometer 109, adjust for the golfer's swing orientation, and determine when the device 100 is in a pre-swing, swing, and/or after-swing state.

In one embodiment, the plurality of sensor data is stored using a first in, first out que. In one embodiment, the plurality of sensor data is stored on a circular buffer.

In one embodiment, the magnetometer 104 is a monolithic integrated 3-axes device operable to measure the strength and direction of magnetic fields. In a preferred embodiment, the magnetometer 104 is operable to sense the position and orientation of the device 100 in relation to the earth's magnetic field.

In one embodiment, the flash memory unit 105 is a non-volatile, bi-directional memory medium. In the preferred embodiment, the flash memory unit 105 is operable to store specific data pertaining to the calibration and identification of the device and the operational instructions that control input and output operations, and to serve as temporary storage for captured and processed sensor data.

In one embodiment, the photosensor 106 is a photoconductive light sensor that is operable to provide input to the microcontroller 102 for the optimization and limitation of power drawn by the device 100 when located in a dark environment.

In one embodiment, the antenna 107 is a 2.4 GHz RF antenna. In one embodiment the antenna 107 is designed with components to optimize transmission quality and range of BLE data communication between a display device and other BLE enabled devices. In one embodiment, the antenna 107 is a passive channel antenna formed by a channel and backplane of the PCB. This orientation eliminates the need for a separate active antenna chip that would otherwise consume more power. In one embodiment, the antenna 107 utilizes the battery 103 negative surface for the ground plane. Furthermore, this formation provides greater range without consuming additional power that would be required by an active antenna chip. Lastly, this formation saves space on the PCB, allowing the tag device 100 to be smaller and lightweight.

In one embodiment that uses finite state machine logic to determine power states, the finite state machine (FSM) 108 is a subcomponent of the IMU 101, such as, for example, the 6-axis iNEMO IMU by STMICROELETRONICS. The FSM 108 is operable to process data received from the accelerometer 109, the gyroscope 110, and/or the optional magnetometer 104 according to pre-determined FSM logic and algorithms. The FSM 108 is further operable to transfer processed data to the FIFO Buffer 111. As used herein, the term "process" when used in connection with sensor outputs that are managed by, in communication with, or connected to a FSM is intended to mean to implement finite state machine logic using finite state machine processes known to those of ordinary skill in the art. "Process" in this context is not meant to be limited to computer processing but also encompasses any other technique or procedure that implements finite state machine logic.

In one embodiment, the 3-axis accelerometer 109 is a 3D configurable state accelerometer. The 3-axis accelerometer 109 is operable to measure linear acceleration and/or tilt. The 3-axis accelerometer 109 is further operable to measure the speed, acceleration, and/tilt of the device 100 in three axes. The 3-axis accelerometer 109 is further operable to detect activity states, motion states, wake up states, and tap/double tap logic.

In one embodiment, the 3-axis gyroscope 110 is operable to measure motion around an axis, including the angular velocity of the IMU 100 with respect to a given axis. The 3-axis gyroscope 110 is further operable to provide data regarding the location and orientation of the IMU 101.

In one embodiment, the FIFO buffer 110 is a data buffer with data compression capabilities. The FIFO buffer 110 is operable to regulate the flow of processed data to the microcontroller and to the RAM memory unit 114. In a preferred embodiment, the accelerometer, gyroscope, and FIFO buffer are contained in a single module, such as, by non-limiting example, the iNEMO inertial module by STMICROELECTRONICS.

In one embodiment, the communication unit 112 is a Bluetooth transmitted operable to use Bluetooth low energy (BLE) protocols. In one embodiment, the communication unit 112 is operable for communicating with other external devices, such as display device, mobile devices, interfacing devices, and/or tablets. The communication unit 112 is further operable to send and receive signals using BLE protocols. The communication unit 112 is a transmitter operable to communicate with devices using radio waves. Bluetooth is a wireless short-range communication technology.

In one embodiment, the ROM memory unit 113 is a non-volatile, read-only memory unit. The ROM memory unit 113 is operable to store computer readable instruction to be executed by the microcontroller 102. The ROM memory unit 113 is further operable to execute input/output tasks and firmware startup, initialization, and basic operations.

In one embodiment, the RAM memory unit 114 is a bi-directional random access memory unit. The RAM memory unit 114 is operable to temporarily store processed data from the IMU 101 prior to its output from the device via communication unit 112. The RAM memory unit 114 is further operable to temporarily store data received via BLE communication 112 input until processed and distributed by the microcontroller 102. In the preferred embodiment, RAM memory is resident on the BLUETOOTH communications unit, such as by non-limiting example the SMARTBOND TINY BLUETOOTH LOW ENERGY System on a Chip by RENESAS ELECTRONICS CORPORATION.

In one embodiment, the ROM memory unit 113 exclusively contains root instructions for the tag device's startup while the flash memory unit 105 contains operational instructions and power state instructions. In this embodiment, the microcontroller 102 uses less power because the operational instructions and power state instructions are run on the flash memory 105 rather than in a microcontroller 102 environment. In one embodiment, the microprocessor 116 uses less power because the operational and power state instructions are stored on the flash memory 105. This functions to overall reduce the use of the microcontroller, which saves battery power. Furthermore, in this embodiment, the operating instructions are able to be updated by uploading new instructions to the flash memory unit 105, which does not require powering the microcontroller 102.

In one embodiment, the plurality of sensor data is processed by the IMU 101, while the microcontroller 102 manages the communication unit 112 operations. In this embodiment, battery power is saved by reducing the amount of processing power needed by the microcontroller. In one embodiment, in order to accomplish the above stated embodiment, the IMU 101 utilizes a finite state machine 108 and finite state machine logic to process the sensor data.

In one embodiment, the plurality of sensor data is processed by the microprocessor 116. In one embodiment, the IMU 101, the 3-axis accelerometer 109, the 3-axis gyroscope 110, the magnetometer 104, the photosensor 106, and the flash memory 105 are in communication with the microprocessor 116. In one embodiment, the microprocessor 116 is operable to send power state instructions and/or protocols from the flash memory 105 to the IMU 101, the 3-axis accelerometer 109, the 3-axis gyroscope 110, the magnetometer 104, and/or the photosensor 106. In one embodiment, the microprocessor 116 is operable to receive power state instructions from the flash memory 105 in response to receiving a predetermined threshold of sensor data from the IMU 101, the 3-axis accelerometer 109, the 3-axis gyroscope 110, the magnetometer 104, and/or the photosensor 106.

Figure 1B:
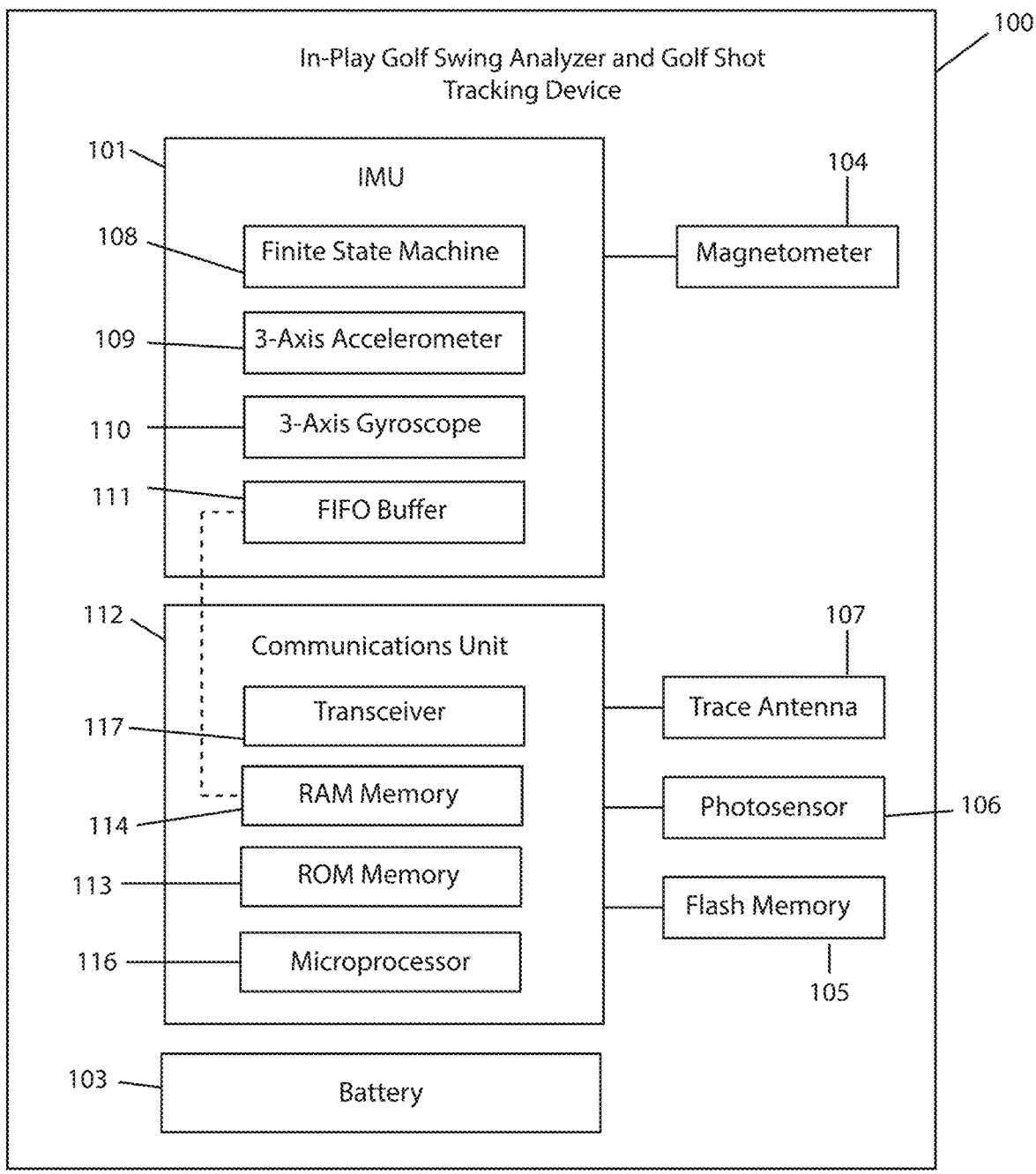
FIG. 1B illustrates a block diagram of the electronic architecture of the tag device according to an alternate embodiment of the present invention.

FIG. 1B illustrates a block diagram of the electronic architecture of the tag device 100 according to an alternate embodiment of the present invention. In this embodiment, the tag device 100 includes an inertial measurement unit 101, a communications unit 112, a battery 103, a magnetometer 104, a flash memory unit 105, a photosensor 106, and an antenna 107. Except as described herein, the inertial measurement unit 101 is as described with respect to FIG. 1A and reference is made thereto. The principal difference between the embodiments illustrated in FIG. 1A and FIG. 1B is that the embodiment illustrated in FIG. 1B utilizes the microprocessor 116 of the communications unit 112 to perform general purpose processing in addition to communications-related processing and does not employ a general purpose microcontroller. In the embodiment described in FIG. 1B, the inertial measurement unit 101 is in communication with the communications unit 112, including the microprocessor 116 of communications unit 112, and the FIFO buffer 111 of the inertial measurement unit 101 is in communication with the RAM memory 114 of the communications unit 112. Additionally, the flash memory 105, the photosensor 106 and the antenna 107 are each in communication with the communications unit 112, including the microprocessor 116. In the embodiment illustrated in FIG. 1B, the antenna 107 is a trace antenna. The communications unit 112 includes a transceiver 117.

Figure 1C:
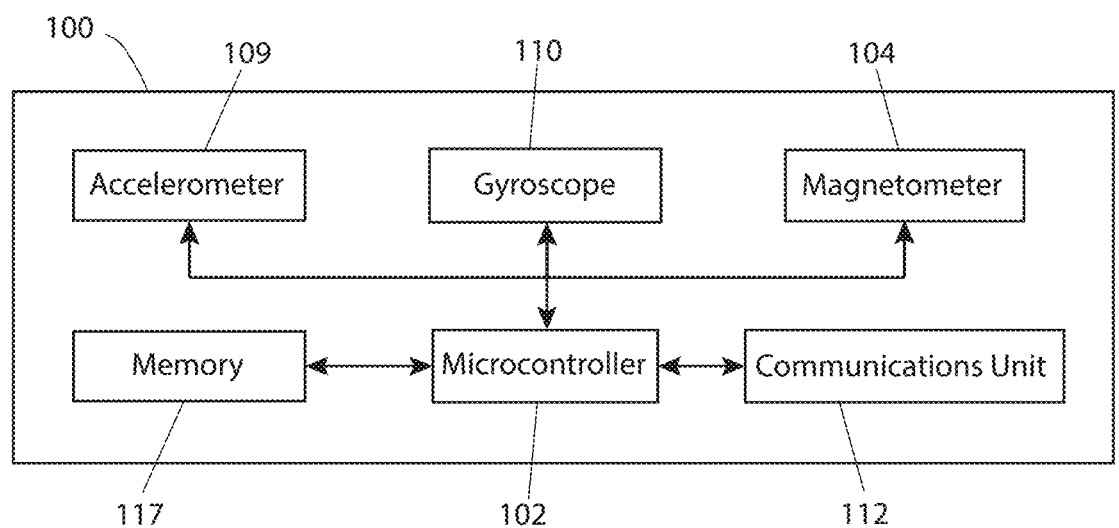
FIG. 1C illustrates a block diagram of the electronic architecture of the tag device according to one embodiment of the present invention.

FIG. 1C illustrates a block diagram of the electronic architecture of the tag device according to one embodiment of the present invention. The tag device unit 100 of FIG. 1C includes a controller 102, a gyroscope 110, an accelerometer 109, a magnetometer 104, a memory 119, and a communications unit 112. The controller 102 is able to be any processor unit capable of executing instructions stored on the memory 119. The gyroscope 110 is a device for measuring motion around an axis, including the angular velocity of the tag device 100 with respect to a given axis. The accelerometer 109 is a device for measuring the angular and/or linear acceleration of the tag device 100 relative to a local inertial frame and able to output the acceleration as a vector quantity including magnitude and orientation. The magnetometer 104 is a device operable to measure the strength and direction of magnetic fields and is further operable to sense the position and orientation of the tag device relative to the earth's magnetic field. The memory 119 is a memory unit including volatile memory, non-volatile memory, flash memory or a combination thereof, and is utilized by the controller 102 for storage during motion analysis and reconstruction processing. The communications unit 112 is a device for communicating with other external devices, such as a smart phone, a connected computing display device, or other devices. The communications unit 112 sends and receives signals using a wireless or wired communications protocol, such as WI-FI, BLUETOOTH, Ethernet, a cellular network, or other suitable network protocols.

Figure 2:
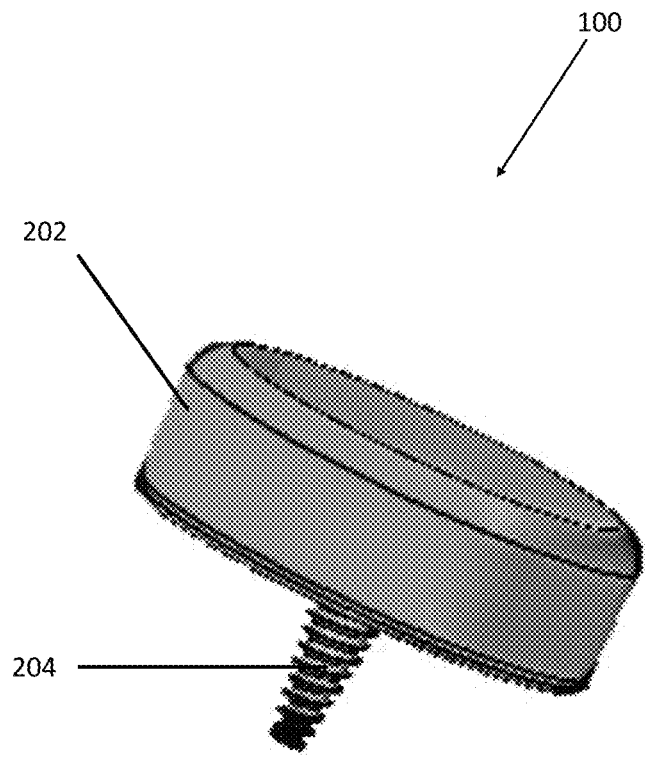
FIG. 2 illustrates a side perspective view of a tag device according to one embodiment of the present invention.

FIG. 2 illustrates a side perspective view of a tag device 100 according to one embodiment of the present invention. In one embodiment, the tag device 100 includes a printed circuit board (not shown), a mounting case 202, and a mounting mechanism 204. In one embodiment, the accelerometer, gyroscope, magnetometer/digital compass, light sensor/photosensor, microcontroller, memory unit, BLE, Piezo sensor, tilt sensor, and battery are contained within the case 202. In one embodiment, the case 202 is a ruggedized plastic and/or composite case. In one embodiment, the mounting mechanism 204 is a threaded, cone shaped screw extending outwardly from a wide base of the case 202, and has a threaded tip on the opposite end similar to a conventional screw. This allows the tag device to be screwed into the top of a golf club handle or butt end of the grip as a means of attachment.

Figure 3:
FIG. 3 illustrates a side perspective view of a tag device placement on a golf club according to one embodiment of the present invention.

FIG. 3 illustrates a side perspective view of a tag device 100 placed on a golf club 300 according to one embodiment of the present invention. In one embodiment, the tag device 100 is mounted to the top of a golf club handle 304. This allows the tag device 100 to capture data associated with a golfer's swing while allowing the golfer to swing without interference by the device. Furthermore, when the tag device 100 is mounted to a golf club 300 it is operable to determine its position in or out of a golf club bag. This is accomplished by the light sensor or photosensor's detection of a dark or light environment. As an example, when a golf club is not in use and placed in a golf bag, normally, the golf club handle is placed downward into the dark environment of the golf club bag. Conversely, when a golf club is taken out of the golf club bag and used the handle to the golf club is exposed to the light environment. Therefore, due to the tag device's 100 position on the golf club 300 the tag device is able to determine whether the golf club is in or out of the golf club bag based on the light intensity and/or the change in light intensity detected by the light sensor.

In one embodiment, the tag device is operable to determine what golf course the golfer is currently playing on and the relative position of the golfer on the golf course (e.g., which hole the golfer is playing) by communicating with at least one GPS-enabled user device. In this embodiment, the determination of the golf course and position is used to overlay the plurality of sensor data onto a virtually rendered map of the golf course (or hole of the golf course) such that a user has a reference point of where each stroke occurs relative to the environment.

Figure 4A:
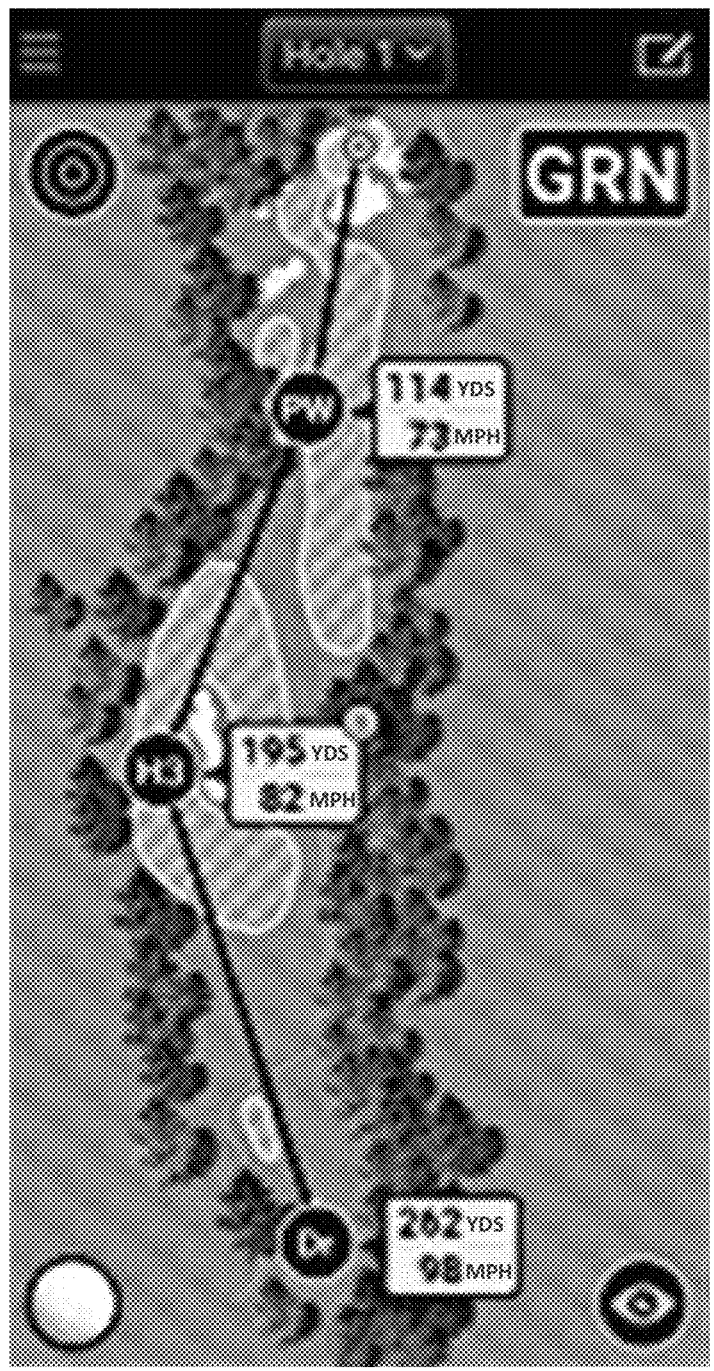
FIG. 4A illustrates an exemplary embodiment of a digital display of a connected computing device showing the tag device's geo-location data according to one embodiment of the present invention.

FIG. 4A illustrates an exemplary embodiment of a digital display of a connected device showing geo-location data according to one embodiment of the present invention. In one embodiment, the geo-location of the golf ball when struck is captured, along with other associated sensor data of the golf swing. In one embodiment, the tag device does not contain GPS-capability. In this embodiment, the connected device is a location-aware device, e.g., a device with GPS capability, and the sensor output data from the tag device corresponding to a ball strike is time stamped. The time stamped tag device sensor data is communicated to the connected device, and an association is made between the sensor data indicating a ball strike and the location of the connected device measured at the time the tag device sensor data was initially collected. After the golfer moves to the landing location of the golf ball, and subsequently strikes the golf ball, the geo-location is captured again. Continuing this process allows the tag device to map out the location of each golf swing as visualized in FIG. 4A. Furthermore, by calculating the distance between golf swings, a determination is also made as to the distance traveled by the golf ball and the location of the golf ball on the golf course of each subsequent golf swing. In one embodiment, geo-located ball strike data is overlaid onto a map of the golf course being played. In one embodiment, the display device visualizes sensor data associated with each golf swing, such as yards traveled and clubhead speed as illustrated in FIG. 4A and FIG. 4B, as well as a 3D rendering of the swing resulting in each shot as illustrated in FIG. 4C.

Figure 4B:
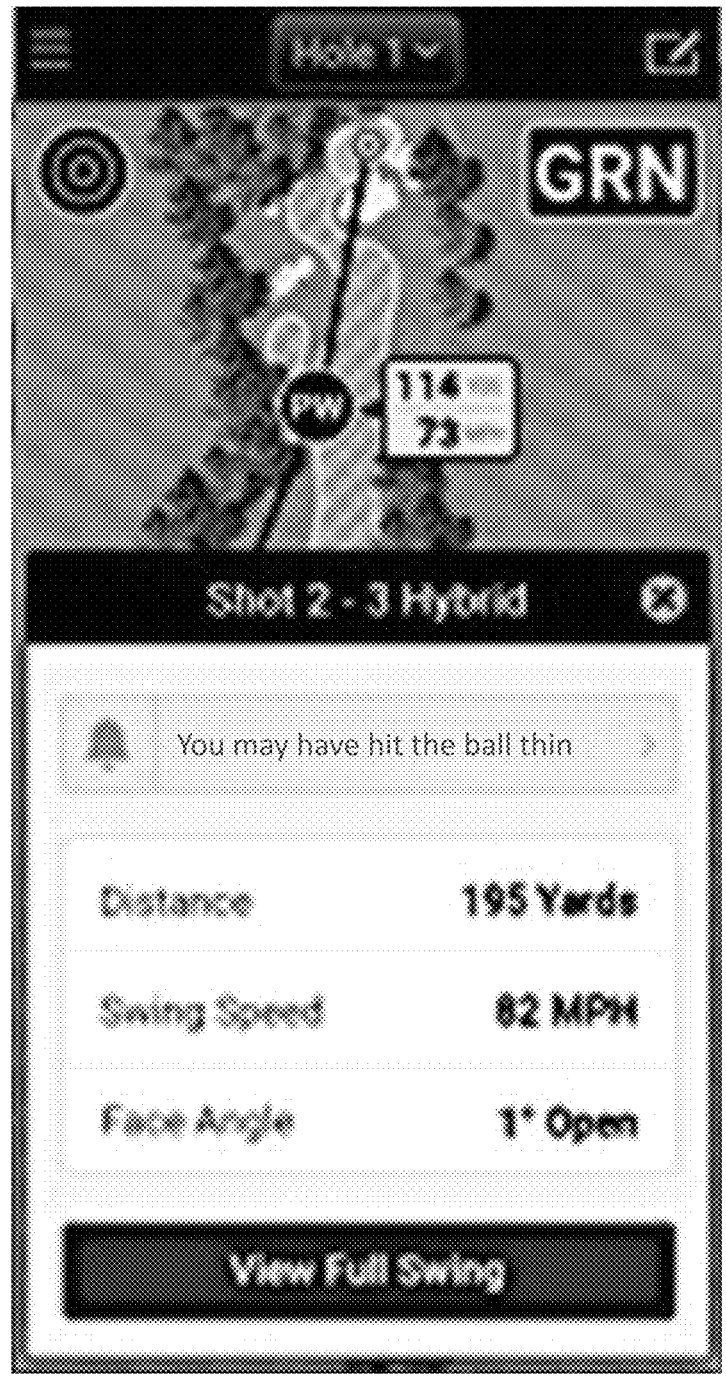
FIG. 4B illustrates an exemplary embodiment of a digital display of a connected computing device showing the tag device's geo-location data and selected sensor data.

FIG. 4B illustrates an exemplary embodiment of a digital display of a connected device showing tag selected sensor data of a swing. In one embodiment, a user is able to select an individual golf swing to pull up an additional display that shows sensor data of a swing (e.g., distance traveled, velocity, face angle, etc.). For instance, the second shot depicted on FIG. 4A is marked with a round shot location marker designated H3, meaning the shot was taken from that location on the hole with the 3 hybrid club. Adjacent to the shot location marker is a callout box with minimal selected data about the shot. In the example shown on FIG. 4A that selected minimal data is the distance the shot traveled, i.e., 195 yards, and the clubhead speed of the shot, i.e., 82 m.p.h. The golfer could retrieve and display on the connected device additional data about the shot by using a user input mechanism on the display device to select the shot. Preferably the display device includes a touch screen. By touching the shot location marker or the adjacent callout box, an additional display is pulled up showing additional shot data. For instance, in the embodiment described in FIG. 4A, in connection with a display device with a touch screen, by touching the callout box depicting the minimal data associated with the second shot using the 3 hybrid club, the display changes to that depicted in FIG. 4B, which displays additional data about the shot. While FIG. 4B displays data with respect to distance of the shot, swing or clubhead speed, and face angle, one skilled in the art will appreciate that other pertinent data collected about the shot is also able to be displayed. Further, the additional shot data screen includes a touch screen "button" for Full Swing.

In one embodiment, the tag device is operable to determine what golf course the golfer is currently playing on and the relative position of the golfer on the golf course (e.g., which hole the golfer is playing) by communicating with at least one GPS-enabled user device. In this embodiment, the determination of the golf course and position is used to overlay the plurality of sensor data onto a virtually rendered map of the golf course (or hole of the golf course) such that a user has a reference point of where each stroke occurs relative to the environment.

Figure 4C:
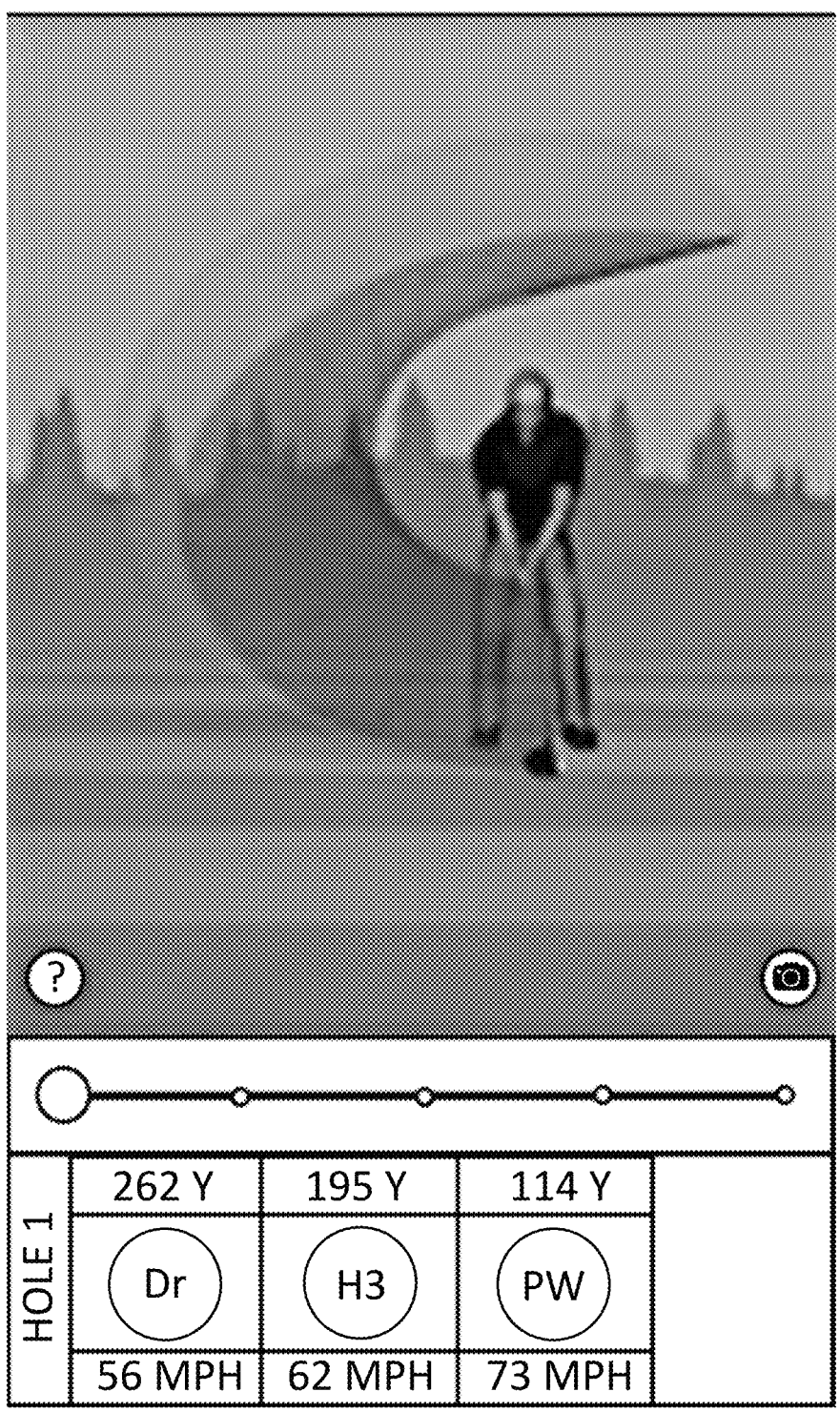
FIG. 4C illustrates an exemplary embodiment of a digital display of a connected computing device showing swing analysis according to one embodiment of the present invention.

FIG. 4C illustrates an exemplary embodiment of a digital display of a connected device showing swing analysis according to one embodiment of the present invention. Referring to FIG. 4B, in one embodiment, the connected GPS-enabled digital display device of the tag device includes a physics engine that analyzes sensor data to create a 3D profile of a golf swing, ball strike, and golf swing follow through. In this embodiment, the connected digital display device includes software (sometimes referred to herein as a "physics engine") to generate a recreation of the motion path of the golf club and display the motion path as a swing of the golf club.

In this embodiment, the tag device is calibrated using properties of motion for a rigid body such that features of the golf club are determined. The calibration is able to determine, e.g., the club's lie, loft, face normal, face angle, and the distance between the tag device and the club head. One method of calibration is described in U.S. Pat. No. 9,395,385 for Method and apparatus for determining a relative orientation of points on a rigid body by inventor Parke, et al, which is incorporated herein by reference in its entirety. After determining the orientation of various points on the golf club relative to the tag device, motion of the golf club in three-dimensional (3D) space is able to be analyzed and reconstructed. For example, in one embodiment, the 3D spatial coordinates of the golf club during a golf swing are determined and translated to a graphical interface such that a golfer is able to visually analyze features of his/her golf swing.

As stated previously, the relative position and orientation of points on a rigid body, i.e., in this case a golf club, relative to the tag device is able to be determined in advance such that features of a golf swing (e.g., swing plane, club head speed, shaft lean) are subsequently derived based on, e.g., a measured angular velocity, angular acceleration, and/or linear acceleration. That is, if the relative position and orientation of the tag device with respect to the golf club is known, then the movement of the golf club is able to be reconstructed using relationships of motion on a rigid body in an inertial plane. In one embodiment, the physics engine software is run on the microcontroller of the connected display device. In another embodiment, the physics engine software is run on a host computer. In the preferred embodiment, the physics engine software is run on the microcontroller of the remote computing device, and the remainder of the discussion of this process will refer to the preferred embodiment and reference to the microcontroller is a reference to the microcontroller of the remote computing device. Once a swing has been detected, the microcontroller receives the raw sensor data, referred to herein as "swing data," output by the selected sensors on the tag device. The swing data includes the raw angular and linear acceleration data, and the rotation data respectively collected by the selected sensors of the tag device over the course of a swing. The swing data is also able to include metadata that is comprised of a time stamp indicating when a swing occurred and the time series corresponding to the measured acceleration and rotation. The microcontroller identifies key swing milestones based on the captured swing data. In one embodiment, swing milestones include, e.g., the point of address (the start of the swing), the top of the backswing, the point of impact with a golf ball, and the end of swing follow through. In one embodiment, the swing milestones are used as reference points for performing subsequent motion analysis and reconstruction processing.

In one embodiment, the swing is reconstructed by the microcontroller, based on the swing data, by calculating the translation and rotation of the golf club. As previously discussed, the swing data includes at least time-stamped angular/linear acceleration and rotation measurements from the selected sensors. These measurements are calibrated and corrected for sensor capping, such that they are translated into meaningful values for swing reconstruction. The microcontroller is able to perform an integration of the acceleration and angular velocity throughout the swing. In the case of determining 3D spatial position, the microcontroller integrates the acceleration once to determine velocity, and then again to determine the position (e.g., coordinates in the x-y-z axes). Similarly, the microcontroller integrates the rotation measurement from, e.g., the gyroscope, in the swing data once to determine the angular position. In one embodiment, once these translations of the swing data are performed, a reconstruction of the swing is performed such that the swing is able to be displayed visually and/or analyzed, e.g., to find measurements of key swing parameters. Translated swing data used for reconstruction is referred to hereinafter as reconstructed swing data.

In one embodiment, the reconstructed swing data includes, e.g., a time series of position, acceleration, and rotation of all points of the golf club during a swing. In one embodiment, this data is presented in absolute terms or is given relative to the position/orientation of the tag device. The time series starts at an address and ends at the point of impact or follow through, and each point in the time series is able to be analyzed to determine swing parameters (e.g., orientation and position of the club in 3D space). Non-limiting examples of swing parameters that are then able to be calculated by the microcontroller include swing plane, swing tempo, swing velocity, swing force, impact force, club face angle, club face orientation, club head speed, point of ball impact, clubhead loft, hand speed, velocity of a golf club, a trajectory of the golf, ball, angle of impact between the golf club and the golf ball, a face angle of the golf club at impact with the golf ball, a club path during a golf swing, shaft lean at impact, shaft lean at address, shaft angle at top of backswing, and/or plane skew offset. Further, the reconstructed swing data is able to be translated such that the information included therein is represented graphically as a reconstructed swing "replay," e.g., on a display screen.

The microcontroller utilizes the reconstructed swing data described in the foregoing exemplary processing to graphically display a reconstructed swing "replay" and/or the swing parameters. The graphical swing reconstruction includes retrieving the reconstructed swing data time series and building a 3D view in which the club is mapped to the connected device's display based on the timeline and an indexing of the timeline. Alternatively, or in conjunction with the 3D reconstruction, the microcontroller displays calculated swing parameter numbers, such as club head speed, for any club position on the timeline. All data associated with the reconstructed swing is able to be stored in the memory of the connected device or communicated to and/or stored in the memory of another computing device for later use and/or for comparisons between a current swing and a past swing. One example of such a physics engine is described in Parke, et al. U.S. Pat. No. 8,905,856 for method and apparatus for determining a relative orientation of points on a rigid body issued to inventors Parke, et al., which is incorporated herein by reference in its entirety.

Referring back to FIG. 4C, the swing or shot data captured by the tag device is transmitted to the GPS-enabled display device and/or other display device for logging, processing, and display of the golf swing profile as illustrated in FIG. 4C. In the embodiment depicted in FIG. 4B, clicking on the View Full Swing button changes the display to show a 3D rendering of the user's swing taken at that location, as depicted in FIG. 4C.

Figure 5A:
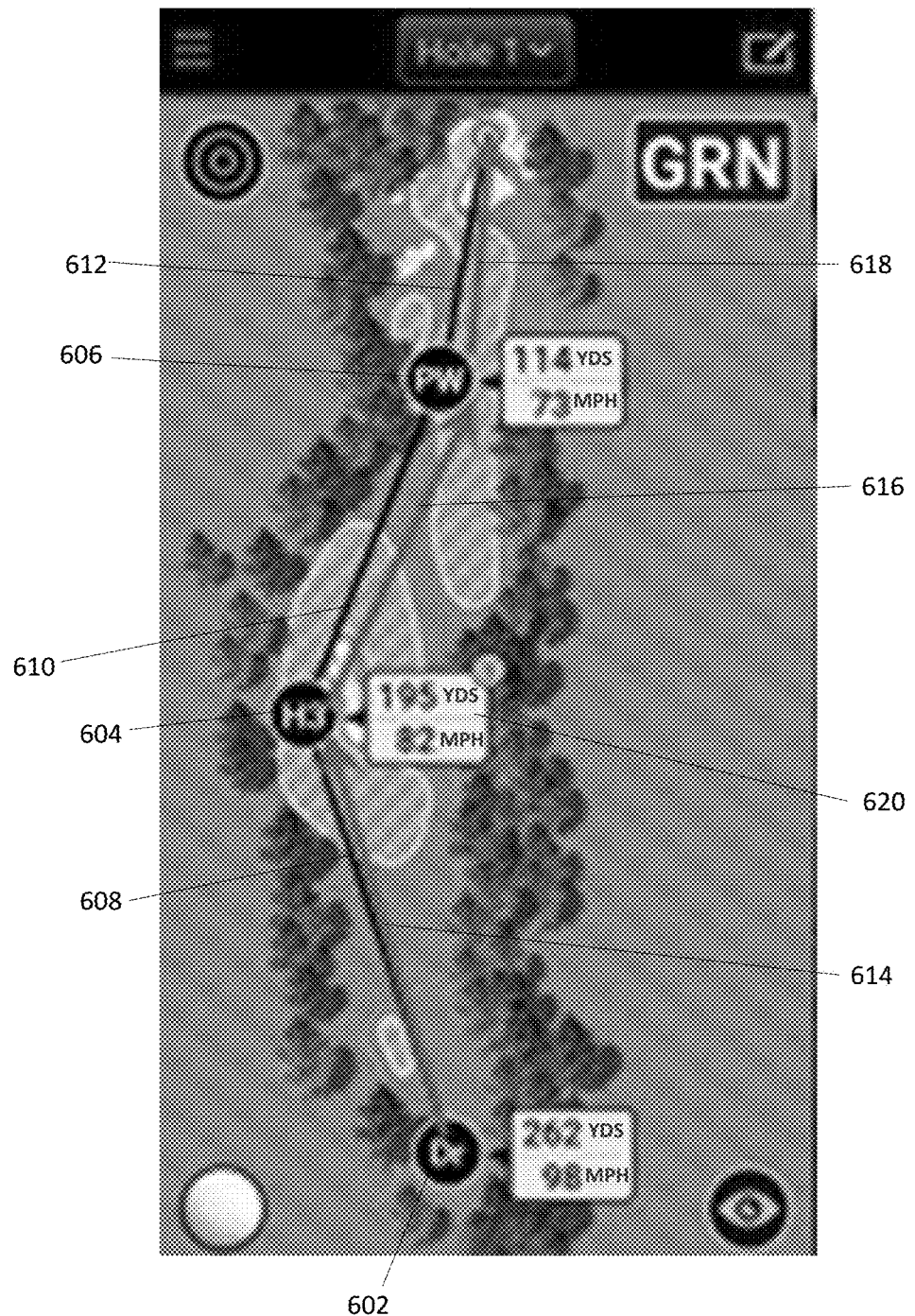
FIG. 5A illustrates an exemplary embodiment of a digital display showing the intended bearing to target compared to the actual bearing to target according to one embodiment of the present invention.

FIG. 5A illustrates an exemplary embodiment of a digital display of a connected device showing the intended bearing to target compared to the actual bearing to target which includes an optional magnetometer. The user is able to visualize the golf ball's starting position 602, the golf ball's subsequent landing positions 604 and 606, the intended bearing lines 614, 616, and 618, and the actual bearing lines 608, 610, and 612 along with other associated sensor data 620. This allows the golfer to analyze and visualize the characteristics associated which each golf swing in one cohesive location.

As illustrated in FIG. 5A, in one embodiment, the tag device is operable to determine the intended and actual bearing to target via a function applied to magnetometer sensor data. The intended bearing to target is determined by sensor data from the magnetometer when the golf club is pointed towards its intended target prior to a golf swing. More specifically, the golf club's magnetic position in relation to magnetic north is captured and recorded prior to the golf swing. In addition, in order to provide accurate swing orientation measurements during a golf swing, the magnetometer in the tag device accounts for the orientation of the club by calibrating based on data produced by the accelerometer and/or the gyroscope. In one embodiment, the tag device is operable to determine each shot's offset relative to the target location by using the magnetometer to locate the aim line of the golf club's face. In one embodiment, the tag device is operable to determine the shot trajectories offset relative to the aim of the golfer by comparing the clubface angle at impact to the clubface aim line and/or intended target line.

Figure 5B:
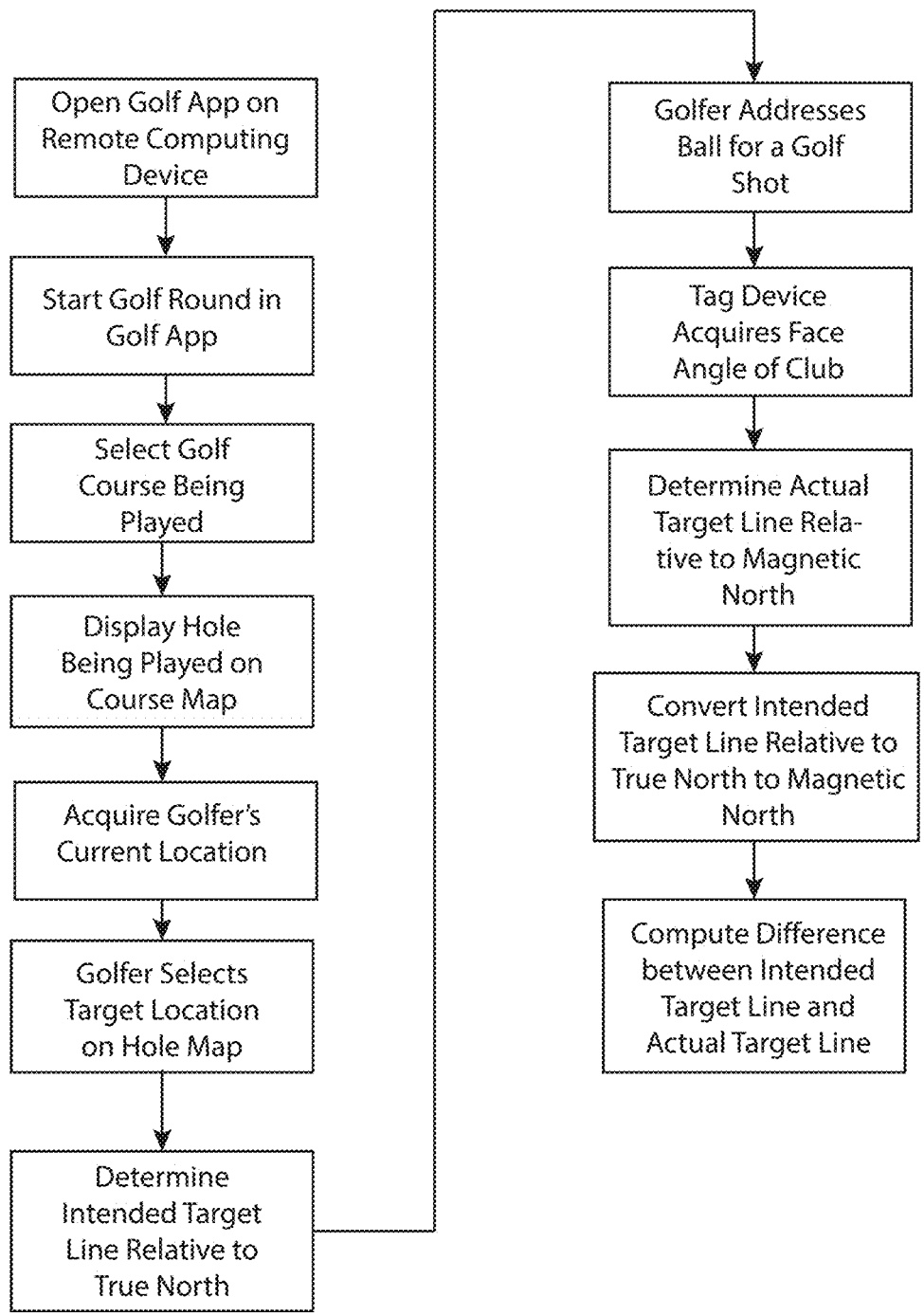
FIG. 5B illustrates a flowchart for an alignment feature according to one embodiment of the present invention.

FIG. 5B illustrates a flowchart for an alignment feature according to one embodiment of the present invention. In one embodiment, the present invention is operable to determine the intended aim alignment and the actual alignment relative to the target location. A golf application residing on the connected display device contains a geolocated map of the golf course being played and particularly of the golf hole being played. As illustrated in FIG. 5B, the golfer begins a round of play by opening the golf application on the connected display device. The golfer then selects Start Golf Round in the golf application and selects the golf course being played, unless, in one embodiment, the golf application automatically selects the course based on, for example, the golfer's location. A representation of the hole being played is then displayed on the connected display device, with the golfer again either selecting the hole being played or the golf application automatically selecting the hole being played. The connected display device then acquires and displays the golfer's location on the displayed representation of the hole. In another embodiment, the golfer manually selects their location by use of a user input device on the connected display device, such as, for example, a touch screen.

Before taking a shot, the golfer selects his intended target on the connected display device. This is done by the golfer using an input component within the display device, preferably a touch screen on the display device, to manually mark the location of his intended target. Alternatively, if the golfer did not select his target, the display device is able to set a default target, particularly if the golfer is hitting a tee shot or an approach shot into the green. Because the display device map is geolocated, the display device is able to determine the target location position relative to true north. The microcontroller in the golf application then determines the intended target line, i.e., the line from the golfer's location to the selected target location, and draws a line on the hole representation from the golfer's current location to the selected target location. The intended target line is determined relative to true north because the course map locations are also relative to true north. The golfer then addresses the ball in preparation of hitting it. Because the tag device contains a magnetometer, the tag device is able to determine the face angle (i.e., club alignment) at address of the club being used relative to magnetic north. The accuracy of this determination is enhanced if sensor data from an accelerometer and gyroscope are also used to determine face angle at address. In one embodiment, with the club face alignment established at impact, the sensor output data from the accelerometer and gyroscope tracks the club face alignment changes during the golf swing to the point of impact, thus establishing the club face angle or alignment at impact and throughout the swing. Once the golfer addresses the ball ready for a shot, the face angle of the club is acquired and the actual target line, i.e., the line extending outward and perpendicular to the club face, relative to magnetic north is determined. The intended target line relative to true north is converted to relative to magnetic north using methods known to those of ordinary skill in the art. Using the differential between the magnetic north readings, and/or along with the accelerometer and gyroscope data captured during the swing, the display device application determines the golf club's alignment at address, at impact, and throughout the swing relative to the intended target line.

In one embodiment, both the intended aim direction and the actual aim direction relative to the target location are overlayed on golf course imagery on a connected display device. Furthermore, true north data via declination offset tables and/or algorithms along with the vector of the golf ball flight path and landing is displayed either in real time or through post round analysis in relation to the intended aim direction. This allows a user to visualize their intended bearing and their actual bearing to target on the golf course they are playing on. Furthermore, this allows a user to identify accuracy issues in their golf swing and in the ball's flight.

In one embodiment, the intended bearings to target is determined by a calibration of the magnetometer using a 3×3 matrix and a 3×1 vector. The 3×3 matrix is a combination of a scale factor for each axis, a rotation, and a cross axis sensitive. The 3×1 vector is a measurement of the vector for each axis (i.e., the x axis, y axis, and z axis). In this embodiment, the 3×1 vector is added to each sample to represent the bias of magnetometer (i.e., one for each of the three axes measured by the magnetometer). The 3×3 matrix is then multiplied by the 3×1 sample with the 3×1 vector bias removed to determine a calibration sample for the intended bearings to target.

In one embodiment, the intended aim direction, relative to the target location, is determined from measurements from the magnetometer and measurements from the gyroscope during the golf swing to create a calibration of the magnetometer per swing. Implementation of the gyroscope to calibrate the magnetometer allows that calibration process to occur in a very short motion (i.e., the very beginning of the golf swing) rather than requiring a full swing profile. This process allows the tag device to withhold providing processing power to the gyroscope right up to the moment its sensor data is needed, in turn saving battery power.

In one embodiment, once the magnetometer is calibrated according to the above embodiments, it is further operable to use the position and angle of the golf club's face, as measured by the accelerometer and gyroscope, to compare to the position and angle of the magnetometer heading, which indicates the intended direction of the golf shot (i.e., the intended bearings to target). Furthermore, historical magnetometer and/or gyroscope data is factored into the system's calculation of the intended aim direction for fine tuning. As an example, if a golfer has the club face square to the intended target line while other golfers have the club face slightly more open, then the system adjusts the relationship between club face angle and the intended aim direction.

In one embodiment, the tag device is operable to determine the orientation of the golf club's face when in a hitting position based exclusively on accelerometer data. In this embodiment, the tag device saves power because the accelerometer draws much less power from the battery than the gyroscope. In this embodiment, the tag device is operable to analyze a ratio of acceleration along a z-axis relative to the y axis from the accelerometer to determine if the golf club is just simply being dragged around prior to getting ready for a golf swing (indicating an inactive state), being gripped in anticipation of a golf swing (indicating an active state), or being rotated in an arc extending upward to and/or above the golfer's head during a golf swing (indicating a data collection state). In this embodiment the gyroscope is only provided power during the data collection state. This allows the tag device to avoid using the gyroscope for as long as possible, which reduces processing power used by the tag device and extending its battery life.

Figure 6:
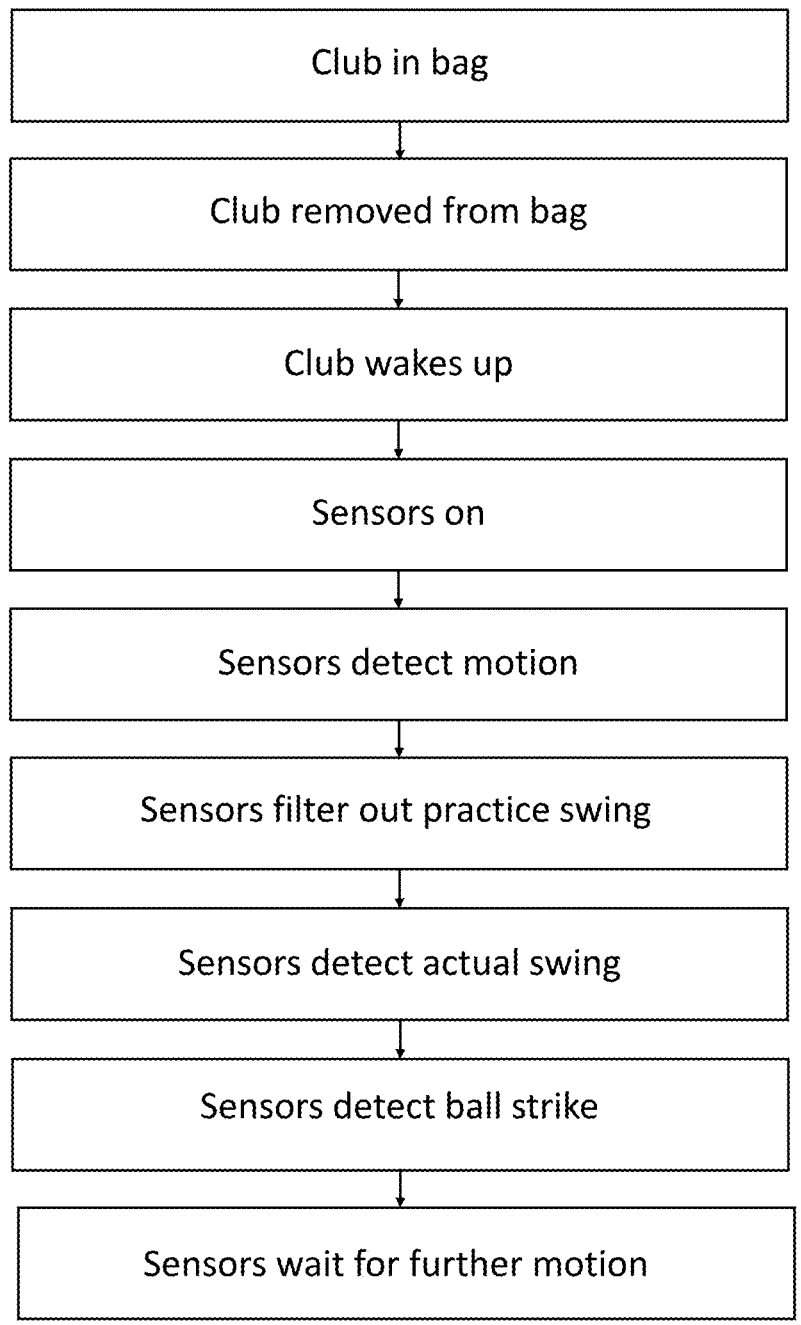
FIG. 6 illustrates a flowchart of the sensors' logic when the tag device is used according to one embodiment of the present invention.

FIG. 6 illustrates a general overview flowchart of the sensors' logic when the tag device is used according to one embodiment of the present invention. Referencing the embodiment described in FIG. 6, a golf club is stored in a golf bag, which is determined by the light sensor sensing a dark environment. When the golf club is removed from the golf bag and the light sensor senses a light environment, the tag device transitions into a different power state in which one or more of the sensors are powered and data collection is enabled. In one embodiment, the golf club is removed from the golf bag, and light is sensed, the accelerometer is activated to sense motion. The accelerometer is operable to detect motion, and as motion indicative of the club moving into a hitting position is detected, the remaining sensors are actuated and filter out practice swings by processing data from the sensors, including, at least one or more of the accelerometer, the optional magnetometer, and the gyroscope. The sensors are further operable to detect conditions that constitute an actual swing and subsequent golf ball strike. The sensors capture data associated with the golf swing. Following a golf swing, the sensors transition into another power state to await further movement of the club and/or a subsequent swing.

Figure 7:
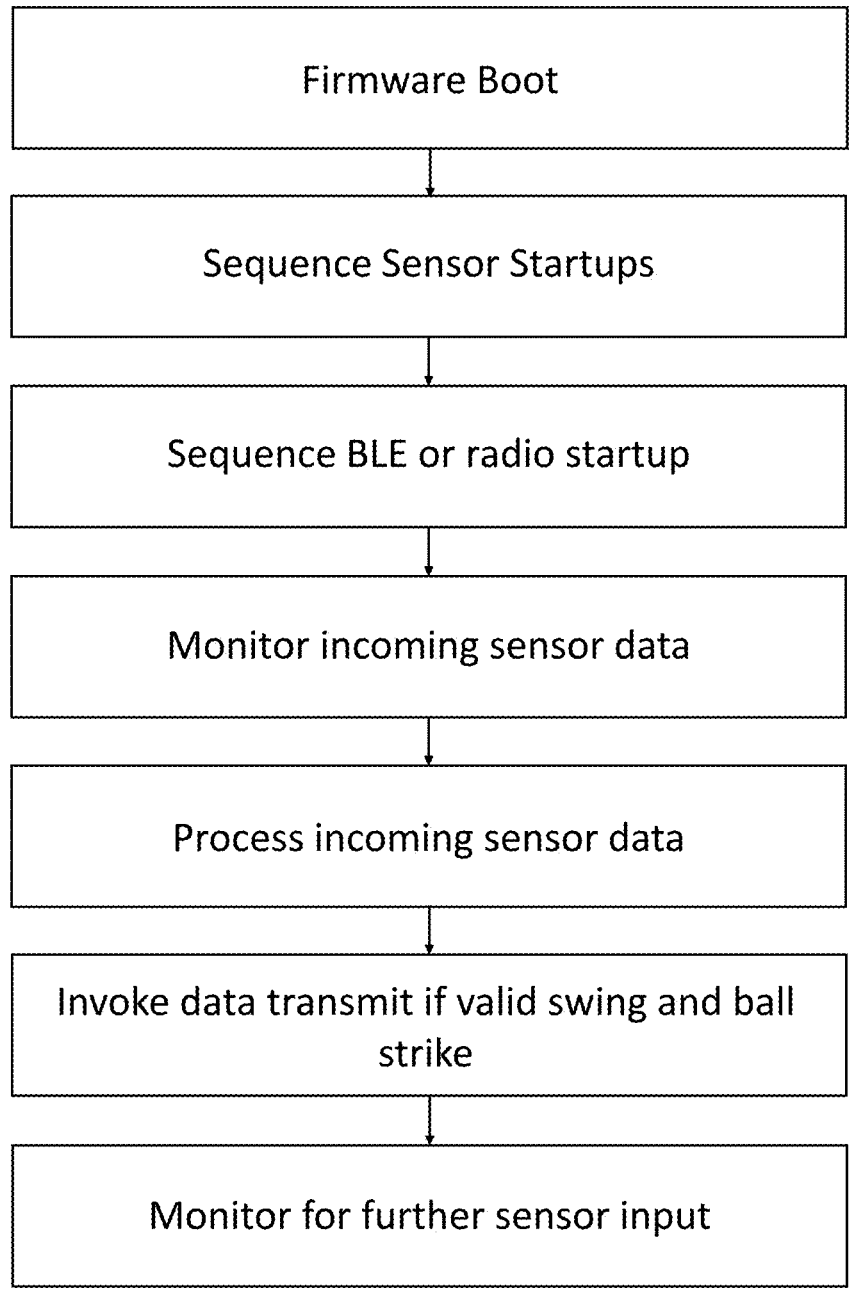
FIG. 7 illustrates a flowchart of the firmware according to one embodiment of the present invention.

FIG. 7 illustrates a flowchart of the firmware according to one embodiment of the present invention. In one embodiment, the firmware is booted-up and subsequently the plurality of sensors and computer components are booted-up. Incoming sensor data is monitored and any incoming sensor data is processed. Following a valid swing and ball strike, the data is transmitted to the display device. The firmware then monitors for further sensor input.

Figure 8A:
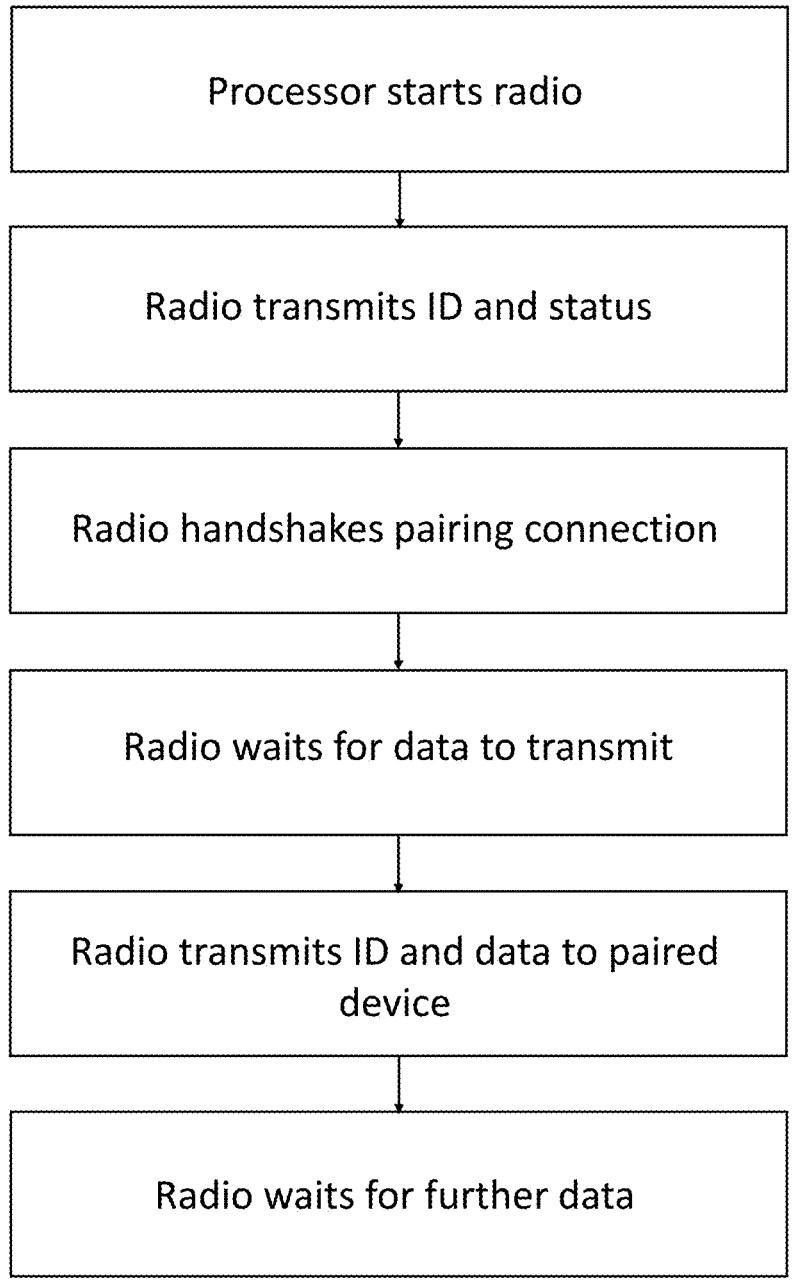
FIG. 8A illustrates a flowchart of the BLUETOOTH LOW ENERGY (BLE) and radio communication according to one embodiment of the present invention.
Figure 8B:
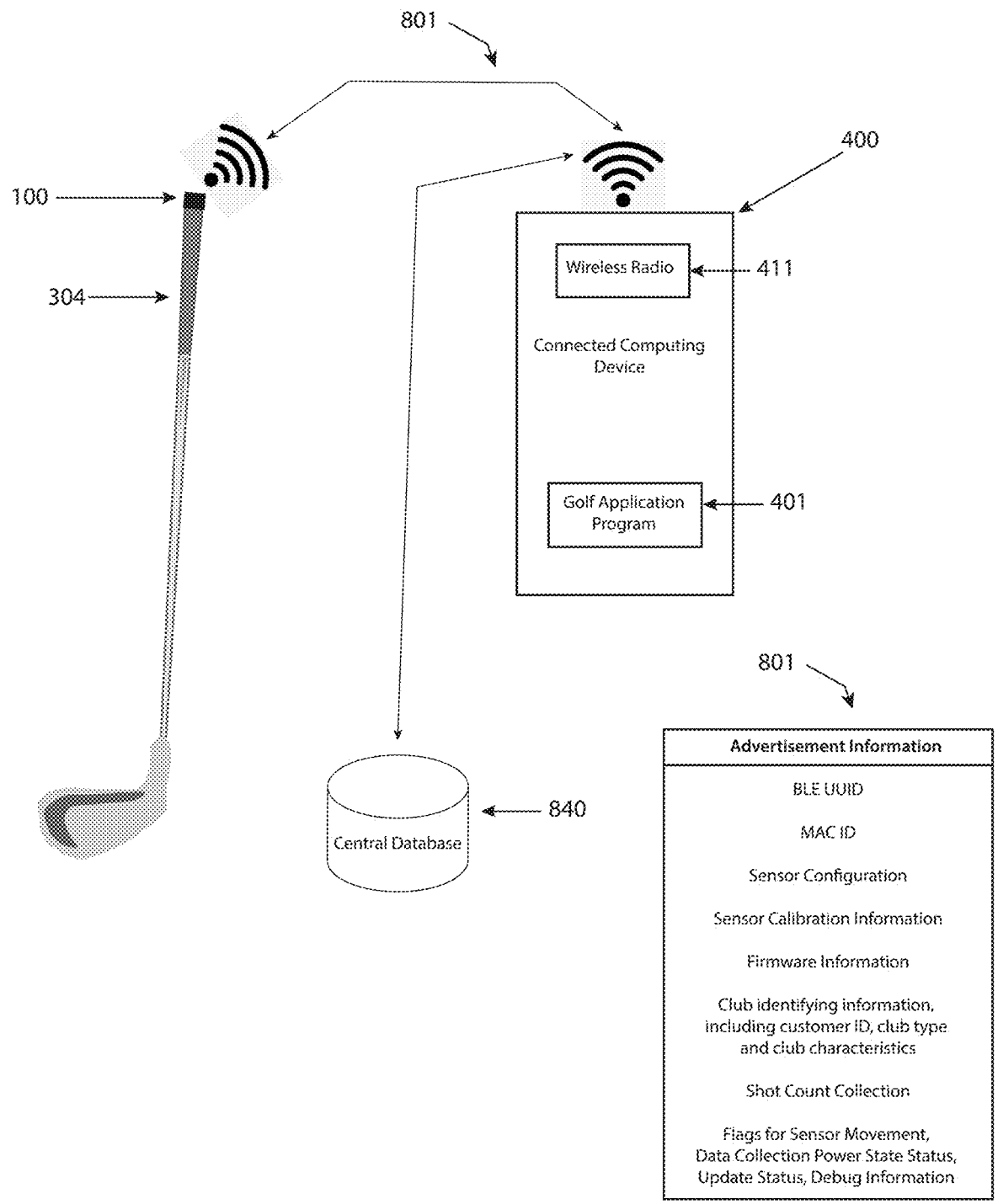
FIG. 8B illustrates BLE handshake communication of a preferred embodiment of the present invention.

FIG. 8A illustrates a flowchart of the BLE communication according to one embodiment of the present invention. In one embodiment, the processor starts the BLE radio, which then transmits an ESN or ID and status to a mobile and/or display device. In one embodiment, the BLE and radio handshakes to associate the display device and the tag device with one another and then awaits data transmission. The BLE radio transmits the ESN or ID to the display device, and then the BLE and radio waits for further data. FIG. 8B illustrates the BLE handshake communication of the preferred embodiment, and FIG. 8C illustrates the BLE protocol of the preferred embodiment. These figures are discussed in greater detail below.

Figure 9:
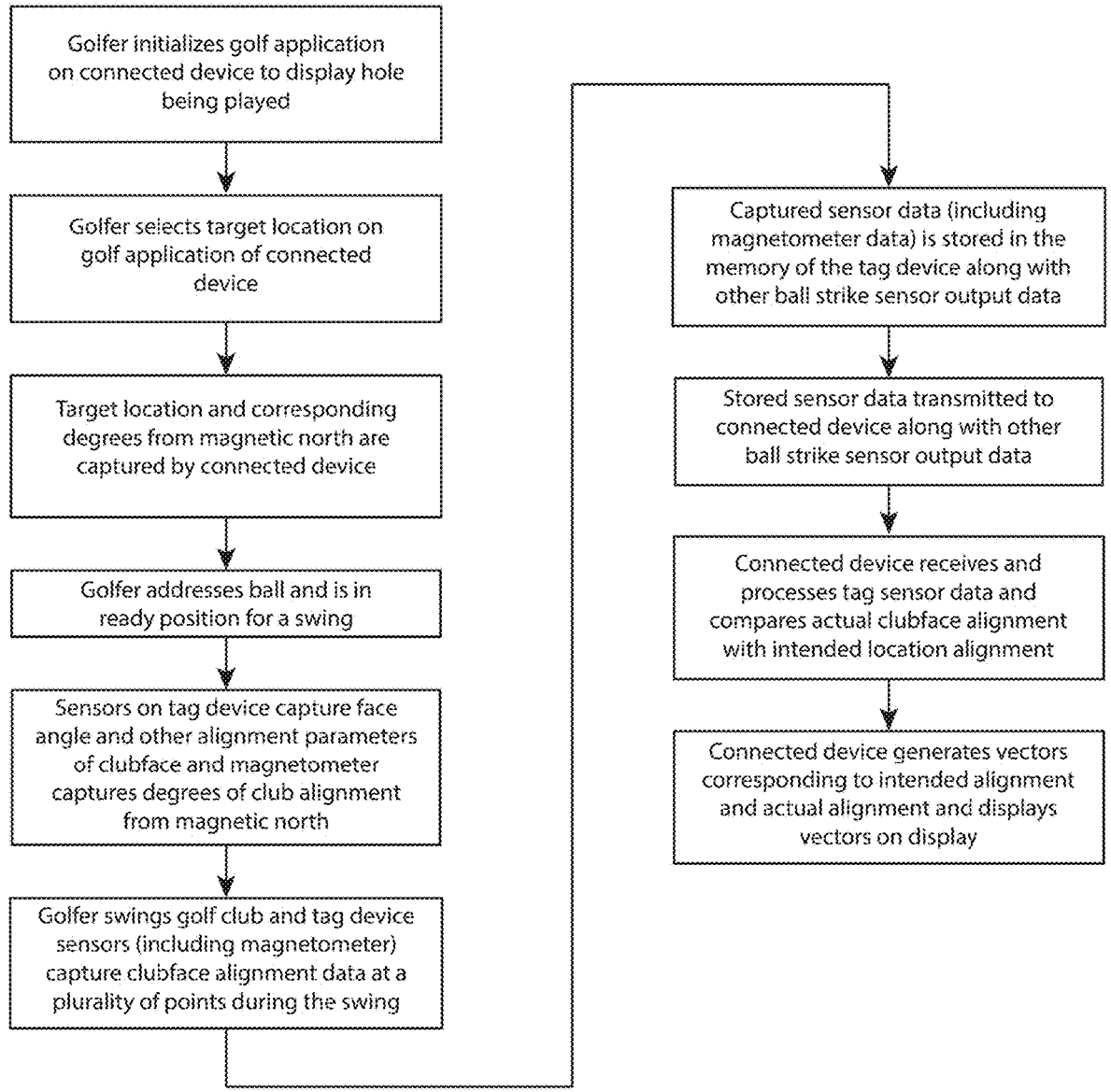
FIG. 9 illustrates a flowchart of the comparison of intended bearings to target compared to the actual bearing to target according to one embodiment of the present invention.

FIG. 9 illustrates a flowchart of the comparison of intended bearings to target compared to the actual bearing to target according to one embodiment of the present invention. In one embodiment, the golfer initializes a golf application on a remote display device, which then displays on the remote computing device the hole being played. Using a user input selector, such as, for example, a touchscreen on the remote display device, the golfer selects his intended target. Because the golf application includes a geolocated map of the golf course being played, the remote device captures the target location and corresponding latitudinal/longitudinal degree difference the target location is from magnetic north. As the golfer addresses the ball in anticipation of a ball strike, the magnetometer in the tag device, either alone or in conjunction with the other sensors in the tag device, such as, for example, the accelerometer and/or gyroscope, captures the actual face angle and other parameters of the face of the golf club to which the tag device is attached and the corresponding alignment relative to magnetic north, i.e., the actual alignment of the golf club. As the golfer swings the club to strike the ball, the magnetometer, together with the other sensors in the tag, continues to monitor and capture actual club alignment during the swing, at ball impact, and/or through the follow-through of the swing. The captured ball strike data is stored in the memory of the tag device and transmitted to the display device, where it is associated with geolocation metadata generated by the GPS unit of the display device. The connected display device, after receiving the ball strike sensor data from the tag device, processes the ball strike data and compares actual clubface alignment with intended clubface alignment. The remote display device then generates vectors for the actual alignment and intended location alignment and the intended aim direction and actual ball flight vector are graphically displayed to the user.

In one embodiment, the tag device is operable to extend its battery life by functioning in a plurality of power states. The plurality of power states describes computer protocols for running the plurality of sensors and/or computer components at various power levels (or no power at all). In one embodiment, the flash memory unit 105 contains the instructions to run the computer protocols that activate the plurality of power states and sends the instructions to the finite state machine 108. In one embodiment, the microcontroller 102 receives notification from the IMU 101 and/or photosensor 106 that predetermined sensor threshold values have been exceeded and then instructs the flash memory 105 to reload the registers of the IMU 101 based on the exceeded threshold values, whereupon one of the plurality of power states within the FSM is activated. In one embodiment, the microprocessor 116 sends the power state instructions from the flash memory 105 to the IMU 101, the 3-axis accelerometer 109, the 3-axis gyroscope 110, the magnetometer 104, and/or the photosensor 106. In one embodiment, the microprocessor 116 is operable to receive the plurality of sensor data from the IMU 101, the 3-axis accelerometer 109, the 3-axis gyroscope 110, the magnetometer 104, and/or the photosensor 106, and determines when and/or if a predetermined threshold has been exceeded, indicating a power state transition, is indicated. The finite state machine 108 is operable to run the computer protocols and/or power state instructions. The finite state machine 108, using the computer protocols and/or power state instructions from the flash memory unit 108, is operable to run the plurality of sensors at the various power levels. Thereafter, the finite state machine 108, is operable to request new computer protocols from the flash memory unit 105, when conditions (from the plurality of sensors) are such that a new power state should be activated. In one embodiment, the microprocessor 116 is operable to requests new computer protocols from the flash memory unit 105, when conditions (from the plurality of sensors) are such that a new power state should be activated. In one embodiment, the finite state machine 108 is operable to work in conjunction with the flash memory unit 105 and microprocessor 116 to operate the device 100 in a plurality of power states as described below. The plurality of power states are configured to optimize the amount of power drawn by the plurality of sensors so that data collection is not interfered and battery life is extended. Optionally, one or more of the sensors are monitored or managed by the microcontroller, such as, for example, the low power consuming photosensor. One skilled in the art, however, will appreciate that the more sensors which are primarily monitored or controlled by the microcontroller, the less efficiency the present invention will have in saving battery charge. Therefore, one object of the present invention is to move primary sensor monitoring or control to the IMU using finite state machine logic rather than traditional processing on the microprocessor of the main microcontroller.

FIGS. 10A and 10B illustrate the finite state machine protocols for a preferred embodiment of the present invention. In the preferred embodiment, the plurality of sensors, other than the photosensor, are managed by the finite state machine of the IMU in accordance with the protocol described in FIG. 10A. The photosensor is managed by the microcontroller in accordance with the protocol described in FIG. 10B. As illustrated in FIG. 10A, the finite state machine monitors the plurality of sensors within the IMU. When one or more of the plurality of sensors measures a value exceeding a pre-determined threshold or reference value for that sensor, the finite state machine detects that the sensor measured an exceeded threshold or reference value and signals the microcontroller that the threshold or reference value has been exceeded. The microcontroller then instructs the flash memory to reload the IMU's registers based on the corresponding exceeded value. The flash memory then reloads the IMU's registers based on the microcontroller's instructions, and the finite state machine changes the power state of the tag device, which results in changing of the powering of the plurality of sensors, based on the new register data. For example, in the preferred embodiment, in the inactive state, if the photosensor has not measured a return to dark, as the finite state machine monitors the accelerometer, and/or if the accelerometer measures a movement exceeding the pre-determined movement threshold or reference, upon detecting this exceeding of the threshold or reference, the finite state machine signals the microcontroller that the movement threshold or reference has been exceeded. The microcontroller instructs the flash memory to reload the IMU's registers based on the microcontroller's instruction, and, upon change of the IMU's registers, the finite state machine changes the state of the device from inactive to active and the sensors are powered according to the active state protocol, i.e., the photosensor remains powered and the accelerometer increases its cycle rate and is powered sufficiently for the increased cycle rate. One skilled in the art will recognize that while the word "exceeded" has been used herein in connection with threshold or reference values, the term refers not simply to a sensor that measures a value that goes over a maximum reference value, but also refers to a sensor that measures a value that goes below a minimum reference value. For example, if the tag device is in the inactive state and the photosensor measures a light value that is below the minimum reference value for light, the tag device transitions from the inactive state to the dark state.

In the preferred embodiment, the photosensor is in communication with, and monitored by, the microcontroller. Thus, referring to FIG. 10B, when the photosensor measures a value exceeding the pre-determined light threshold or reference value, the photosensor sends a communication to the microprocessor indicating the photosensor has detected the predetermined threshold or reference value of light. Upon receiving such communication, the microcontroller then instructs the flash memory to reload the IMU's registers based on the corresponding exceeded value. The flash memory then reloads the IMU's registers based on the microcontroller's instructions, and the finite state machine changes the power state of the tag device, and hence the corresponding powering of the plurality of sensors, based on the new register data.

Figure 11A:
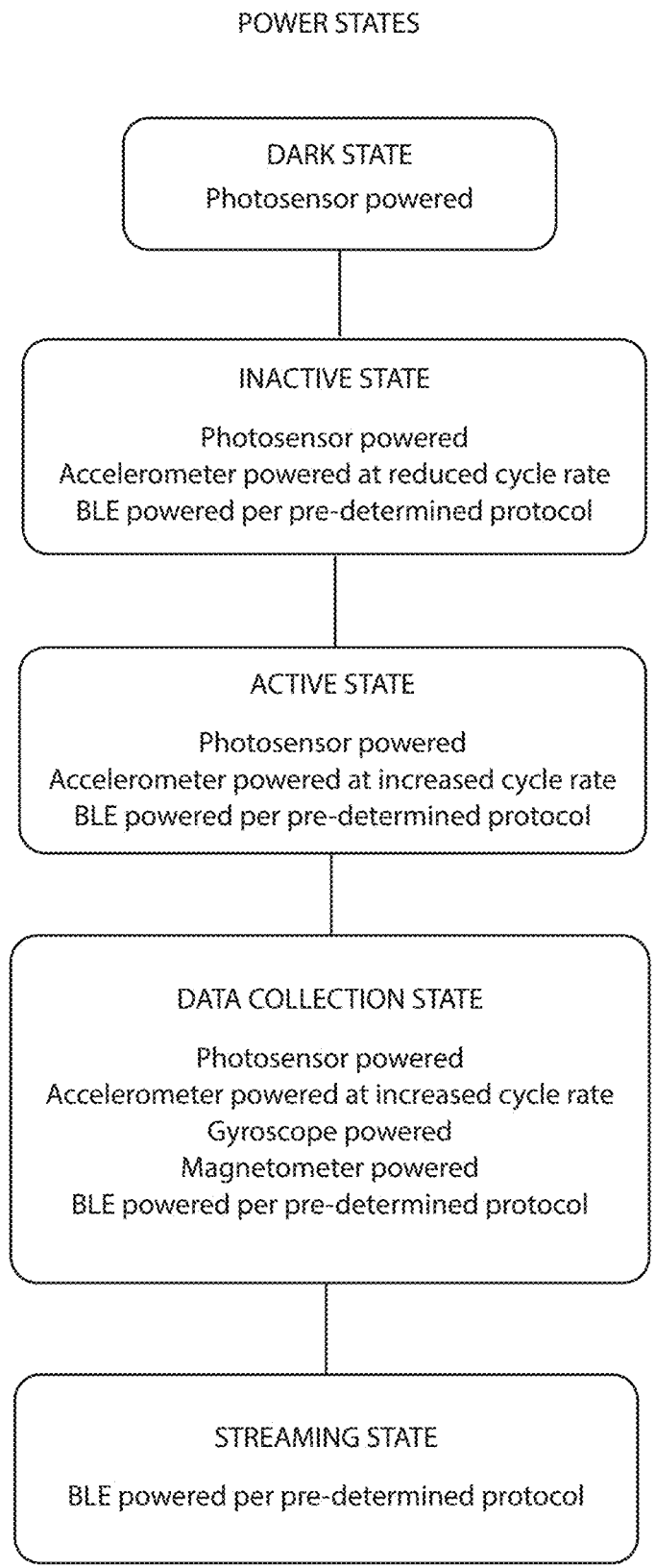
FIG. 11A illustrates information regarding power states of a preferred embodiment of the present invention.
Figure 11B:
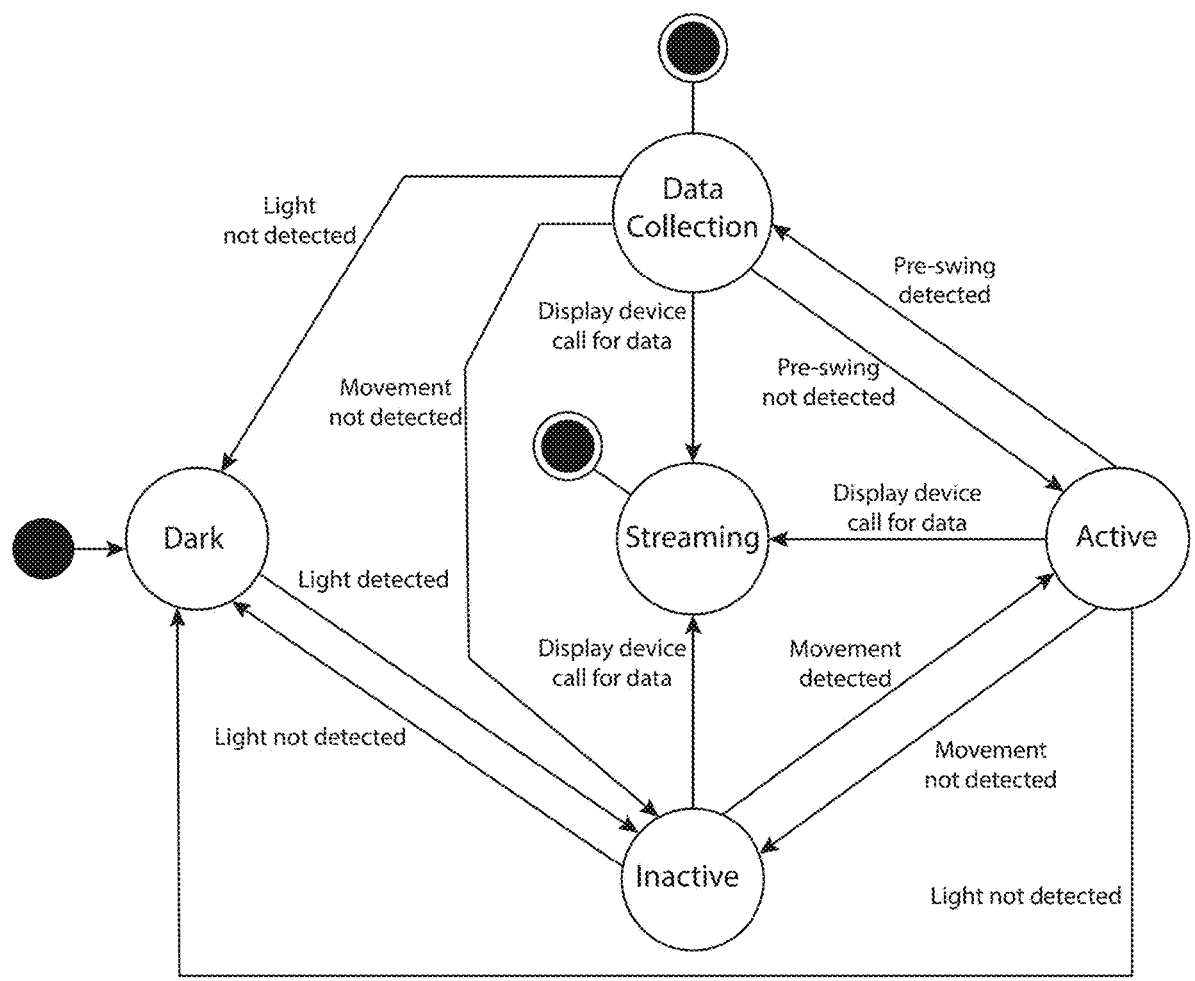
FIG. 11B illustrates a relational diagram of states and transition of a finite state machine of a preferred embodiment of the present invention.

While each state is separately discussed below, FIG. 11A illustrates the power states of the preferred embodiment, and FIG. 11B illustrates the transitions of each state of the finite state machine logic for the preferred embodiment.

Referring to FIG. 11A, at the start in FIG. 11A, the tag device is in the dark state. Upon detection of light exceeding a pre-determined light threshold value, the tag device transitions to the inactive state. At any time after the tag device has transitioned out of the dark state and is in another state, if the tag device no longer detects light exceeding the pre-determined light threshold value, the tag device transitions into the dark state. In the inactive state, upon detection of movement of the tag device exceeding a pre-determined movement threshold value, the tag device transitions to the active state. In the active state, upon the tag device detecting that the tag device has been oriented so that the grip end of the golf club is in an upright position indicative of the club being put in the hitting position (referred to as the pre-swing position), the tag device transitions to the data collection state. Once the tag device detects a ball strike in the data collection state, the data for the ball strike and swing corresponding to the ball strike are stored in the memory of the tag device, the tag device broadcasts that a swing has been stored in its memory in accordance with the BLE protocol, the process for that swing has ended, and the device transitions to the last state or other state based on the most recent sensor detections. While the tag device is in any state, other than the dark state, when the tag device receives a call for transmission of data from the associated display device, the tag device transitions into the streaming state in which the data stored in the memory of the tag device is transmitted to the display device. Once the data has been transmitted, the process ends and the device transitions to the last state or other state based on the most recent sensor detections.

Referring to FIG. 11B, the power states of the preferred embodiment are described, generally from lowest power state—i.e., the dark state requiring the least amount of power—to the highest power state—i.e., the data collection state requiring the most battery power. The streaming power state is, for convenience of illustration purposes only, placed at the bottom of FIG. 11B, but does not require the highest amount of power. In the dark state of the preferred embodiment, only the photosensor is powered. In the inactive state, the photosensor is powered, the accelerometer is powered at a lower cycle rate, and the BLE is powered in accordance with the predetermined BLE protocol. The accelerometer is powered at a lower cycle because in the transition from inactive state to the active state, the pre-determined movement threshold need only be sensitive enough to detect general movement of the tag device. This detection does not require more discrete measurements that require higher accelerometer cycle rates. In the active state, the photosensor is powered, the accelerometer's cycle rate is increased and the accelerometer is powered accordingly, and the BLE is powered in accordance with the predetermined BLE protocol. The accelerometer is powered at a higher cycle rate because in the transition from active state to data collection state, the pre-determined movement threshold needs to be more sensitive to detect movement of the tag device, and hence the golf club, into a specific position, i.e., an upright position indicative of the hitting position, rather than just detecting general movement of the tag device. One skilled in the art will appreciate that powering the accelerometer at the lowest cycle rate sufficient to measure the predetermined movement threshold for the then current state will achieve greater power efficiency. In the data collection state, the photosensor is powered, the accelerometer is powered at the higher cycle rate, the gyroscope is powered, the optional magnetometer is powered, and the BLE is powered in accordance with the predetermined BLE protocol. In the streaming state, the BLE is powered in accordance with the predetermined BLE protocol.

Figure 12A:
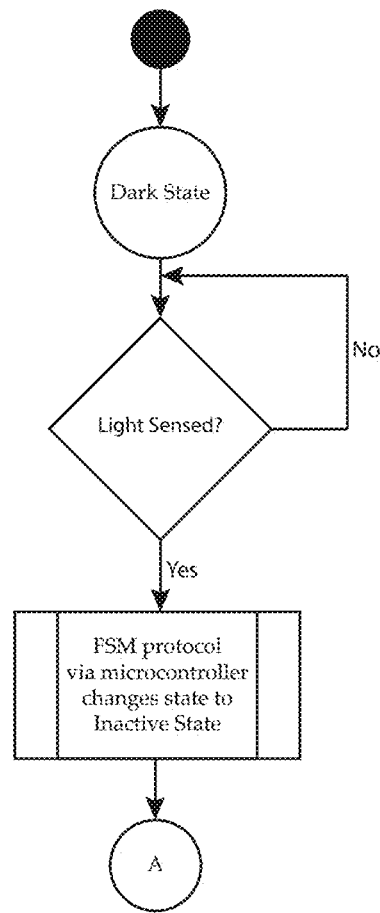
FIG. 12A illustrates a flowchart of the power state logic for a tag dark state power mode according to one embodiment of the present invention.

FIGS. 12A-E illustrate the power state logic for the various states of a preferred embodiment of the present invention. FIG. 12A illustrates the power state logic for dark state power mode according to a preferred embodiment of the present invention. The dark state power mode represents the power state configured to conserve the most energy and extend the battery charge of the tag device to the greatest degree. The dark state represents the common situation where a golf club is not in use and not capturing swing data. The dark state extends the battery charge of the tag device by shutting down all but the most essential sensors and components when the golf club is at rest, in a golf bag, or otherwise not likely in use or about to generate swing data. In the dark state, although one or a plurality of sensors are powered, it is preferable to power the fewest sensors that are practical to determine whether the golf club is in use and likely about to provide swing data in order to conserve energy and, hence, save battery charge. In a preferred embodiment, as illustrated in FIG. 12A, the tag device uses minimal battery power by only powering the light sensor in the dark state.

It should be understood that when describing the environment that the tag device is subject to, the golf club upon which the tag device is affixed is experiencing the same environment, such that, for example, determining the orientation or light status of the golf club is made by determining the orientation or light status of the tag device affixed to the club.

In one embodiment, sensors that detect movement, position, and/or the presence of the light determine whether a dark state is initiated. In another embodiment, the tag device is operating in a dark state when the golf club is at rest, with no or little light detected, and with the handle grip oriented downwards (i.e., other than in an upward-pointing position indicative of a golfer about to swing the club). However, one of ordinary skill in the art will understand that dark state is also initiated when the golf club is in other dark conditions that indicate nonuse of the golf club, such as, for example, a golf club at rest in an upright position in a dark environment (e.g., a basement or closet) or a golf club oriented downward but moving inconsistently with a golf swing in a dark environment (e.g., the trunk of the vehicle). Alternatively, a dark state is also initiated when the golf club is in a light condition but movement or orientation of the club indicates non-use. For example, the golf club laying on its side without movement for a pre-determined amount of time activates a dark state, even though light is detected. As previously noted, the term "dark state" is merely the nomenclature employed by the patentee to identify the power state requiring the lowest powering of sensors, and non-light conditions should not be construed as a required limitation of the tag device being in a "dark state."

In a preferred embodiment, the tag device exclusively provides power to the light sensor when operating in a dark state. In this preferred embodiment, the photosensor, which is a relatively low consumer of power, is monitored, or managed, by the microcontroller, unlike the remaining sensors which are monitored, or managed, by the finite state machine of the IMU. In the embodiment shown in FIG. 12A, the tag device is operable to leave the dark state and/or enter the inactive state only upon sensing a light environment. When the tag device is in the dark state, the microcontroller monitors the photosensor. When the photosensor measures light exceeding the pre-determined threshold, the microcontroller detects the measurement exceeding the threshold value and instructs the flash memory to reload the IMU registers based on the exceeded threshold value. Upon change of the register values, the finite state machine changes the state of the device from dark state to inactive state and the sensors are powered according to the inactive state protocol, i.e., the photosensor remains powered and the accelerometer is powered and begins measurements at a reduced cycle rate.

In one embodiment, the tag device is operable to enter the dark state from the inactive state, active state, data collection state, and/or streaming state. In one embodiment, the tag device processes sensor data to determine if the golf club is at rest and not in use and therefore should enter a dark state. Conversely, if the tag device processes sensor data to determine that the golf club is in motion, ascertained by pre-determined motion thresholds, the tag device will enter an inactive state, active state, data collection state, and/or streaming state. If the tag device senses that the golf club is at rest, grip oriented downwards, and in a dark environment (i.e., no or low light is detected), the tag device immediately enters into a dark state power mode. In one embodiment, if the tag device does not sense a light environment (i.e., the golf club is in a dark environment like a golf bag), the tag device is operable to enter the dark state. One skilled in the art will appreciate that the determination whether to initiate a dark state is able to be made by powering only one sensor, e.g., an accelerometer, gyroscope, or light sensor, etc., and processing only one condition, e.g., movement of the club, orientation of the club, or light conditions of the club, etc., or by a plurality of two or more sensors and conditions. One skilled in the art will also appreciate that in an embodiment in which a plurality of sensors or conditions is used to determine whether to transition from one state to another, the logic is able to consider the sensor outputs or conditions in any order and also consider the sensor outputs or conditions either in parallel or serially.

In one embodiment, the tag device may additionally employ a timing threshold where the tag device processes sensor data and, after a pre-determined time interval of not sensing a swing, movement or other sensed condition, transition the tag device to a different state. For example, in the embodiment illustrated in FIGS. 12A-D, a timing interval is employed in which the tag device is placed back in the active state from the data collection state if the grip orientation is initially detected as being in a hitting position but the device does not sense, within a selected time interval, movement within the thresholds indicative of a swing. In another embodiment, the tag device is configured to enter into a dark state depending on a plurality of pre-determined threshold values for the grip orientation, light environment sensed, motion detected, and/or other sensed conditions. One of ordinary skill in the art will understand that the tag device is able to have varying pre-determined time intervals of not sensing a swing or other movement or condition before it automatically reenters the dark state or other power state mode.

In one embodiment, the light sensor operates at approximately seven nanoamps while the tag device is in the dark state. In this embodiment, the finite state machine 108 operates at a lower power to process the light sensor data. In one embodiment, the accelerometer operates at a low power state while the tag device is in the dark state. In one embodiment, the accelerometer operates at approximately 1.6 Hz while the tag device is in a dark state.

Figure 12B:
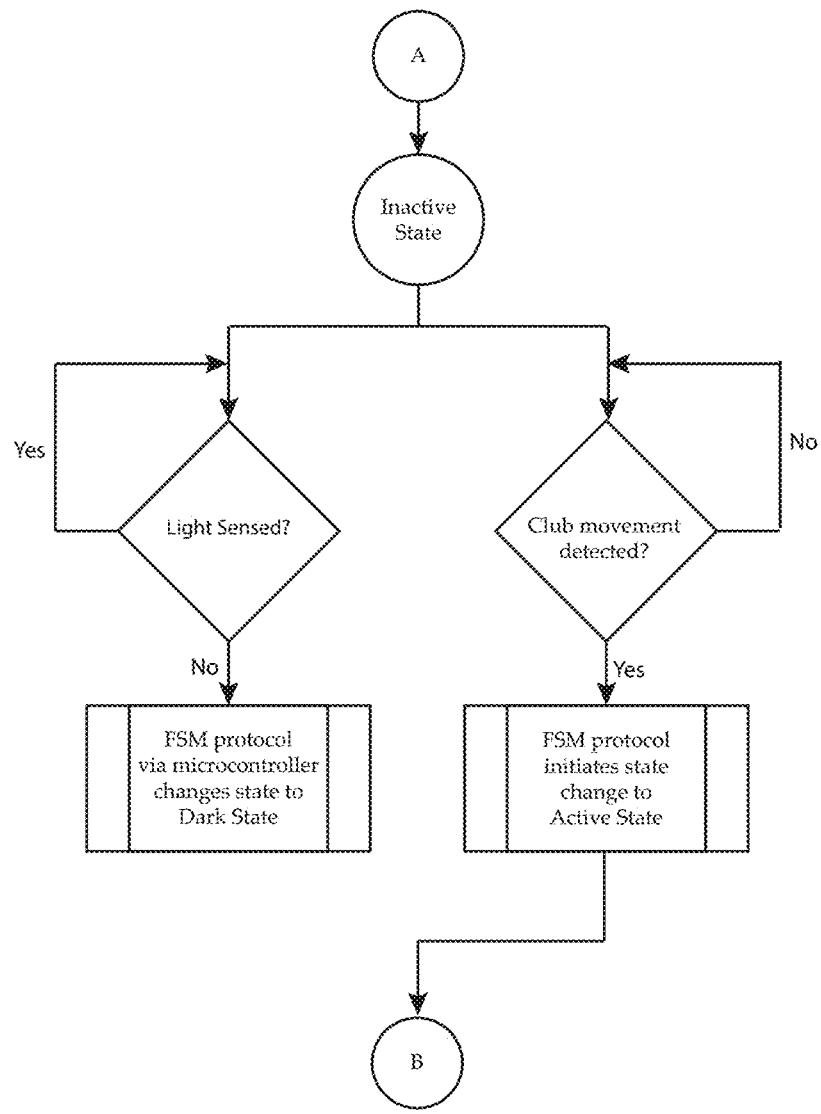
FIG. 12B illustrates a flowchart of the power state logic for a tag inactive state power mode according to one embodiment of the present invention.

FIG. 12B illustrates the power state logic for an inactive state power mode according to a preferred embodiment of the present invention. In the preferred embodiment, the inactive state is a power state that saves battery power by providing power to the light sensor, minimal power to the accelerometer which operates at a low cycle rate, and to the BLE powered in accordance with the predetermined BLE protocol. In one embodiment, the tag device will enter an inactive state after the tag device has been in an active state and stationery for a pre-determined interval of time, regardless of grip orientation. In one embodiment, the tag device enters an inactive state based on variables including low movement detection, low light detection, and/or grip orientation.

In the preferred embodiment as illustrated in FIG. 12A, an inactive state is entered when the tag device detects a light environment. In one embodiment, an inactive state is entered when the tag device detects a light environment and a golf club at rest (i.e., substantially no movement detected). In one embodiment, the tag device considers grip orientation data in determining whether to enter an inactive state or not. In the preferred embodiment, where the tag device is in an inactive state and light is not detected, the tag device enters a dark state as illustrated in FIG. 12B. In one embodiment, where the tag device is initially in an inactive state, light is detected, and motion is detected, the tag device enters an active state or a data collection state. In one embodiment, where the tag device detects a light environment and a golf club at rest for a pre-defined interval, the tag device is placed in an inactive state.

In one embodiment, upon transition into the inactive state, the microprocessor refreshes the finite state machine's processing logic, which instructs the plurality of sensors contained in the IMU to function at one of a high rate, reduced rate, and/or normal rate (i.e., provide a high, low, or normal amount of power). In one embodiment, upon transition into the inactive state, the microprocessor refreshes the finite state machine's processing logic to instruct the light sensor to function at a normal rate and instructs the accelerometer to function at a low rate.

In one embodiment, upon transition into the inactive state, the flash memory unit refreshes the finite state machine's processing logic, which instructs the plurality of sensors contained in the IMU to function at one of a high rate, reduced rate, and/or normal rate (i.e., provide a high, low, or normal amount of power). In one embodiment, upon transition into the inactive state, the flash memory unit refreshes the finite state machine's processing logic to instruct the light sensor to function at a normal rate and instructs the accelerometer to function at a low rate.

Referencing FIG. 12B, in the preferred embodiment, when the tag device is in the inactive state, the photosensor is powered, the accelerometer is powered but operating at a low cycle rate that requires less power, and the BLE is powered in accordance with the predetermined BLE protocol. The microcontroller monitors the photosensor and the finite state machine monitors the accelerometer. As further illustrated in FIG. 12B, if the photosensor detects light below the pre-determined light threshold (i.e., indicating a return to dark conditions), the tag device follows the protocol described in FIG. 10B and returns the tag device to the dark state. If the photosensor has not measured a return to dark, as the finite state machine monitors the accelerometer, and/or if the accelerometer measures a movement exceeding the pre-determined movement threshold, upon detecting this exceeding of the threshold, the tag device follows the protocol described in FIG. 10A, and the finite state machine signals the microcontroller that the movement threshold has been exceeded. The microcontroller instructs the flash memory to reload the IMU's registers based on the microcontroller's instruction, and the finite state machine, upon receiving the change in register instructions, changes the state of the device from inactive to active and the sensors are powered according to the active state protocol, i.e., the photosensor remains powered and the accelerometer increases its cycle rate and is powered sufficiently for the increased cycle rate.

Figure 12C:
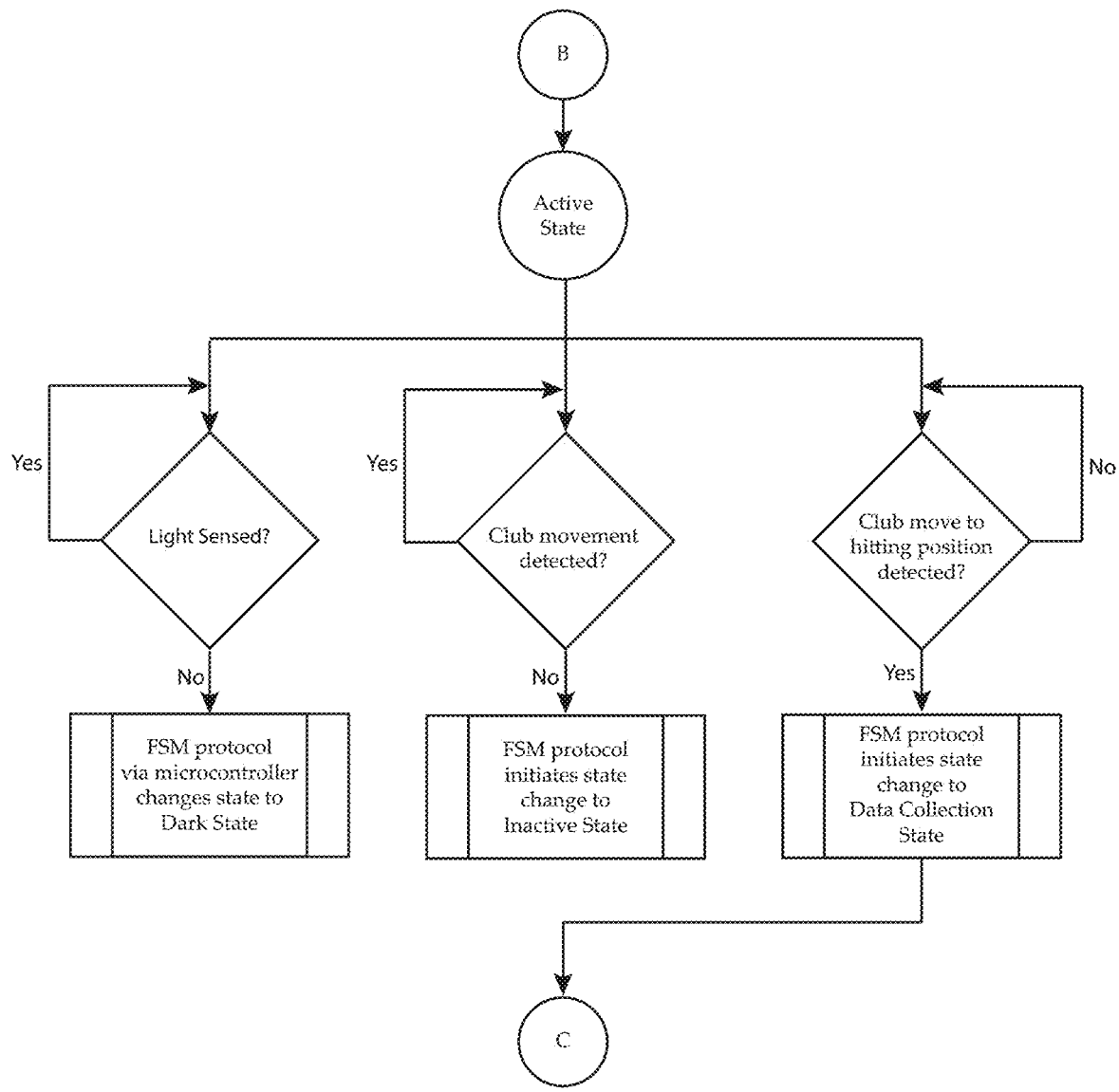
FIG. 12C illustrates a flowchart of the power state logic for a tag active state power mode according to one embodiment of the present invention.

FIG. 12C illustrates a flowchart of the power state logic for an active state power mode according to the preferred embodiment of the present invention. An active state describes an environment where the tag device detects a light condition and movement of the club but the club is not in a position that a swing or strike is likely to occur relatively soon in time. In one embodiment, the tag device is operable to provide power to the light sensor, accelerometer, and optional magnetometer when operating in an active state. In one embodiment, while operating in an active state, the tag device is operable to provide variable levels of power to the light sensor, accelerometer, and optional magnetometer. In the preferred embodiment, in the active state, the tag device is operable to provide power to the light sensor, to the accelerometer where the accelerometer operates at an increased, or high, cycle rate and is powered accordingly, and to the BLE in accordance with the predetermined BLE protocol. In a preferred embodiment as illustrated in FIG. 12B, the tag device will enter an active state when the golf club is in a light environment and moving, but not in a position likely to strike a golf ball, e.g., the club is not oriented upward in the position the golfer holds the club just before swinging it to strike a ball. In one embodiment, the tag device will enter an active state when the light sensor detects a light level above a minimum threshold, golf club movement is detected, and the golf club grip is oriented upwards. In one embodiment, the tag device exits the active state and enters a different power state when a light environment is not sensed, golf club movement is not detected, and/or the golf club grip is oriented not in an upward position (i.e., a striking position).

In one embodiment, upon transition into the active state, the microprocessor refreshes the finite state machine's processing logic, which instructs the plurality of sensors contained in the IMU to function at a high rate, reduced rate, and/or normal rate (i.e., provide a high, low, or normal amount of power). In one embodiment, upon transition into the active state, the microprocessor refreshes the finite state machine's processing logic to instruct the accelerometer to function at a normal and/or high rate.

In one embodiment, upon transition into the active state, the flash memory unit 105 refreshes the finite state machine's processing logic, which instructs the plurality of sensors contained in the IMU to function at a high rate, reduced rate, and/or normal rate (i.e., provide a high, low, or normal amount of power). In one embodiment, upon transition into the active state, the flash memory unit refreshes the finite state machine's processing logic to instruct the accelerometer to function at a normal and/or high rate.

Referencing FIG. 12C, in the preferred embodiment, when the tag device is in the active state, the photosensor is powered, the accelerometer is powered and operating at a high cycle rate that permits more discrete measurements than in the inactive state, and the BLE is powered in accordance with the predetermined BLE protocol. In the preferred embodiment, the microcontroller monitors the photosensor and the finite state machine monitors the accelerometer. If the photosensor does not detect light exceeding the pre-determined light threshold (i.e., indicating a return to dark conditions), the tag device follows the protocol described in FIG. 10B, otherwise the tag device remains in the active state. If the photosensor has not measured a return to dark, as the finite state machine monitors the accelerometer, if the accelerometer measures a movement exceeding the pre-determined active state movement threshold, i.e., a movement indicating the club has been moved into an upright, hitting position, upon detecting this exceeding of the threshold, the tag device follows the protocol described in FIG. 10A, and the finite state machine signals the microcontroller that the movement threshold has been exceeded. The microcontroller instructs the flash memory to reload the IMU's registers based on the microcontroller's instruction, and the finite state machine, upon receiving the change in register instructions, changes the state of the device from the active state to the data collection state and the sensors are powered according to the data collection state protocol, i.e., the photosensor remains powered, the accelerometer remains powered and cycled at the higher rate, the gyroscope is powered, the magnetometer is powered, and the Bluetooth BLE is powered in accordance with the predetermined BLE protocol. In the preferred embodiment, the pre-determined active state movement threshold is preferably based on movement of the golf club indicating the club is being oriented into a hitting position, i.e., the grip end is oriented upward in the position the golfer holds the club just before swinging it to strike a ball.

The golf club of one embodiment is in the pre-swing position when the shaft of the club is at an angle that is in the range of $X°+/-Y°$, where $X°$ is the selected angle of the club shaft from horizontal and $Y°$ is the selected upper and lower deviation from $X°$, preferably a deviation of no more than $+/-10°$. Because the various golf clubs in the typical set of 14 golf clubs have varying lie angles, i.e., the angle of the club shaft from horizontal, and golfers of different heights hold clubs at different angles, the angle of the club shaft in the pre-swing position will vary by golf club. One skilled in the art will appreciate that X should equal the angle at which an average golfer holds the golf club when addressing the ball to strike it, and Y will equal an anticipated range to account for the variability in, e.g., the height of the golfer, how upright a golfer holds the club, the playing conditions such as a sidehill lie with the ball above or below the golfer's feet, etc. Optionally, one embodiment also includes exceeding a threshold for movement along an x, y, and/or z axis with or without a time period component, as an additional transition condition to eliminate, for example, the golfer propping the golf club against a wall, the golf cart, the golf bag, or the like that simulates a pre-swing position but that is not actually in a pre-swing position.

In one embodiment, detection of an orientation of the tag device on the golf club by the accelerometer causes the microprocessor to instruct the tag device to transition to a data collection state. In one embodiment, the data collection state is entered when the club is relatively stable over a predetermined amount of time in a "ready to swing" position. In one embodiment, the tag device is calibrated in order to determine the ready to swing position. In one embodiment, calibration occurs by pressing a button or otherwise activating a calibration mode on the tag device or the connected display device while in a "ready to swing" position. The tag device then determines the current vector orientation detected by the accelerometer to determine a normal pre-swing orientation of the golf club. In another embodiment, "ready to swing" orientation is determined by calibrating the tag device with a user device attached to the club face and/or the club shaft, wherein the user is prompted to stand in one or more calibration stances (e.g., ready to swing position) and/or perform one or more calibration motions (e.g., full swing, practice swing, small putt, etc.). By performing the calibration step, the tag device and/or the user device saves a normal pre-swing orientation and determines an adjusted z-axis. In one embodiment, determining the adjusted z-axis includes determining x, y, and z acceleration vector components on the accelerometer in the pre-swing orientation and using vector projection to define an adjusted reference frame such that the pre-swing acceleration vector aligns with a z-axis of the adjusted reference frame. Using an adjusted z-axis, rather than the z-axis of the accelerometer is frequently necessary as golfers have different stances, where the club is often not substantially vertical when in a pre-swing position.

In one embodiment, the tag device is instructed to enter the data collection state when the acceleration along the adjusted z-axis is between approximately 0.9 and approximately 1.2 g. This allows for some tolerance of minor movements and wobble while in the pre-swing orientation. In one embodiment, the tag device is instructed to enter the data collection state when the acceleration along the adjusted z-axis is between approximately 0.9 and approximately 1.2 g and the total acceleration detected by the acceleration is below a preset threshold (e.g., about 1.25 g). Because additional acceleration is added when force is applied to the club to perform the swinging action, it is possible for acceleration along the adjusted z-axis to be within the desired range for entering the data collection state while the club is not actually still or in a downward position, but rather being swung around (e.g., in a practice swing). Therefore, filtering out total acceleration with values significantly greater than the acceleration solely along the adjusted z-axis allows the system to only enter the data collection state when the club is in a stationary, pre-swing orientation.

In another embodiment, there is increased angle tolerance for when to enter the data collection state. For example, if the accelerometer detects acceleration data indicating the club is oriented between about 20° and about −20° relative to the adjusted z-axis and the club is substantially still for a predetermined amount of time, then tag device is set to enter the data collection state. In one embodiment, in order to ensure that the club is relatively still before entering the data collection state, the tag device only enters the data collection state when the difference between two or more accelerometer readings at a predetermined sampling rate (e.g., every half second, every second, every two seconds, etc.) is below a preset threshold (e.g., 0.2 g) along a single axis. In another embodiment, in order to ensure that the club is relatively still before entering the data collection state, the tag device only enters the data collection state when the difference between two or more accelerometer readings at a predetermined sampling rate (e.g., every half second, every second, every two seconds, etc.) is below a preset threshold (e.g., 0.2 g) for the total magnitude of acceleration detected by the accelerometer.

Figure 12D:
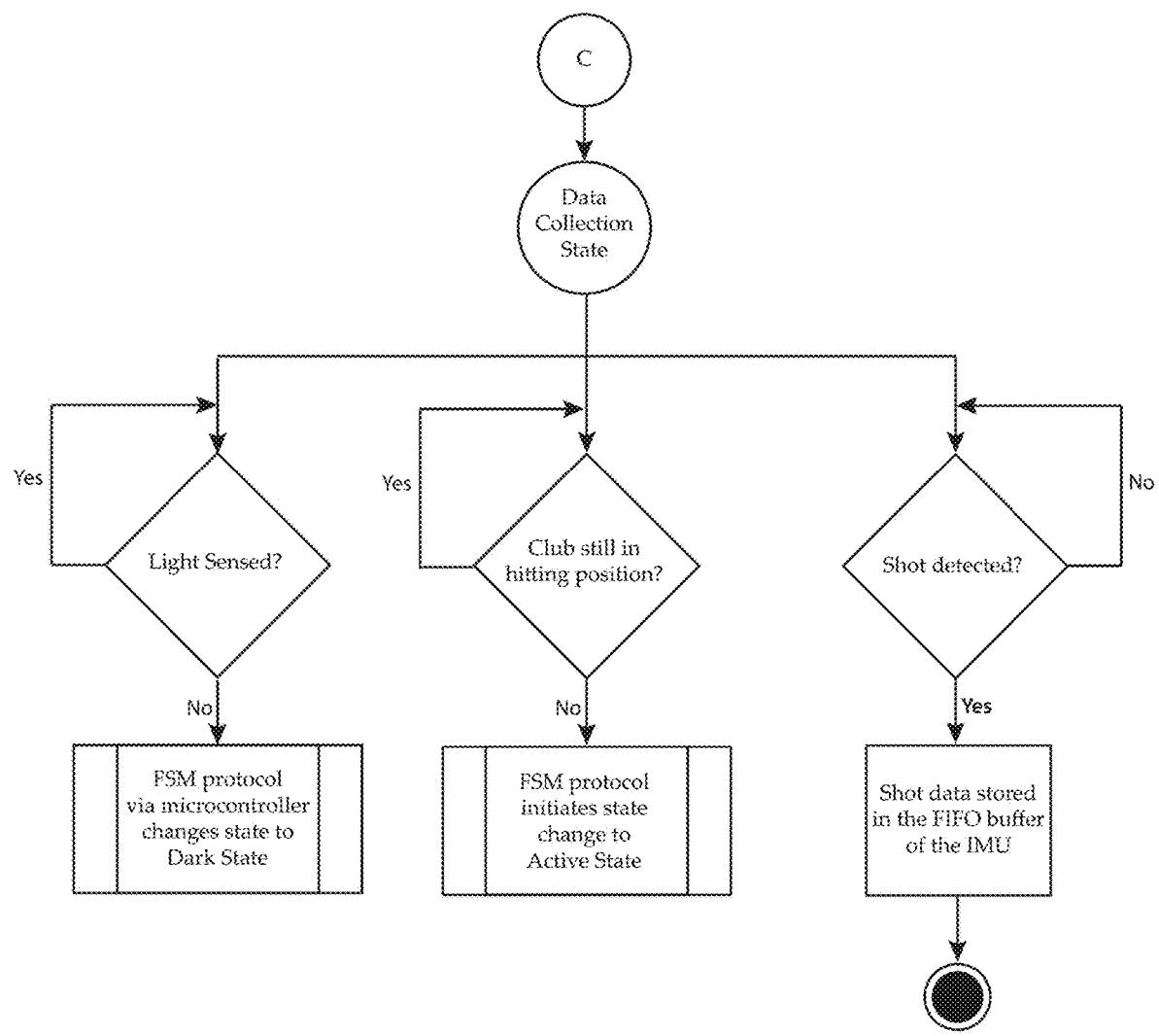
FIG. 12D illustrates a flowchart of the power state logic in a tag data collection state power mode according to one embodiment of the present invention.

FIG. 12D illustrates a flowchart of the power state logic in a data collection state according to the preferred embodiment of the present invention. In one embodiment, the tag device is operable to provide various levels of power to the light sensor, accelerometer, magnetometer, gyroscope, and the BLE radio unit when operating in a data collection state. In one embodiment, the tag device enters a data collection state when the gyroscope detects that the club is in a predetermined orientation and exhibits a movement profile that indicates an impending swing and anticipated golf ball strike. In one embodiment, the tag device enters a data collection state when the gyroscope detects that the club is in a predetermined orientation and exhibits a movement profile that indicates an impending swing and anticipated golf ball strike and the accelerometer detects movement within a predetermined threshold. The purpose of the data collection state is to activate the plurality of sensors used to detect a swing resulting in a ball strike at the last possible moment in order to both conserve battery power and collect sensor data to analyze characteristics of the golf swing.

Referencing FIG. 12D, in the preferred embodiment, when the tag device is in the data collection state, the photosensor is powered, the accelerometer is powered and operating at a high cycle rate to obtain more discrete measurements, the gyroscope is powered, the optional magnetometer is powered, and the BLE is powered in accordance with the predetermined BLE protocol. The microcontroller monitors the photosensor and the finite state machine monitors the accelerometer, the gyroscope and the optional magnetometer. As further illustrated in FIG. 12D, if the photosensor detects light below the pre-determined light threshold (i.e., indicating a return to dark conditions), the tag device follows the protocol described in FIG. 10B and returns the tag device to the dark state. If the photosensor has not measured a return to dark, as the finite state machine monitors the accelerometer and the gyroscope, if the accelerometer and the gyroscope measure a movement indicating a shot has been taken in accordance with the predetermined shot detection logic, a shot is registered and stored in the memory of the tag device. Upon storing a shot, the tag device then begins aggressively advertising through its BLE radio in accordance with the predetermined BLE protocol that a shot has been stored, and the tag device remains in the data collection state. Alternatively, upon storing a shot, the tag device is able to return to any of the other power states either by a pre-selected default or based on the then current reading of the sensors. In one embodiment, the shot data is stored in any of the tag device's memory.

In one embodiment, when a data collection state is entered, BLE is advertising and the accelerometer, gyroscope, and the magnetometer are powered and active in order to collect swing data. In one embodiment, the tag device enters a data collection power state when the light sensor detects a light level above a predetermined threshold, the golf club is determined not to be at rest, and the gyroscope detects the golf club in one or more predetermined orientations.

In one embodiment, upon transition into the data collection state, the microprocessor refreshes the finite state machine's processing logic, which instructs the plurality of sensors contained in the IMU to function at a high rate, reduced rate, and/or normal rate (i.e., provide a high, low, or normal amount of power). In one embodiment, upon transition into the data collection state the microprocessor refreshes the finite state machine's processing logic to instruct the accelerometer to function at a normal or high rate and the gyroscope to function at a normal or high rate.

In one embodiment, upon transition into the data collection state, the flash memory unit refreshes the finite state machine's processing logic, which instructs the plurality of sensors contained in the IMU to function at a high rate, reduced rate, and/or normal rate (i.e., provide a high, low, or normal amount of power). In one embodiment, upon transition into the data collection state the flash memory unit refreshes the finite state machine's processing logic to instruct the accelerometer to function at a normal or high rate and the gyroscope to function at a normal or high rate.

While FIGS. 12A-12D show the logic of the preferred embodiment for going from a lower power state, i.e., a power state that requires less powering of sensors, to a higher power state, i.e., a power state that requires more powering of sensors (e.g., in the preferred embodiment, the data collection state is a higher power state than the active state, the active state is a higher power state than the inactive state, and the inactive state is a higher power state than the dark state), one skilled in the art will appreciate that if the tag device is in a higher power state and the conditions for that state no longer exist, logic similar to that described in FIGS. 12A-12D can be used to cause the tag device to enter into a lower power state. For instance, if the tag device is in the active state, if the accelerometer measures movement below the pre-determined threshold (thus indicating the club at rest or otherwise not sufficiently moving), the finite state machine signals the microcontroller that the movement threshold has not been exceeded. The microcontroller instructs the flash memory to reload the IMU's registers based on the microcontroller's instruction, and the finite state machine, upon receiving the change in register instructions, changes the state of the device from its then current (and higher) state of the active state to the inactive (and lower) state, and the sensors are powered according to the inactive state protocol, i.e., the photosensor remains powered, the accelerometer is powered and begins measurements at the reduced cycle rate, and thus is powered at a corresponding power level sufficient for the lower cycle rate, and the BLE is powered in accordance with the predetermined BLE protocol.

Figure 13A:
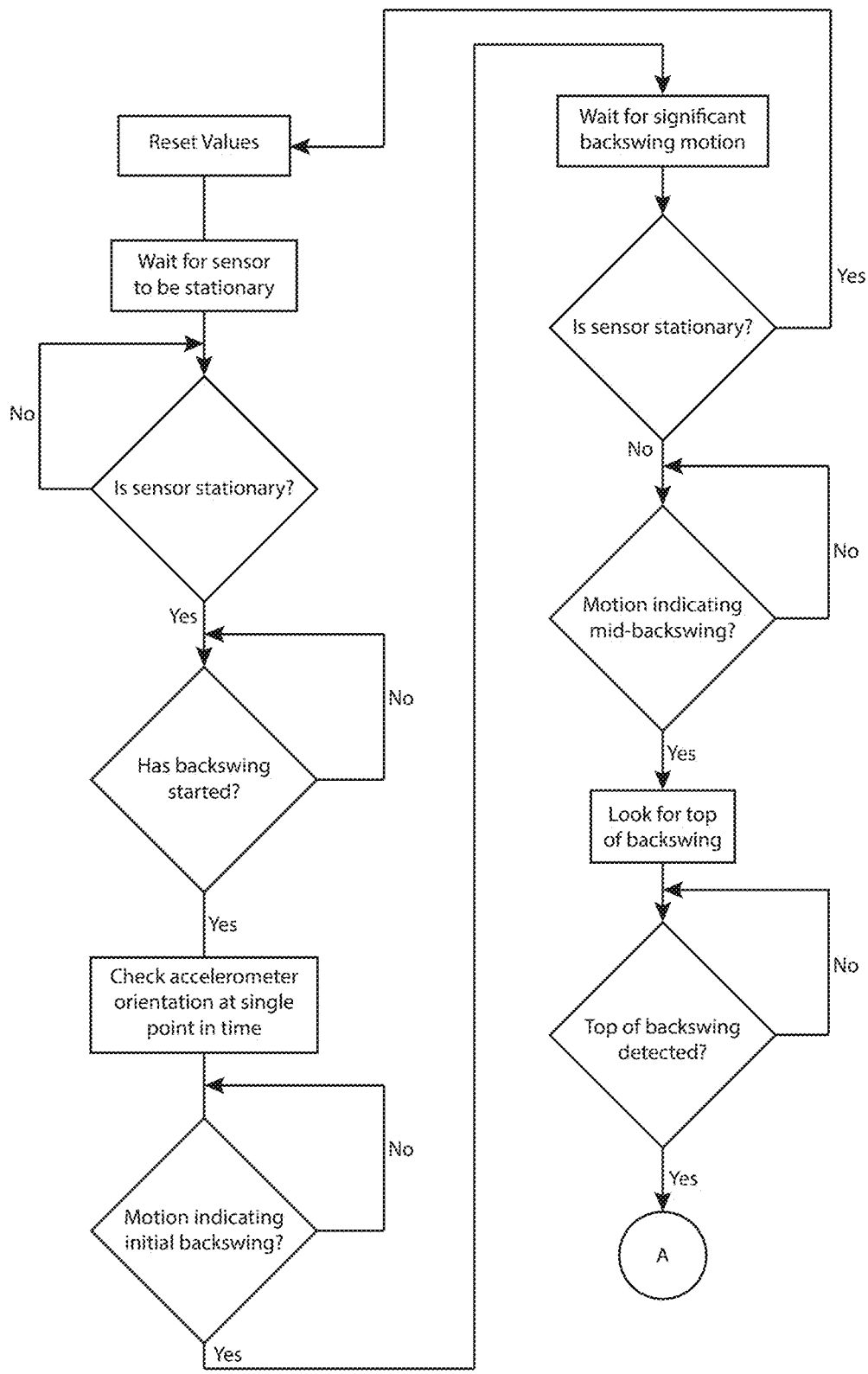
FIG. 13A illustrates a flowchart for shot detection logic according to one embodiment of the present invention.

In the data collection state, the tag device is operable to detect that a shot has been made based on pre-determined threshold or reference values corresponding to a ball strike event for the sensors in the tag device. In the preferred embodiment, shot detection is made using the logic described in FIGS. 13A-C. Referring to FIG. 13A, in the preferred embodiment, the tag device, while in the data collection state, initially monitors the sensors within the IMU to determine if the tag device is stationary. In one embodiment, sensor data from the magnetometer is also used to assist in detecting a shot. In the data collection state, the tag device initially resets the sensor values and waits for the tag device to be stationary. Upon the tag device being stationary, the IMU monitors the accelerometer and gyroscope to measure a movement indicating the golfer has started his backswing, indicated by a movement of the tag device indicating a backward movement of the club head from the perspective of the face of the club head. Upon detecting an initial backswing movement, the IMU continues to monitor the sensor data looking for a movement that indicates the tag device has continued in the motion of a backswing to the top of the swing, i.e., a motion in the form of an arc with attendant rotation of the tag device in which the tag device reaches a point at the top of the backswing where the tag device stops its movement and changes direction back toward the starting point. If the tag device, via the monitoring of its sensors by the IMU, detects that the tag device stopped during the back swing, did not complete a backswing, and thereafter remained stationary, such as, for example, the movement that occurs when the golfer simply waggled the club backwards a few inches then returned to the starting point and remained stationary, the sensor values are reset.

Figure 13B:
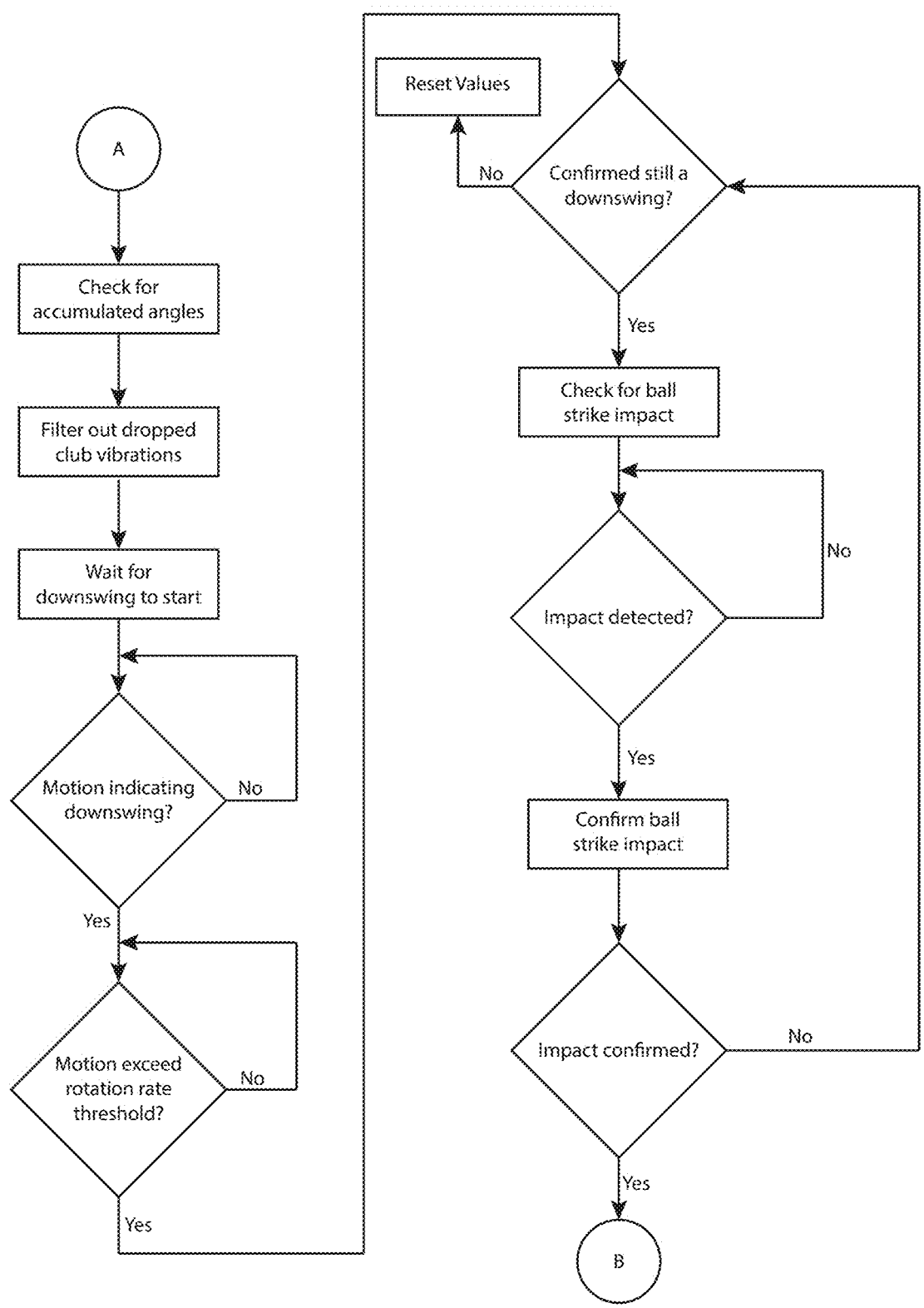
FIG. 13B illustrates a flowchart for shot detection logic according to one embodiment of the present invention.

Referring to FIG. 13B, once the top of the backswing is detected, the tag device, again via the monitoring of its sensors by the IMU, checks the accumulated angles of the tag device and filters out dropped club vibrations. The tag device, through monitoring of the sensors in the IMU, continues to monitor that the movement indicates a continuation of the swing and waits for sensors to indicate that the downswing has begun, i.e., the backward motion of the backswing has stopped at the top of the swing and the tag device (golf club) has reversed direction to move back toward the starting position. The tag device monitors that the tag device exceeds a pre-determined rotation rate, indicating that the tag device is rotating back to the starting position indicative of a golf swing. Based upon this collected data, if the data does not confirm that a downswing is still occurring, the sensor values are reset. If the data indicates that the downswing is still occurring, the IMU continues to monitor the sensors, including the accelerometer and gyroscope, to determine if certain reference values have been met, indicating an impact and a strike of the golf ball by the club. If impact is not detected by the IMU, the tag device continues to monitor for impact. If impact is detected by the IMU indicating a strike of the golf ball, e.g., based on a comparison of measured sensor output values to sensor output reference values corresponding to a ball strike, impact is then confirmed.

Figure 13C:
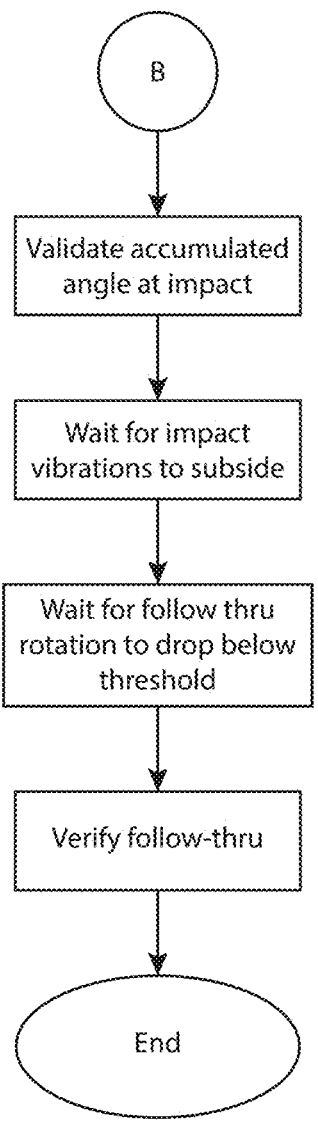
FIG. 13C illustrates a flowchart for shot detection logic according to one embodiment of the present invention.

Referring to FIG. 13C, if impact, indicating a strike of the ball, is confirmed, the tag device validates the accumulated angle of the tag device, and by extension, the golf club, at impact. Because impact results in significant vibrations of the golf club, and hence, tag device measurements, the tag device waits for club vibrations to subside. After club vibrations have subsided, the tag device, via monitoring by the IMU of its sensors, particularly the accelerometer and the gyroscope, monitors that the tag device, and hence golf club, rotation has dropped below pre-determined reference values, indicating the follow-through of the club along an arc from the starting point or point of impact to the top of the follow-through portion of the golf swing. The tag device then verifies follow through and registers that a shot was taken. In one embodiment, after the sensor data indicating a ball strike has been communicated to the remote computing device, the remote computing device makes a determination that a ball strike has occurred by comparing the sensor output values to reference values corresponding to a ball strike.

Once a shot has been detected, the shot data, including the club face angle at address, collected during the data collection state is stored in the memory of the tag device until the tag device enters the streaming state, or is able to transmit the data to another device, ushc as a connected computing display device. In one embodiment, the shot data is stored in the FIFO buffer of the IMU. In another embodiment, the shot data is stored in any of the tag device's memory. In one embodiment, the shot data stored for transmission is limited to a selected number of shots. If shot data for more than the selected number of shots is obtained before the data for the selected number of shots is transmitted to a display device, the shot data for the earliest shots still being stored is overwritten.

In one embodiment, battery life is extended because the plurality of sensors requiring higher power, such as the gyroscope and magnetometer, are activated in the data collection state. In this embodiment, by reducing the amount of processing power supplied to the higher power consuming sensors during earlier states, the tag device can greatly extend its battery life. In one embodiment, the battery life of the device is further extended by utilizing the microprocessor to refresh the operating instruction on the finite state machine. In one embodiment, the battery life of the tag device is further extended by utilizing the flash memory unit to refresh the operating instructions on the finite state machine, rather than running operational instructions on the microcontroller.

Figure 12E:
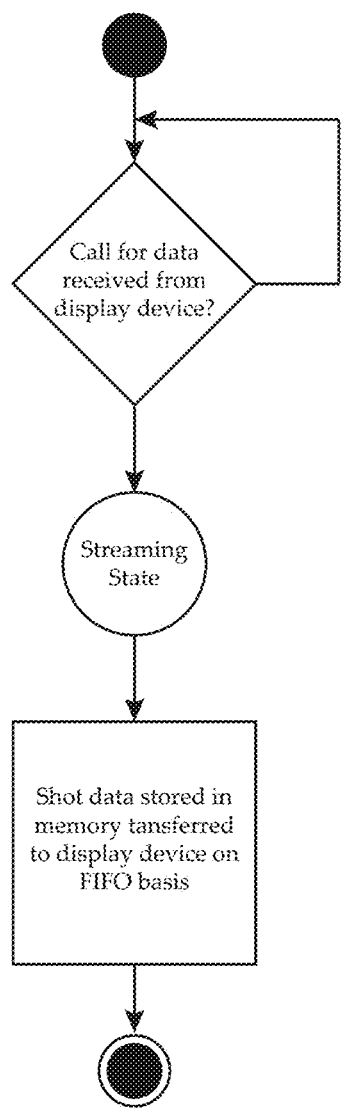
FIG. 12E illustrates a flowchart of the functional logic in a data streaming state power mode according to one embodiment of the present invention.

FIG. 12E illustrates a flowchart of the functional logic in a data streaming state power mode according to one embodiment of the present invention. In one embodiment, the data streaming state is operable to transmit sensor data in real-time to an interface, mobile, and/or display device regardless of the golf club's orientation or motion. In one embodiment, a data streaming state is activated when a light environment is sensed, motion is detected, an active state is initiated, and BLE is advertising. In one embodiment, when a data streaming power state is activated and a display device is in range of the BLE, a connection is made that facilitates a data streaming command from the display device. In one embodiment, upon initiation of the data streaming power state, real-time raw sensor data from the tag device's plurality of sensors is continually transmitted to a display device, regardless of the golf club's orientation or movement. In this embodiment, this unidirectional streaming of sensor data continues until it is terminated by the interfacing device. In the preferred embodiment illustrated in FIG. 12E, the data streaming state is entered when a call for data is received by the tag device from the connected device in accordance with the BLE protocol. Once the data streaming state is entered, the data stored in the memory of the tag device is transmitted via BLE communications to the connected display device in accordance with the BLE protocol for storage and processing.

In one embodiment, the BLE protocol avoids traditional pairing protocols with display devices by implementing a power saving BLE protocol or calibration that does not require traditional device-to-device pairing. In this embodiment, prior to conducting a golf swing, a user calibrates the tag device using their connected device (e.g., a mobile device, a GPS-enabled golf device such as the SKYCADDIE, a smartphone, or other similar devices, running a golf application). Calibration occurs by placing one's display device proximate to the tag device, which allows the display device to identify the unique characteristic, fingerprint, and/or hash of the tag device and/or its plurality of sensors (i.e., a different hash for each sensor or for each tag device). The display device then stores the unique identifying characteristics(s) in its storage. Once stored, when the golf application is initiated, the display device's communication unit "looks" for each stored tag device, which broadcasts a radio signal when a shot is stored in its memory. This allows the tag device to transmit sensor data directly to the display device through BLE protocols without having to set up a pairing code between the display device and the tag device each time the tag device is activated. Therefore, when the tag device is in the data streaming state and the BLE protocols are aggressively advertising the sensor data, a mobile device that has already been calibrated to the tag device captures the sensor data without having to pair with the tag device. This is accomplished because the tag device includes the unique characteristic, fingerprint, and/or hash in its sensor data as it is aggressively advertising the sensor data. Therefore, the mobile device easily recognizes the sensor data as the desired sensor data from the tag device and captures it for visualization for the user. In one embodiment, the BLE protocol is operable to transmit sensor data without requiring device-to-device pairing. In this embodiment, a display device is operable to capture the transmitting data without pairing to the tag device. This embodiment functions to overall reduce the use of the microcontroller 102, which contains and runs the BLE protocol. In one embodiment, the fingerprint and/or unique identifying characteristics are stored in non-volatile memory. In one embodiment, a mobile device running an application stores the tag device's fingerprint and/or hash. In one embodiment, a mobile device running an application recognizes a fingerprint or unique identifying characteristic when in range of the tag device. In one embodiment, after a valid swing has been detected and the swing data has been collected, the BLE advertises aggressively until the mobile device running an application responds, validates, and receives the plurality of swing data and/or until a predetermined timeout occurs (i.e., BLE advertises for an amount of time that indicates that data transfer will not occur). In one embodiment, where the BLE times out, the device is returned to a dark state.

In one embodiment, a user calibrates their tag device to the golf club to which it is affixed by placing the mobile device running an application on the face of the golf club in a set orientation and then moving the golf club in a set pattern. Using the gyroscope in the tag device and a gyroscope in the mobile device, specific parameters of the golf club, such as, length, loft, lie, and orientation are determined. This is accomplished because both the mobile device's gyroscope and the tag device's gyroscope are moving in a similar synchronous pattern. This process can be accomplished in a room of multiple golfers with multiple tag devices by having the tag device distinguish the movement patterns of its mobile device, affixed to its golf club, from other mobile devices, affixed to other's golf clubs. This cross correlation of gyroscope movement ensures that the mobile app recognizes and calibrates the appropriate tag device and in turn assigned a unique identifier number, fingerprint, and/or hash.

More specifically, to accomplish the above-described calibration process, first the tag device is operating in an active state with the BLE advertising. Next, the mobile device is in range of the tag device and running an application compatible with the tag device. The mobile device running an application then activates the calibration mode, and the tag device enters into a data streaming mode where the plurality of sensors are activated and outputting sensor data. Next, the mobile device is placed on the face of the golf club in a specific orientation and moved, along with the tag device, in a specific pattern. The mobile device then receives the plurality of sensor data from the tag devices and compares it to the data received from the mobile devise sensors (e.g., the gyroscope). Then, the tag device with the cross correlated gyroscope data is recognized by the mobile device and the mobile device parses the data to create a unique identifier, fingerprint, and/or hash that identifies the tag device as being on the specific gold club. Lastly, the mobile device writes that unique identifier, fingerprint, and/or has back to the tag device.

Referring to FIG. 8B, in the preferred embodiment of the present invention, when the tag device is originally manufactured, the tag device is embedded with digital information identifying the tag device. The tag device is given a unique digital identifier number, also referred to as a media access number, machine identifier number, or mac address. Additionally, because the tag device in the preferred embodiment uses BLUETOOTH as its communication vehicle, the tag device is given a unique BLUETOOTH identifier, known as a universally unique identifier or UUID. The preferred embodiment utilizes a 16-bit UUID. The BLUETOOTH related identification information also includes other BLUETOOTH-specific information, such as the tag device company's BLUETOOTH SIG identifier.

The tag device 100 is in communication with the remote computing device 400 via the wireless communication units on the tag device 100 and on the remote computing device 400. The preferred communication is through BLE communication units on both the tag device 100 and the remote computing device 400. The remote computing device 400 is a location aware device running a golf application program 401 as generally described herein in connection with FIG. 17.

During the tag device calibration process generally described herein, the tag device 100 is in communication with the golf application program 401 of the remote computing device 400. During the calibration process, information about the tag device and the golf club to which it is attached is collected and stored in the memory of the tag device 100 and the remote computing device 400. In the preferred embodiment, this includes the tag owner's customer identification number (i.e., the customer identification number given to the tag owner by the tag device company), the club type (e.g., driver, 5-iron, putter, pitching wedge, etc.) and club characteristics (e.g., loft, lie, etc.), the tag device firmware version number, and/or the sensor configuration and calibration information regarding the sensors on the tag device (e.g., the current power state of the tag device, which sensors are turned on or powered, etc.). This information, additionally including shot count data after a tag device is used to detect a shot, is referred to as the golf application data and/or as the tag device 100 fingerprint. Once embedded within the memory of the tag device 100 and the remote computing device 400, this golf application data is also communicated by the remote computing device to the tag device company's central database as generally described in connection with FIG. 16.

Tag device 100 BLE communications 801 (also referred to herein as "advertisements") contains the tag device fingerprint information and the other information described herein. When a connection is made between the tag device 100 and the connected computing 400 device, if the fingerprint information for the tag device 100 which is cached or otherwise stored in the connected computing device 400 does not match the fingerprint information of the tag device 100, such as might occur if the tag device's firmware, configuration, or calibration have been updated since the last connection with the connected computing device 400, the fingerprint information in the connected computing device's cache or other memory is updated to match that of the tag device 100. As noted, the BLE advertisement information 801 also includes the number and identification of golf shots collected and stored in the memory of the tag device 100. If the golf shots stored in the memory of the tag device 100 have not been transmitted to the connected computing device 400, upon connection of the connected computing device 400 with the tag device 100, this shot information is communicated to the connected computing device 400. The BLE advertisement information 801 also includes flags to notify the connected computing device 400 if the tag device 100 is moving, is in the data collection state, needs updating (e.g., UTC time for example), or has debugging information. The BLE advertisement information additionally contains other Bluetooth specific information to enable filtering out the tag device's advertisements from other Bluetooth enabled devices in the area. In one embodiment, the BLE advertisement initially utilizes a hash of the tag device 100 firmware version, sensor configuration version and calibration status. If any of these values change, the hash also changes, and the BLE advertising alerts connected computing devices 400 in the area of the need to reconnect to receive updated versions of the tag device 100 firmware, sensor configuration, and/or calibration. Because the hash of these values is much smaller than advertising all of this data directly, initial use of a hash followed by transmission of the full advertisement information upon connection with the connected device more efficiently serves the purpose of alerting connected devices of change in the underlying data. In one embodiment, the UUID is a 16-bit UUID and the total advertisement budget is 32-bit. In another embodiment, the UUID is a 128-bit UUID.

Referring to FIG. 8C, in the preferred embodiment, once the tag device transmits an advertisement, the tag device BLE radio immediately changes from transmit to receive and, upon receiving a connection from a connected device, the tag device returns to transmit mode and transmits the full advertisement information. BLE advertisements are made in all power states, except the dark state. The advertisement rate is affected by the power state of the tag device and by changes to the advertisement information. The baseline advertisement rate is initially determined based on the power state of the tag device. The baseline advertisement rate is then overridden if the advertisement information changes. One skilled in the art will appreciate that the advertisement rate, i.e., more frequent bursts of advertisement, are meant to occur when the connected device is more likely needing to connect with the tag device, e.g., when shot count has changed or the device goes from moving to not moving. In the data collection state, i.e., the tag device and hence golf club is in the swing orientation and moving, the advertisement interval rate is every 100 milliseconds. One skilled in the art will appreciate that in the data collection state, the golfer is in the hitting position and a shot will most likely soon occur. Therefore, it is most likely that advertisement information will very soon change and be ready for transmission to the connected device. It is desirable in that instance that a connected device be in a position to quickly connect, so more frequent advertisement is desirable. In the active state, i.e., the tag device and hence the golf club is moving but not in a swing orientation, the advertisement interval rate is every 750 milliseconds. Because the club is moving, continuous advertisement is desirable, but because the club is not in the hitting position, the rate need not be as frequent as in the data collection state. In the inactive power state, i.e., the tag device and hence golf club is not moving, the advertisement interval rate is every 750 milliseconds for 30 seconds, then advertisements are stopped. In the inactive state where the golf club is not moving, there is little likelihood that a connected device will need to connect in the near term, thus after an initial burst of advertisement, no further advertisements are warranted. In the dark state, the tag device, and hence the golf club, is in a condition such as storage or otherwise not being used, so there is no need for any advertisements. BLE advertisements are also made when there are changes to the advertisement information, regardless of the power state, other than the dark state in which no advertisements are made. Some common examples of a change in advertisement information include the detection and storage of a golf shot, a change in the power state, or a change in the tag device firmware or sensor configuration. In the case of a change in advertisement information, it is desirable that the connected device be notified quickly, so the advertisement rate is increased. Further, since advertisements are sometimes missed by the connected device, a number of bursts over a short period of time increases the likelihood of the connected device being responsive, after which a return to the baseline rate is warranted. In the preferred embodiment, when there is a change in the advertisement information, which includes a change in the power state of the tag device, the advertisement interval rate is every 100 milliseconds for a total of 3 seconds, after which the rate returns to the baseline rate for the power state the tag device is in.

In one embodiment, using the BLE protocol described above, the unique characteristic, fingerprint, and/or hash connected to the sensor data of a specific tag device is shared with other display devices (e.g., tablet, TV, phone, etc.). This greatly reduces processing power needed by the tag device because the transfer of the unique fingerprint is accomplished by the mobile device rather than the tag device itself. This allows the BLE to function at a lower power rate for a longer time during a golf game while still being able to visualize swing data on a plurality of devices. In effect, power is conserved while function quality is maintained.

In one embodiment, using the BLE protocol described above, a plurality of tag devices and mobile devices can share sensor data with each other while recognizing what sensor data is whose. As an example, multiple users each calibrate one or more tag devices to one or more mobile devices (using the method described above) prior to beginning a golf game. Thereafter, when the golfers each conduct a first golf swing, the sensor data is transmitted to their respective mobile devices without the need for each golfer to find and pair a specific tag device (containing their individual strike data) to a specific mobile device. This allows the user to receive golf swing sensor data after each golf swing without having to pair a device, which would be further complicated by the presence of multiple tag devices and multiple mobile devices. By eliminating BLE pairing between the tag device and a mobile device the microcontroller's need for processing power is greatly reduced and in turn the battery life of the tag device is extended.

In one embodiment, using the BLE protocol described above, the tag device is operable to simultaneously display sensor data on multiple display devices at once (i.e., on a single golfer's tablet, phone, watch, etc.). Additionally, the tag device is operable to display sensor data on one or more display devices (e.g., TVs) in a golf hitting bay. In this embodiment, battery power is saved by avoiding BLE pairing with each individual display device, one at a time. This further reduces battery power by avoiding round robin communication (i.e., display devices having to "wait in line" to be paired to the tag device).

In one embodiment, the BLE protocol described above is further operable to implement a golf swing rejection protocol with a mobile device running a complimentary application to further reduce the processing power used by the tag device. In this embodiment, not only does the tag device identify itself to a mobile device with a unique fingerprint, the tag device identifies each individual golf swing and the sensor data associated with it with an additional unique fingerprint recognizable by the mobile device. This allows the mobile device to recognize what sensor data has already been received (thus rejecting any subsequent attempt to transmit it) and what sensor data is yet to be received. Furthermore, using this protocol, the amount of sensor data stored by the tag device is able to be reduced.

As an example, shot data is stored in the memory of the tag device, which is configured to only store five golf swings. In this example, the tag device has been pre-calibrated with a mobile device so that the mobile device has a unique identification number, ESN, fingerprint, and/or hash to identify sensor data associated with the tag device and has an additional unique identification number, ESN, fingerprint, and/or hash to identify for each golf swing, e.g., one to five. More specifically, golf swing sensor data one has a unique identification number that identifies it as coming from the tag device and identifying it as the sensor data associated with a first golf swing. Golf swing two, three, four, and five have similar identification numbers to the first golf swing and these identification numbers identify the data as coming from the specific tag device but having the added benefit of identify what number golf swing they represent in the sequence. Therefore, each consecutive golf swing is identified and captured by the mobile device during BLE protocol in an orderly fashion. What results is a reduction in processing power because only five golf swings are stored at a time. The tag device needs only store data associated with five golf swings because each golf swing sensor data point is transmitted to the connected device. In the preferred embodiment, if the data for any of the five shots stored in the tag device is not transmitted to the connected device, once the sixth golf swing is accomplished, the first golf swing data is overwritten and a similar process continues for subsequent golf swings. The mobile device is operable to reject any data it has already received and accept new golf swing data yet to be received. This embodiment serves to extend battery life by reducing processing power and serves to minimize the size and weight of the tag device by requiring less memory space.

Figure 14:
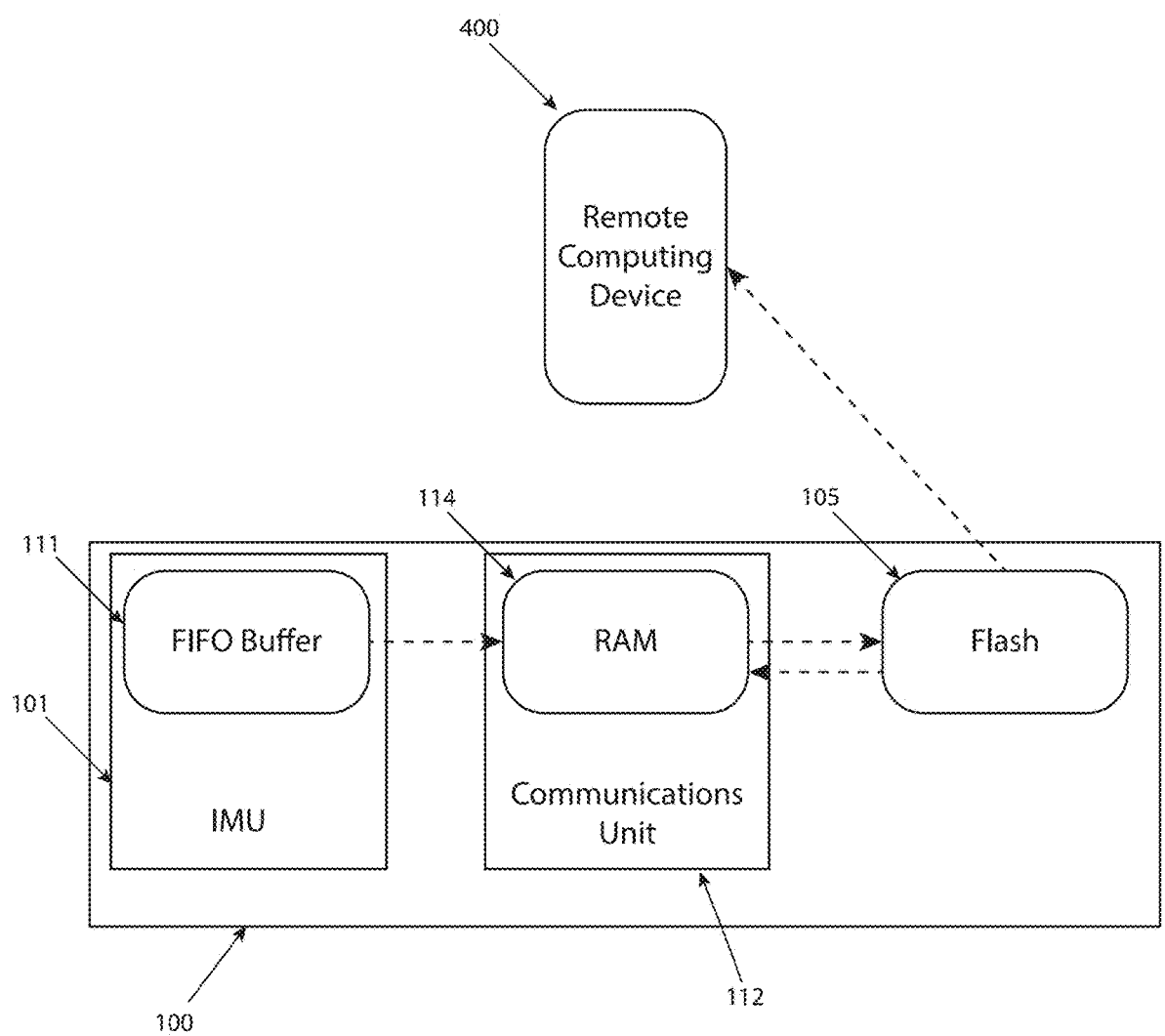
FIG. 14 illustrates a sequential diagram in which sensor data is stored in memory storage units according to one embodiment of the present invention.

Referring to FIG. 14, in one embodiment of the present invention, the IMU 101 includes a FIFO buffer 111 that stores sensor data, e.g., from accelerometers, gyroscopes, magnetometers, as it is generated by the sensors, and includes a BLUETOOTH processing chip 112 that contains RAM 114 available for use outside BLUETOOTH operations. The FIFO buffer 111 has limited storage capacity, e.g., 3 KB for the preferred embodiment, and typically stores data uncompressed. Sensor data for a detected swing will often exceed the FIFO buffer 111 capacity. In the preferred embodiment, sensor data for a detected swing is typically as much as 13 KB after compression. The FIFO buffer 111 is configured with a "watermark," which is a reference mark that is triggered when the FIFO buffer 111 begins to approach its capacity. Once the watermark is achieved, the BLUETOOTH processor chip 112 reads the FIFO data into RAM 114 memory and compresses it into a circular buffer. The circular buffer overwrites the oldest samples as necessary, e.g., if data for more than a selected maximum number of swings (five swings for the preferred embodiment) is stored in the RAM 114. When the FSM 101 detects that sensor data is a swing or ball strike, a new "collection" of swing data is created. This collection of data includes, for example, the UTC swing time, MAC address of the device, configurations and calibrations of the sensors, and/or other golf application data as discussed herein, together with the related raw sensor swing data that is currently in the circular buffer. In the preferred embodiment, this collection of data is routed or saved through the RAM 114 but is not fully saved in the RAM 114. Instead, as it is received by the RAM 114 it is then saved to the flash memory 105 of the tag device 101 in piecemeal fashion. Thus, the full collection of data is ultimately stored in the flash 105 of the tag device 100, which in the preferred embodiment is SPI flash. Once the data is saved to flash 105, the tag device 100 begins BLE advertising as described herein, the swing detection is reset, and the tag device 100 begins looking for a new swing. After the remote device signals the tag device 100 that it is ready to receive the sensor data, the tag device 100 begins transmitting the sensor data via its BLUETOOTH communications unit 112 to the remote computing device 400. To do this, the sensor data in the tag device flash 105 is transmitted from the flash 105 to the tag device's RAM 114 in small bits of data in order to reduce the need for a large RAM and is then transmitted to the remote computing device 400.

Figure 15:
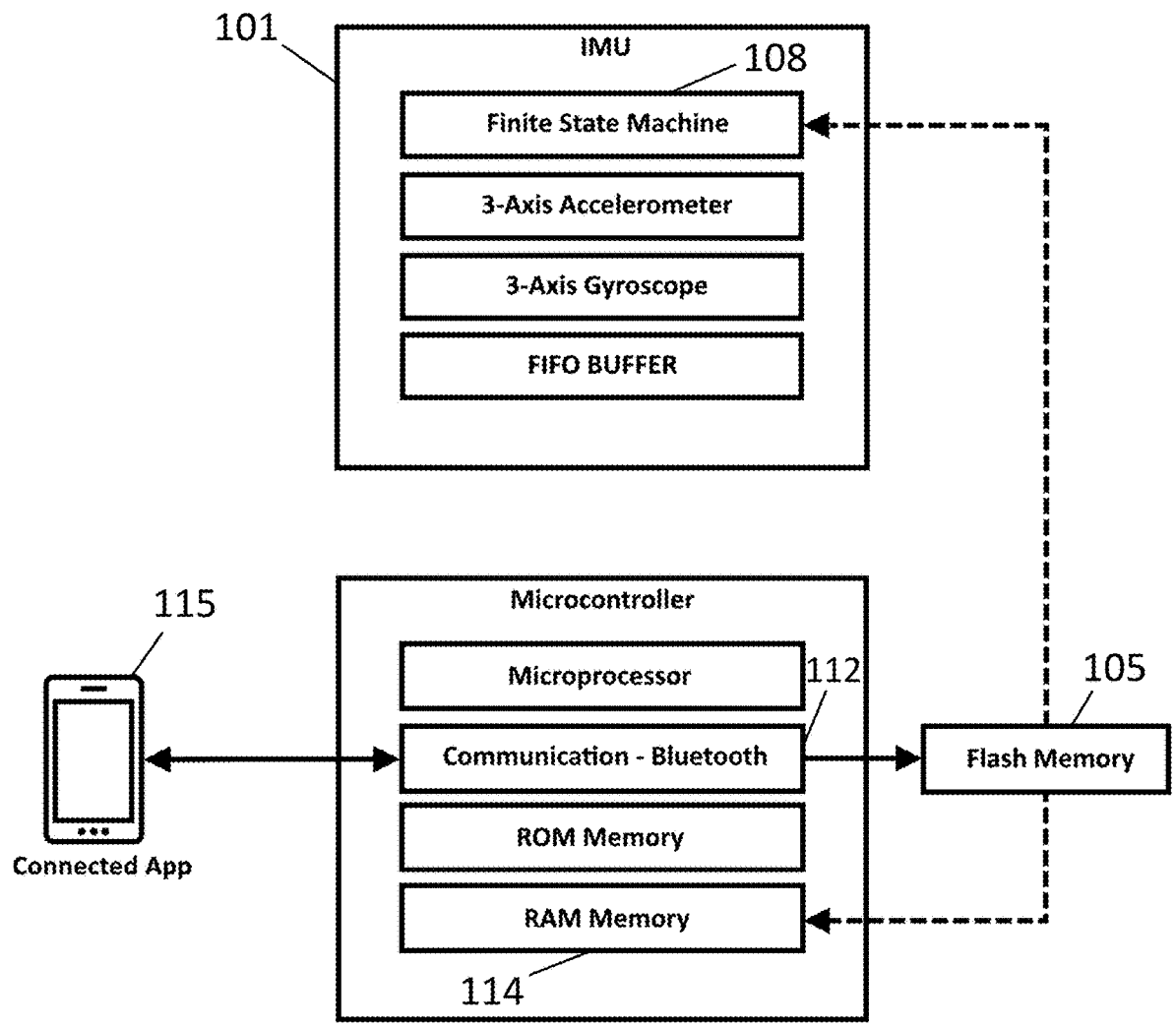
FIG. 15 illustrates a flowchart of the tag device where data is transferred to flash memory and distributed to non-volatile memory and registers of the tag device according to one embodiment of the present invention.

FIG. 15 illustrates a flowchart of the tag device where data is transferred to flash memory 105 and distributed to non-volatile memory and registers of the tag device according to one embodiment of the present invention. In one embodiment, updates to the operational code of the tag device are transmitted, stored by flash memory 105, and distributed to RAM memory 114, and registers to the finite state machine 108. In one embodiment, for the updates to the operational code of the tag device to be transmitted, the tag device must be in an active state and/or any state where BLE is advertising. In one embodiment, a mobile device app 115 connects to the tag device and transfers the updates to the operational code of the tag device to the flash memory 105 whereby the old operational code is overwritten by the new operational code. In one embodiment, the mobile device app 115 sends a reboot command to the tag device, which reboots and distributes the operation code to the finite state machine 108 and/or the RAM memory 114.

In one embodiment, the microprocessor 116 is operable to refresh the processing logic of the finite state machine 108 upon transition from one power state to another (e.g., from dark state to inactive state). Refreshing the processing logic of the finite state machine 108 is operable to instruct the IMU 101 to provide less, more, and/or the same amount of processing power to the plurality of sensors. Furthermore, using the microprocessor 116 to refresh the processing logic of the finite state machine 108, rather than using the ROM memory unit 113 or the RAM memory unit 114, results in less processing power being used by the microcontroller 102, which increases battery life.

In one embodiment, the flash memory unit 105 is operable to refresh the processing logic of the finite state machine 108 upon transition from one power state to another (e.g., from dark state to inactive state). Refreshing the processing logic of the finite state machine 108 is operable to instruct the IMU 101 to provide less, more, and/or the same amount of processing power to the plurality of sensors. Furthermore, using the flash memory unit 105 to refresh the processing logic of the finite state machine 108, rather than using the ROM memory unit 113 or the RAM memory unit 114, results in less processing power being used by the microcontroller 102, which increases battery life.

In a typical use case, the tag device will enter a dark state when the golf club it is affixed to is in a golf bag or in a dark environment. In a typical use case, the tag device is operable to transition from a dark state to an inactive state when the golf bag is removed from a golfer's car or otherwise carried around in a golf course. In a typical use case, the tag device is operable to transition from an inactive power state to an active power state when the golf club bag is set down in a tee box. In a typical use case, the tag device is operable to transition from an inactive power state to an active power state when the golf club is removed from its golf bag. In a typical use case, the tag device is operable to transition between active and inactive states when a golfer is moving a golf club in anticipation of conducting their next golf swing. In a typical use case, the tag device is operable to transition from an active power state to a collection power state when the golfer is in a position to strike a golf ball. In a typical use case, the tag device is operable to transition from a collection state to another state upon contact of the golf club to the golf ball. In a typical use case, the tag device is operable to transition from any state other the dark state to a streaming power state to transmit the swing data to a display device, such as a SKYCADDIE. In a typical use case, the tag device is operable to transition to a plurality of different power states after each golf swing is completed.

Figure 16:
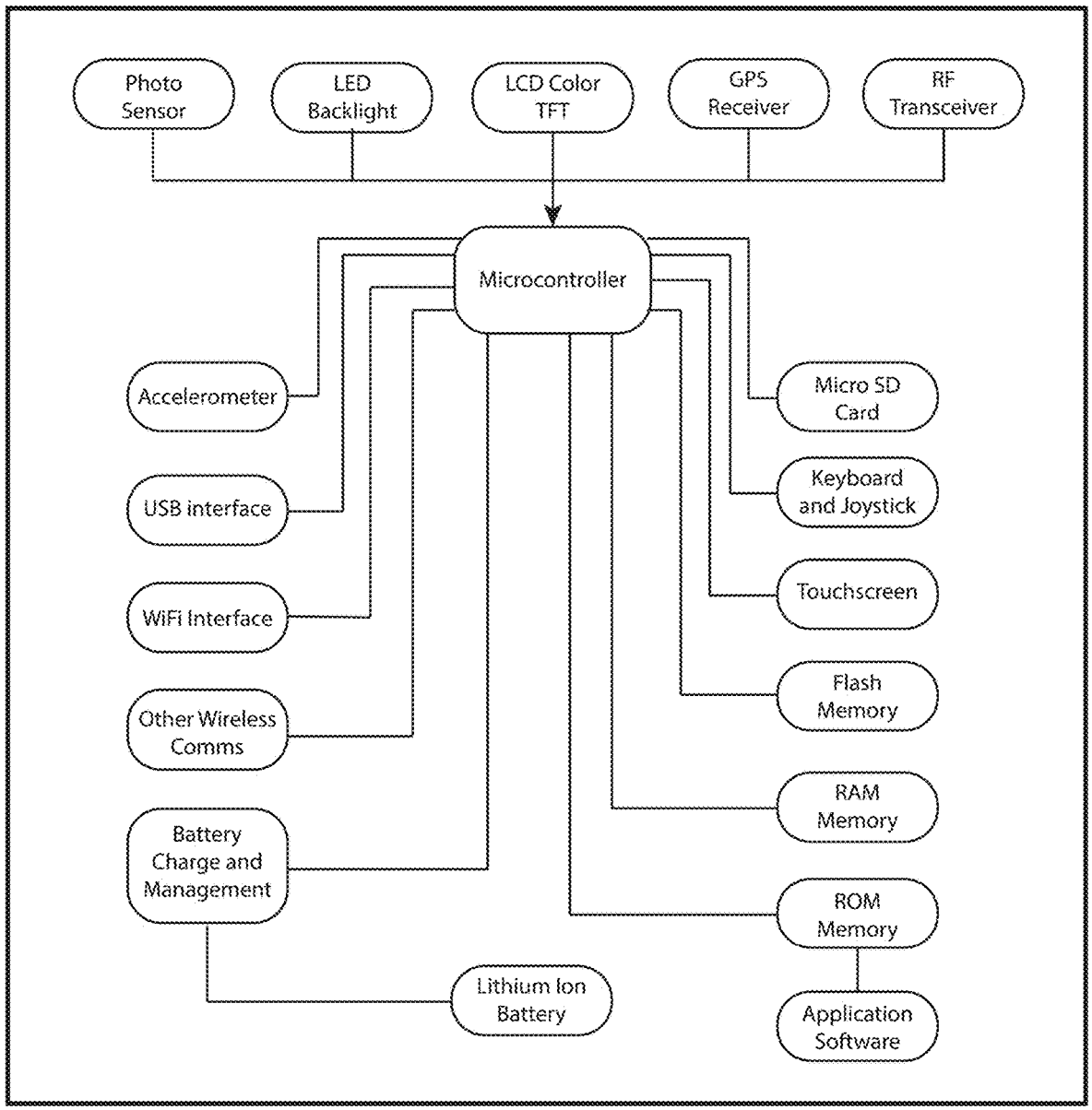
FIG. 16 illustrates a block diagram of an electronic architecture of a remote computing device according to one embodiment of the present invention.

An exemplary configuration of one of the distributed computing devices (e.g., the location aware device) able to be used with the present invention is shown and described with reference to FIG. 16. The remote computing device may be a hand-held device including multiple components that are managed by microcontroller running software stored in a flash memory or random-access memory, for example. The microcontroller serves as an interface and controller for a plurality of hardware systems and device application systems of the remote computing device. In an exemplary embodiment, the primary purposes of the portable remote computing device are to provide a golfer with distance information to various points on a green and to various targets and hazards on the golf course, to further process the sensor output data received from the tag device, to provide location information for the tag device and ball strike events, and to provide a display to visualize swing depictions derived from tag device sensor output data.

The remote computing device is a location-aware device in which distance information is provided to the user by referencing geolocated mapped data stored in the flash memory, for example, to the real time Global Positioning System (GPS) position data acquired by an onboard GPS receiver. The microcontroller processes the GPS data and derives calculations to the mapped points and various areas on the course. The position data of the remote computing device is time-stamped so that in-coming sensor output data associated with a ball strike event, which is also timestamped, is able to be associated with the precise location of the remote computing device at the time of the ball strike event. This permits the location of the remote computing device to be a proxy for the location of the ball strike event. This location and distance information is then displayed to the player through a graphical user interface that includes, for example, a sunlight readable color thin-film transistor (TFT) liquid crystal display (LCD) display having a light-emitting diode (LED) backlight. The LED backlight is controlled by a photosensor that measures ambient light and adjusts the brightness of the backlight accordingly. The LCD is transflective so the backlight brightness is reduced when the unit is in sunlight, and the brightness is increased when the unit is in low light conditions.

The microcontroller also receives input from the player by a user input device, such as a touchscreen, a button, a keyboard, a mouse, a joystick, or an audio-activated input device. The user input corresponds to, for example, a command to move a cursor on the graphical user interface, enter data, select a particular course for display, select a shot to pull up a sub-screen with additional shot data or a swing depiction, or otherwise control the remote computing device.

As noted above, the mapped course data is stored in an onboard flash memory, which is able to be updated via connection of a Universal Serial Bus (USB) port, micro-Secure Digital (micro-SD) card, WI-FI radio or other wireless communications device. An operating system of the microcontroller and various applications executed by the microcontroller are also able to utilize the onboard RAM for storage of temporary data.

The remote computing device is powered by a battery that is managed by a charging circuit and power management circuit to provide power to the various components of the location-aware device. The remote computing device also includes a radio-frequency (RF) transceiver that receives signals transmitted from the device tags.

Data transmitted from the tag device is received by the remote computing device transceiver and is further processed by the microcontroller. The microcontroller analyzes the sensor output data received from the tag device to determine if the output matches a pattern of data indicating a ball strike event. The microcontroller compares the received sensor output data against stored "signatures" or reference values corresponding to a ball strike event to determine whether a ball strike event has occurred. The remote computing device also includes a "physics engine", which is software, and programming to render a 2-D to 3-D image of the swing.

This data, including as further processed, is stored in a memory (e.g., flash memory and/or RAM memory) and is used by the microcontroller to automate the scoring process, display the round and shot data graphically on the device, and to be available to upload the data to a computer and/or website for post-round analysis and graphical tracking of the player's golf shots over the course of a round.

Figure 17:
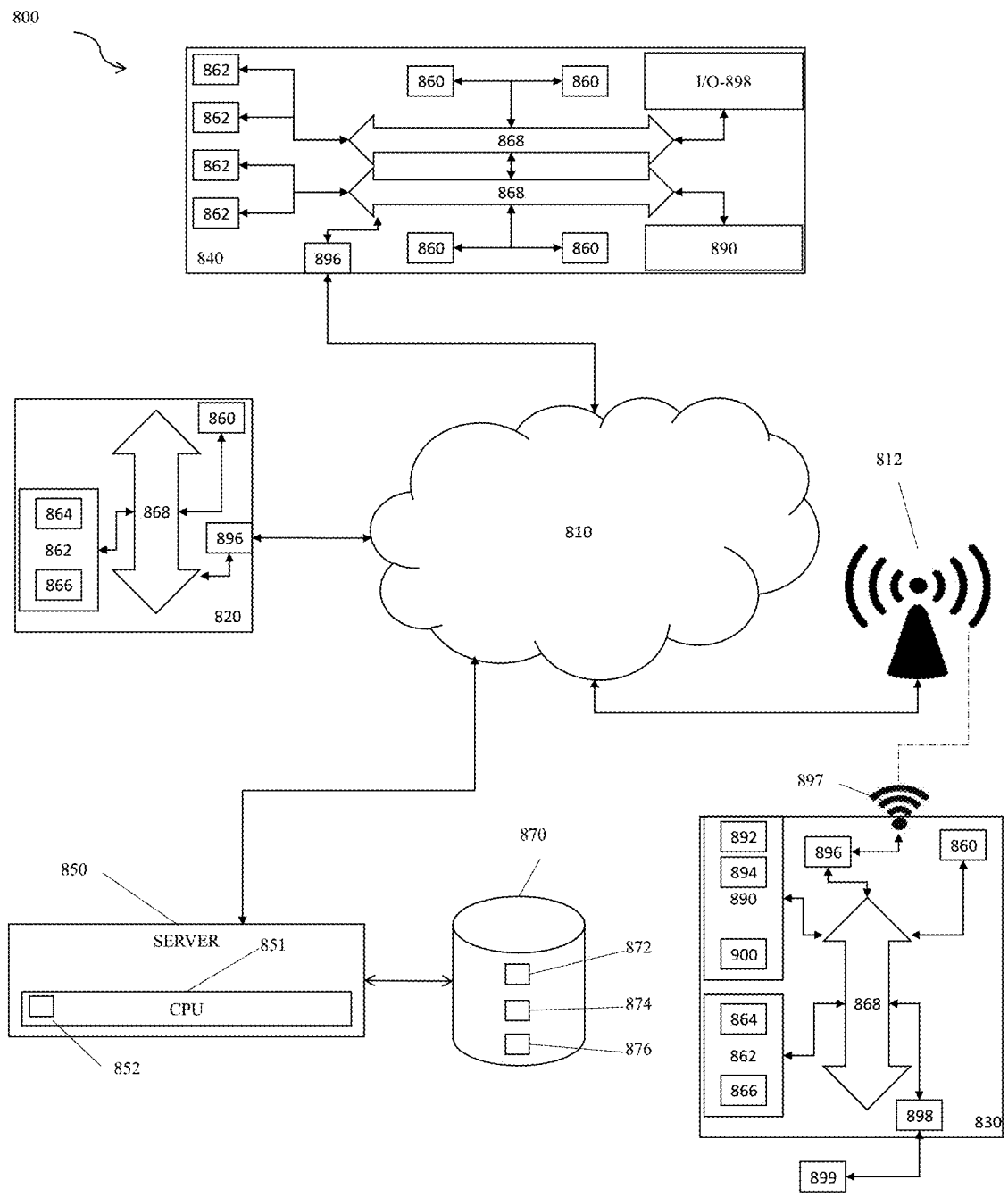
FIG. 17 is a schematic diagram of a system of the present invention.

FIG. 17 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 17, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections, or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 17 is operable to include other components that are not explicitly shown in FIG. 17 or is operable to utilize an architecture completely different than that shown in FIG. 17. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A tag device for determining alignment of a golf swing, comprising:
    an inertial measurement unit comprising a plurality of sensors, wherein the plurality of sensors are configured to output a signal based on a detected condition, movement or orientation of the tag device;
    a microcontroller including a microprocessor;
    a memory in communication with the microcontroller and the inertial measurement unit;
    a transceiver configured to transmit data corresponding to sensor outputs from the plurality of sensors to a remote computing device; and
    a battery;
    wherein the tag device is attached to a golf club;
    wherein the plurality of sensors includes at least one magnetometer;
    wherein the tag device is in network communication with at least one location-aware device, including a location aware unit and a display;

wherein the tag device determines an actual alignment of the golf club based on the signal output from the plurality of sensors and transmits the actual alignment to the at least one location-aware device; and wherein the at least one location-aware device determines a difference value comparing an intended target line to the actual alignment of the golf club.

2. The tag device of claim 1, wherein the plurality of sensors further include at least one accelerometer, at least one gyroscope, and/or at least one piezo sensor.

3. The tag device of claim 2, wherein the at least one magnetometer is calibrated based on sensor data produced by the at least one accelerometer and/or the at least one gyroscope.

4. The tag device of claim 1, wherein vectors representing the intended target line and the actual alignment of the golf club are displayed graphically on the display of the at least one location-aware device.

5. The tag device of claim 1, wherein the location aware unit includes at least one global positioning system (GPS) chip.

6. The tag device of claim 1, wherein the at least one location-aware device automatically determines the intended target line based on input selection of a target location on a map interface.

7. The tag device of claim 1, wherein the difference value is determined for an address of a golf ball, an impact between the golf club and the golf ball, and/or during one or more points during the golf swing between the address and the impact.

8. The tag device of claim 1, wherein the at least one location-aware device includes at least one smartphone, at least one tablet, and/or at least one computer.

9. A system for determining alignment of a golf swing, comprising:
- a tag device attached to a golf club, including:
  - an inertial measurement unit comprising a plurality of sensors, wherein the plurality of sensors are configured to output a signal based on a detected condition, movement or orientation of the tag device;
  - a microcontroller including a microprocessor;
  - a memory in communication with the microcontroller and the inertial measurement unit;
  - a transceiver configured to transmit data corresponding to sensor outputs from the plurality of sensors to a remote computing device; and
  - a battery; and
- at least one location-aware device, in network communication with the tag device, including a location aware unit and a display;
- wherein the plurality of sensors includes at least one magnetometer;
- wherein the output signal from the plurality of sensors of the tag device is used to determine an actual alignment of the golf club; and
- wherein the at least one location-aware device determines a difference value comparing an intended target line to the actual alignment of the golf club.

10. The system of claim 9, wherein the plurality of sensors further include at least one accelerometer, at least one gyroscope, and/or at least one piezo sensor.

11. The system of claim 10, wherein the at least one magnetometer is calibrated based on sensor data produced by the at least one accelerometer and/or the at least one gyroscope.

12. The system of claim 9, wherein vectors representing the intended target line and the actual alignment of the golf club are displayed graphically on the display of the at least one location-aware device.

13. The system of claim 9, wherein the location aware unit includes at least one global positioning system (GPS) chip.

14. The system of claim 9, wherein the at least one location-aware device automatically determines the intended target line based on input selection of a target location on a map interface.

15. The system of claim 9, wherein the difference value is determined for an address of a golf ball, an impact between the golf club and the golf ball, and/or during one or more points during the golf swing between the address and the impact.

16. The system of claim 9, wherein the at least one location-aware device includes at least one smartphone, at least one tablet, and/or at least one computer.

17. A method for determining alignment of a golf swing, comprising:
- providing a tag device, including a plurality of sensors, a microcontroller, a memory, a transceiver, and a battery, attached to a golf club in network communication with at least one location-aware device, including a location aware unit and a display;
- the plurality of sensors of the tag device outputting a signal based on a detected condition, movement or orientation of the tag device;
- determining an actual alignment of the golf club based on the output signal from the plurality of sensors; and
- the at least one location-aware device determining a difference value comparing an intended target line to the actual alignment of the golf club;
- wherein the plurality of sensors includes at least one magnetometer.

18. The method of claim 17, further comprising the display of the at least one location-aware device graphically displaying vectors representing the intended target line and the actual alignment of the golf club.

19. The method of claim 17, further comprising the at least one location-aware device automatically determining the intended target line based on input selection of a target location on a map interface.

20. The method of claim 17, further comprising determining the difference value for an address of a golf ball, an impact between the golf club and the golf ball, and/or during one or more points during the golf swing between the address and the impact.

* * * * *